(12) United States Patent
Bassin

(10) Patent No.: US 12,702,773 B2
(45) Date of Patent: Aug. 11, 2026

(54) APPARATUS AND METHODS FOR VENTILATORY TREATMENT

(71) Applicant: ResMed Pty Ltd, Bella Vista (AU)

(72) Inventor: David John Bassin, Coogee (AU)

(73) Assignee: ResMed Pty Ltd (AU)

( * ) Notice: Subject to any disclaimer, the term of this patent is extended or adjusted under 35 U.S.C. 154(b) by 1643 days.

(21) Appl. No.: 17/017,552

(22) Filed: Sep. 10, 2020

(65) Prior Publication Data

US 2021/0093812 A1 Apr. 1, 2021

Related U.S. Application Data

(63) Continuation of application No. 14/391,910, filed as application No. PCT/AU2013/000382 on Apr. 12, 2013, now abandoned.

(Continued)

(51) Int. Cl.
*A61M 16/00* (2006.01)
*A61B 5/00* (2006.01)
(Continued)

(52) U.S. Cl.
CPC ....... *A61M 16/0069* (2014.02); *A61B 5/4818* (2013.01); *A61M 16/0051* (2013.01);
(Continued)

(58) Field of Classification Search
CPC .......... A61M 16/0069; A61M 16/0051; A61M 16/0633; A61M 16/0683; A61M 16/1055;
(Continued)

(56) References Cited

U.S. PATENT DOCUMENTS

| | | | |
|---|---|---|---|
| 4,944,310 A | 7/1990 | Sullivan | |
| 5,704,345 A * | 1/1998 | Berthon-Jones | A61F 5/56 128/207.18 |

(Continued)

FOREIGN PATENT DOCUMENTS

| | | |
|---|---|---|
| AU | 2006225224 A1 | 10/2006 |
| CN | 1886169 A | 12/2006 |

(Continued)

OTHER PUBLICATIONS

Extended European Search Report from corresponding EP Application No. 22191654.7-1113 dated Jan. 24, 2023.

(Continued)

*Primary Examiner* — Timothy A Stanis
*Assistant Examiner* — Matthew R Moon
(74) *Attorney, Agent, or Firm* — Botos Churchill IP Law LLP

(57) ABSTRACT

A ventilatory treatment system is configured to treat respiratory disorders, such as obstructive sleep apnea, Cheyne-Stokes respiration, and/or the like. The system can identify and respond to different types of flow limitations, such as M-shaped inspiratory flow limitation, reverse-chair inspiratory flow limitation, and/or the like. The system can adjust Expiratory Positive Airway Pressure (EPAP) based on real-time measurements of a patient's airflow, ventilation patterns, and/or the identified flow limitation. The system can compute a measure of typical recent ventilation such that a rate of adjustment of the measure of typical recent ventilation is reduced as a measure of recent uncompensated leak increases. The system can compute a target ventilation from a product of the measure of typical recent ventilation and a target fraction, wherein the target fraction is dependent on the recent pressure support. Other embodiments may be described and/or claimed.

19 Claims, 36 Drawing Sheets

Related U.S. Application Data

(60) Provisional application No. 61/623,643, filed on Apr. 13, 2012.

(51) Int. Cl.
*A61M 16/06* (2006.01)
*A61B 5/08* (2006.01)
*A61B 5/087* (2006.01)
*A61B 5/113* (2006.01)
*A61B 5/145* (2006.01)
*A61M 16/10* (2006.01)

(52) U.S. Cl.
CPC ...... *A61M 16/026* (2017.08); *A61M 16/0633* (2014.02); *A61B 5/08* (2013.01); *A61B 5/087* (2013.01); *A61B 5/1135* (2013.01); *A61B 5/14542* (2013.01); *A61M 2016/0027* (2013.01); *A61M 2016/0036* (2013.01); *A61M 16/0683* (2013.01); *A61M 16/1055* (2013.01); *A61M 16/107* (2014.02); *A61M 2202/0208* (2013.01); *A61M 2205/15* (2013.01); *A61M 2205/18* (2013.01); *A61M 2205/3365* (2013.01); *A61M 2205/3553* (2013.01); *A61M 2205/3584* (2013.01); *A61M 2205/3592* (2013.01); *A61M 2205/505* (2013.01); *A61M 2230/432* (2013.01); *A61M 2230/435* (2013.01); *A61M 2230/63* (2013.01)

(58) Field of Classification Search
CPC ........ A61M 16/107; A61M 2016/0027; A61M 2016/0036; A61M 2202/0208; A61M 2205/15; A61M 2205/18; A61M 2205/3365; A61M 2205/3553; A61M 2205/3584; A61M 2205/3592; A61M 2205/505; A61M 2230/432; A61M 2230/435; A61M 2230/63; A61M 16/022–026; A61M 2016/0015; A61M 16/00–0003; A61M 16/0018–0042; A61B 5/4818; A61B 5/08; A61B 5/087; A61B 5/1135; A61B 5/14542; A61B 5/0809; A61B 5/0826
USPC ..................................................... 128/204.23
See application file for complete search history.

(56) References Cited

U.S. PATENT DOCUMENTS 5,794,615 A 8/1998 Estes
5,931,160 A 8/1999 Gilmore et al.
6,085,747 A * 7/2000 Axe .................... A61M 16/024 128/204.23
6,401,713 B1 6/2002 Hill et al.
6,532,957 B2 3/2003 Berthon-Jones
6,532,959 B1 3/2003 Berthon-Jones
6,532,960 B1 3/2003 Yurko
6,553,992 B1 4/2003 Berthon-Jones et al.
6,626,176 B1 9/2003 Madaus et al.
6,644,312 B2 11/2003 Berthon-Jones et al.
6,752,151 B2 6/2004 Hill
6,810,876 B2 11/2004 Berthon-Jones
7,520,279 B2 4/2009 Berthon-Jones
2001/0039950 A1 11/2001 Scholler et al.
2002/0023644 A1 2/2002 Berthon-Jones
2003/0050568 A1 3/2003 Green et al.
2004/0016433 A1* 1/2004 Estes ................. A61M 16/0069 128/204.21
2004/0134496 A1 7/2004 Cho et al.
2005/0039750 A1* 2/2005 Wickham .......... A61M 16/0069 128/204.23
2006/0000475 A1 1/2006 Matthews
2006/0060198 A1* 3/2006 Aylsworth ........... A61B 5/0205 128/204.23
2006/0070624 A1 4/2006 Kane et al.
2006/0276718 A1* 12/2006 Madaus ............... A61B 5/4818 600/538
2007/0089741 A1 4/2007 Bohm et al.
2007/0163590 A1* 7/2007 Bassin ................ A61M 16/024 128/204.23
2007/0227538 A1 10/2007 Scholler et al.
2008/0053444 A1 3/2008 Estes et al.
2008/0295837 A1* 12/2008 McCormick ...... A61M 16/0051 600/529
2008/0302364 A1 12/2008 Garde
2009/0007914 A1 1/2009 Bateman
2009/0044805 A1 2/2009 Somaiya et al.
2009/0078256 A1* 3/2009 Armitstead ......... A61M 16/026 128/204.23
2010/0101574 A1 4/2010 Bassin
2010/0236555 A1* 9/2010 Jafari ................ A61M 16/0051 128/204.23
2010/0275921 A1 11/2010 Schindhelm et al.
2010/0300445 A1 12/2010 Chatburn et al.
2010/0307500 A1* 12/2010 Armitstead ............ A61B 5/725 128/204.23
2011/0029910 A1 2/2011 Thiessen
2011/0041850 A1 2/2011 Vandine et al.
2011/0203588 A1* 8/2011 Armitstead ....... A61M 16/0069 128/204.21
2011/0265794 A1* 11/2011 Berthon-Jones ............................ A61M 16/0003 128/204.23
2012/0006328 A1 1/2012 Berthon-Jones
2012/0192874 A1* 8/2012 Bolea ................ A61N 1/37235 128/202.16
2013/0096452 A1 4/2013 Hanusse

FOREIGN PATENT DOCUMENTS

EP 1132106 A2 9/2001
EP 1179354 A2 2/2002
EP 0969763 B1 1/2008
EP 1985326 B1 6/2011
EP 2368593 A1 9/2011
JP H03267040 A 11/1991
JP 2002505924 A1 2/2002
JP 2002516159 A 6/2002
JP 2004130124 A 4/2004
JP 2007512049 A 5/2007
JP 2007301372 A 11/2007
JP 2008546432 A 12/2008
JP 2010526568 A 8/2010
WO 9222244 A1 12/1992
WO 1998012965 A1 4/1998
WO 9924099 A1 5/1999
WO 9945989 A1 9/1999
WO 03008027 A1 1/2003
WO 2004066804 A2 8/2004
WO 2005051469 A1 6/2005
WO 2005063323 A1 7/2005
WO 2006024107 A1 3/2006
WO 2006034549 A2 4/2006
WO 2006039587 A1 4/2006
WO 2006066337 A1 6/2006
WO 2006133495 A1 12/2006
WO 2007101296 A1 9/2007
WO 2007140512 A1 12/2007
WO 2008025064 A1 3/2008
WO WO-2008138040 A1 * 11/2008 ........ A61M 16/0003
WO 2009026582 A1 2/2009
WO 2010070497 A1 6/2010
WO 2010097718 A1 9/2010
WO WO-2011006184 A1 * 1/2011 ........ A61M 16/0069

OTHER PUBLICATIONS

Tero, Aittokallio , et al., "Analysis of Inspiratory Flow Shapes in Patients With Partial Upper-Airway Obstruction During Sleep",

(56) References Cited

OTHER PUBLICATIONS

Chest, vol. 119, No. 1, Jan. 1, 2001 (Jan. 1, 2001), pp. 37-44, XP093011 710, us ISSN: 0012-3692, DOI: 10.1378/chest.119.1.37, 11 pp. , p. 39; figure 1.
Chinese Search Report for Application No. 2013800198270, dated Jul. 3, 2017.
Extended European Search Report for Application No. 13775522.9 dated Nov. 25, 2015.
International Search Report and Written Opinion for Application No. PCT/AU2013/000382 dated Aug. 7, 2013.
Japanese Office Action issued in corresponding JP application No. 2018-032315 on Jan. 22, 2019.
Third Office Action issued in corresponding Chinese application No. 2018100542535 on Apr. 16, 2021.
Japanese Office Action for Application No. JP2022-128874 dated Jan. 16, 2024, 9 pages.

* cited by examiner

APPARATUS AND METHODS FOR VENTILATORY TREATMENT

CROSS-REFERENCE TO RELATED APPLICATIONS

This application is a continuation of U.S. patent application Ser. No. 14/391,910, filed on Oct. 10, 2014, which is a national phase entry under 35 U.S.C. § 371 of International Application No. PCT/AU2013/000382, filed Apr. 12, 2013, published in English, which claims priority from U.S. Provisional Application No. 61/623,643, filed Apr. 13, 2012, all of which are incorporated herein by reference.

STATEMENT REGARDING FEDERALLY SPONSORED RESEARCH OR DEVELOPMENT

Not Applicable

THE NAMES OF PARTIES TO A JOINT RESEARCH DEVELOPMENT

Not Applicable

SEQUENCE LISTING

Not Applicable

BACKGROUND OF THE INVENTION

(1) Field of the Invention

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Periodic breathing disorders of central origin, such as Cheyne-Stokes respiration, may occur together with upper airway obstruction.

The diagnosis of CSR usually involves conducting a sleep study and analyzing the resulting polysomnography ("PSG") data. In a full diagnostic PSG study, a range of biological parameters are monitored that typically include a nasal flow signal, measures of respiratory effort, pulse oximetry, sleeping position, and may include: electroencephalography ("EEG"), electrocardiography ("ECG"), electromyography ("EMG") and electro-oculography ("EOG"). Breathing characteristics are also identified from visual features, thus allowing a clinician to assess respiratory function during sleep and evaluate any presence of CSR. While the examination by a clinician is the most comprehensive method, it is a costly process and depends heavily upon clinical experience and understanding.

Systems

One known product used for treating sleep disordered breathing is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway obstruction by pushing the soft palate and tongue forward and away from the posterior oropharyngeal wall.

Non-invasive ventilation (NIV) has been used to treat CSR, OHS, COPD, MD and Chest Wall disorders. In some cases of NIV, the pressure treatment may be controlled to enforce a target ventilation by measuring a tidal volume or minute ventilation, for example, and controlling the measure of ventilation to satisfy the target ventilation. Servo-controlling of the measure of ventilation, such as by a comparison of an instantaneous measure of ventilation and a long term measure of ventilation, may serve as a treatment to counteract CSR. In some such cases, the form of the pressure treatment delivered by an apparatus may be Pressure Support ventilation. Such a pressure treatment typically provides generation of a higher level of pressure during inspiration (e.g., an IPAP) and generation of a lower level of pressure during expiration (e.g., an EPAP).

Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

PAP Device

The air at positive pressure is typically supplied to the airway of a patient by a PAP device such as a motor-driven blower. The outlet of the blower is connected via a flexible delivery conduit to a patient interface as described above.

BRIEF SUMMARY OF THE TECHNOLOGY

The present technology is directed towards providing medical devices used in the detection, diagnosis, amelioration, treatment, or prevention of respiratory disorders having one or more of improved comfort, cost, efficacy, ease of use and manufacturability.

A first aspect of the present technology relates to apparatus used in the detection, diagnosis, amelioration, treatment or prevention of a respiratory disorder.

Another aspect of the present technology relates to methods used in the detection, diagnosis, amelioration, treatment or prevention of a respiratory disorder.

Aspects of the present technology provide methods for evaluating or assessing patient SDB events and/or ventilation, which may be implemented in apparatus for assessment of ventilation or apparatus for generating a respiratory pressure treatment.

Aspects of the present technology provide methods and apparatus that automatically adjust the level of EPAP in order to counteract upper airway obstruction during respiratory pressure treatment of periodic breathing.

One aspect of one form of the present technology comprises a servo-ventilator configured to control the pressure of a supply of air so as to achieve a target ventilation, which, in response to a misleading change in measured ventilation, for example as a result of a sudden change in leak, reduces a rate of adjustment of the target ventilation.

One aspect of one form of the present technology comprises a servo-ventilator configured to: continuously compute a target ventilation such that the target ventilation rises more slowly as a measure of recent uncompensated leak increases, and control the pressure of a supply of air so as to achieve the target ventilation.

One aspect of one form of the present technology comprises apparatus or methods for treating a respiratory disorder that provide a measure of typical recent ventilation that rises more slowly as a measure of recent uncompensated leak increases.

Another aspect of one form of the present technology comprises apparatus or methods for treating a respiratory disorder that provide a target ventilation whose rate of increase is bounded by an upper limit.

Another aspect of one form of the present technology comprises apparatus or methods for treating a respiratory disorder that provide a target ventilation that falls more swiftly as the stability of recent pressure support increases, so as to improve patient comfort.

These three most recently described aspects may be particularly advantageous when used in combination.

Another aspect of one form of the present technology comprises apparatus or methods for treating a respiratory disorder that adjust a value of expiratory positive airway pressure (EPAP) according to the duration of a detected apnea or hypopnea, such that with increasing duration, the adjusted value of EPAP exponentially approaches a value that is greater than a maximum EPAP value, to improve the ability of the EPAP to splint the airway during ventilation.

Another aspect of one form of the present technology comprises apparatus or methods for treating a respiratory disorder that reduce the number of false negatives in hypopnea detection by detecting hypopnea dependent on: an extent to which pressure support being delivered to the patient is large; and an extent to which a measure of absolute value of airflow of the patient is small compared to a target absolute airflow.

These two most recently described aspects may be particularly advantageous when used in combination.

Another aspect of one form of the present technology comprises apparatus or methods for treating a respiratory disorder that increase an EPAP value according to a computed measure of M-shaped inspiratory flow limitation, such that the amount of increase is dependent on a ratio of breathwise ventilation to typical recent ventilation, so as to reduce the effect of "behavioural" breaths on the EPAP value.

Another aspect of one form of the present technology comprises apparatus or methods for treating a respiratory disorder that compute a measure of M-shaped inspiratory flow limitation of a patient based on a version of an inspiratory flow waveform that is symmetrised around a location of a notch in an inspiratory flow waveform.

These two most recently described aspects may be particularly advantageous when used in combination.

Another aspect of one form of the present technology comprises apparatus or methods for treating a respiratory disorder that increase an EPAP value according to a computed measure of reverse-chairness of inspiratory flow limitation, such that the amount of increase depends on the consistency of reverse-chairness between current and preceding breaths, so as to reduce the adverse consequences of EPAP increase.

Another aspect of one form of the present technology comprises apparatus or methods for treating a respiratory disorder that compute a measure of reverse chairness of inspiratory flow limitation of a patient dependent on the extent of recent uncompensated leak in the delivery of airflow to the patient.

These two most recently described aspects may be particularly advantageous when used in combination.

Another aspect of one form of the present technology comprises apparatus or methods for treating a respiratory disorder that increase an EPAP value according to a computed measure of inspiratory snore, in the absence of expiratory snore.

Another aspect of one form of the present technology comprises apparatus or methods for treating a respiratory disorder that compute a measure of inspiratory snore as a mean over an inspiratory portion of a current breath of a difference between the output of a snore filter on an instantaneous interface pressure and a threshold that is dependent on the instantaneous interface pressure.

Another aspect of one form of the present technology comprises apparatus or methods for treating a respiratory disorder that compute a measure of expiratory snore using joint thresholds on duration and intensity of the output of a snore filter on an instantaneous interface pressure during an expiratory portion of a current breath.

These three most recently described aspects may be particularly advantageous when used in combination, so as to reduce EPAP increases due to "spurious snore".

Another aspect of one form of the present technology comprises apparatus or methods for treating a respiratory disorder that estimate a phase of a current breathing cycle of a patient, such that a weight given to a standard rate of change in the phase estimate is dependent on an extent to which the patient has recently been achieving ventilation at or above a target ventilation, so as to improve tolerance of lower respiratory rates and short-term variations in the respiratory rate.

This most recently described aspect may be used in combination with any of the previously described aspects or combinations thereof.

Another aspect of one form of the present technology comprises apparatus or methods for treating a respiratory disorder that deliver pressure support to a patient at a value that is a combination of: a value of pressure support that is sufficient to increase instantaneous ventilation to a target ventilation; and a value of pressure support that is sufficient to increase gross alveolar ventilation to a target gross alveolar ventilation, so as to treat patients with periodic breathing and respiratory insufficiency.

This most recently described aspect may be used in combination with any of the previously described aspects or combinations thereof.

Other aspects of the present technology comprise computer readable storage media having recorded thereon computer program code that is configured to cause a processor to carry out methods according to the above described aspects.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

Treatment Systems

Respiratory System

Figure 1A:
FIG. 1*a* shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.
Figure 2A:
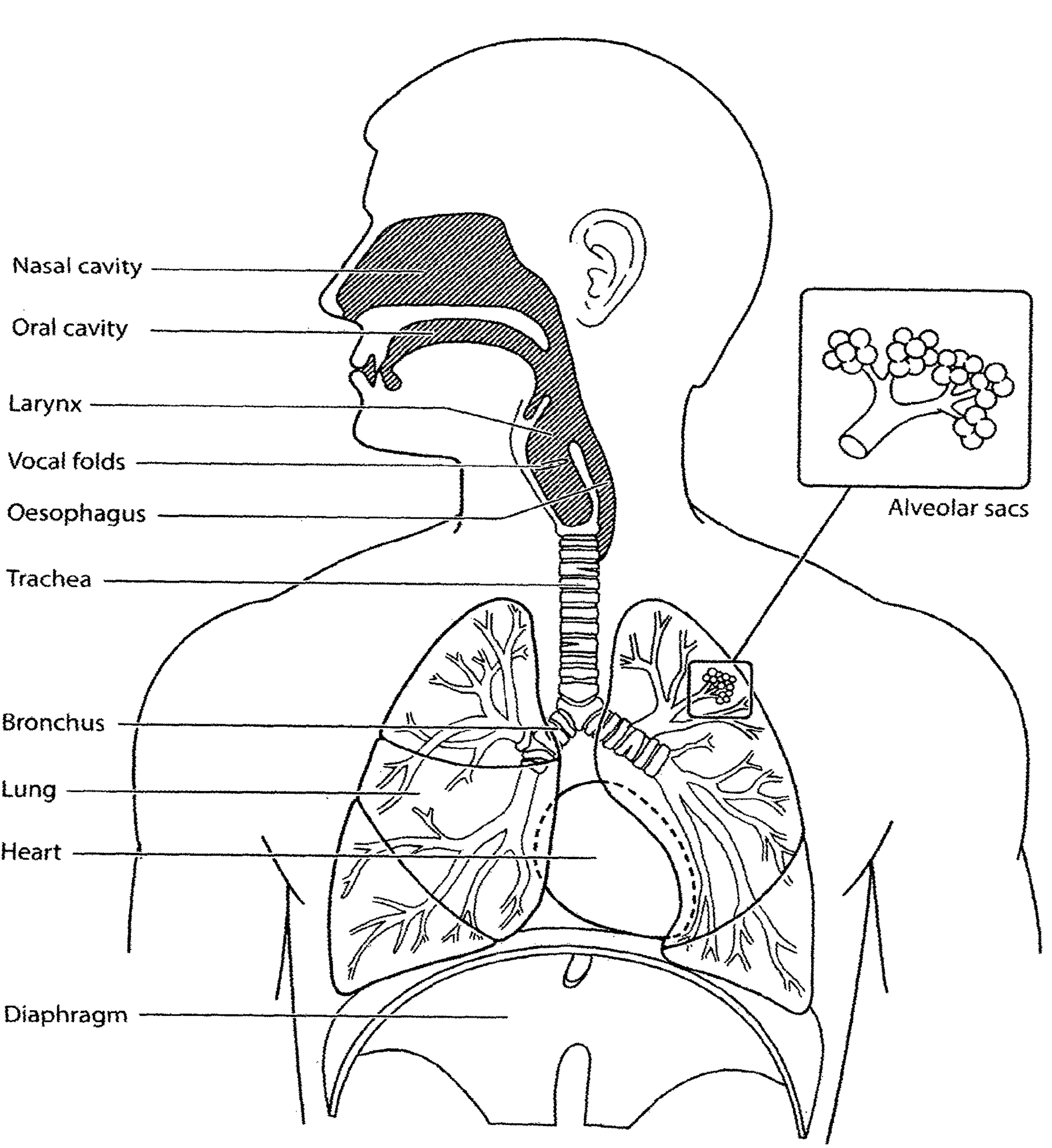

FIG. 2*a* shows an overview of a human respiratory system including the nasal and oral cavities, the larynx, vocal folds, oesophagus, trachea, bronchus, lung, alveolar sacs, heart and diaphragm.

Figure 2B:
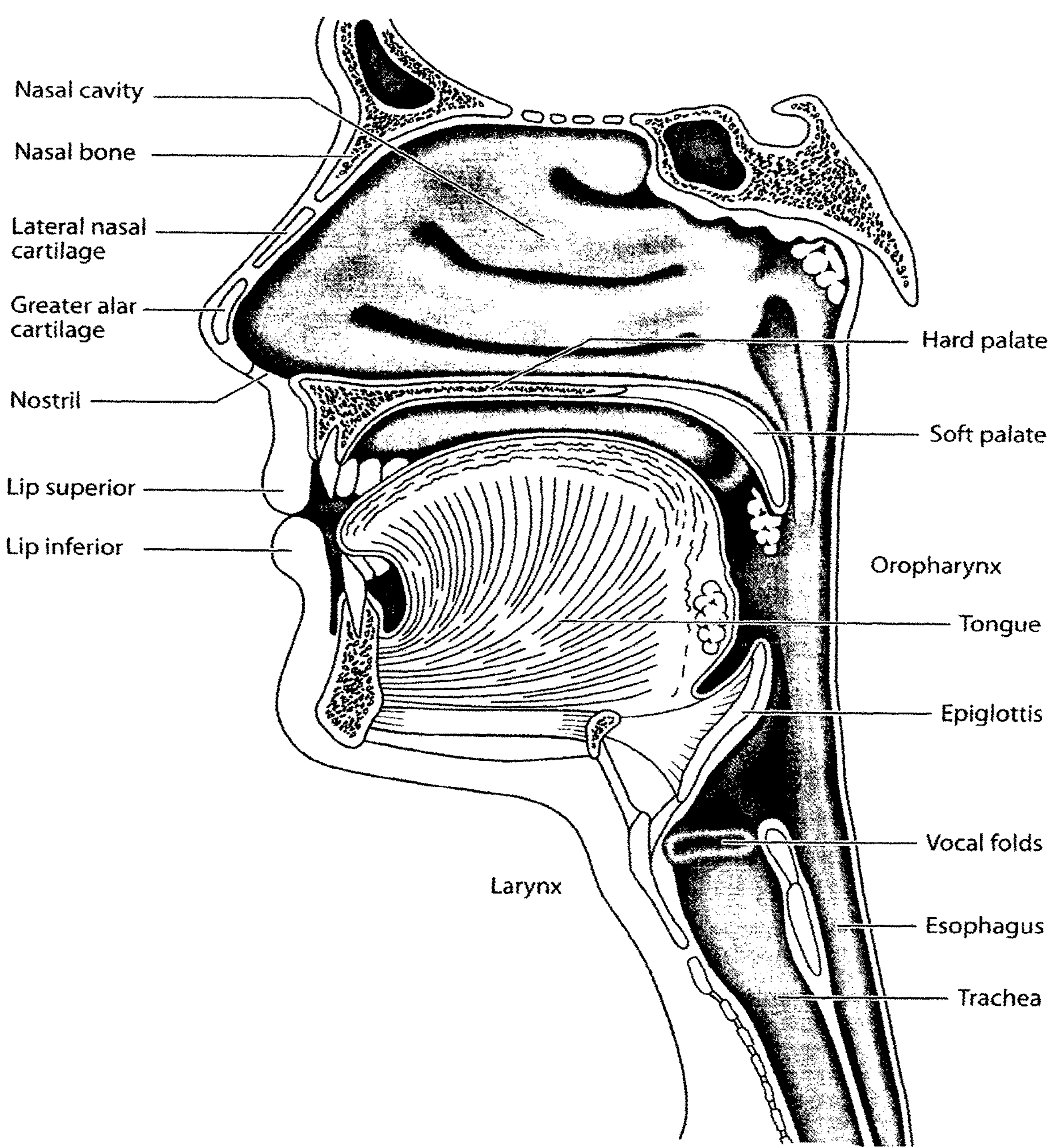

FIG. 2*b* shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Patient Interface

Figure 3A:
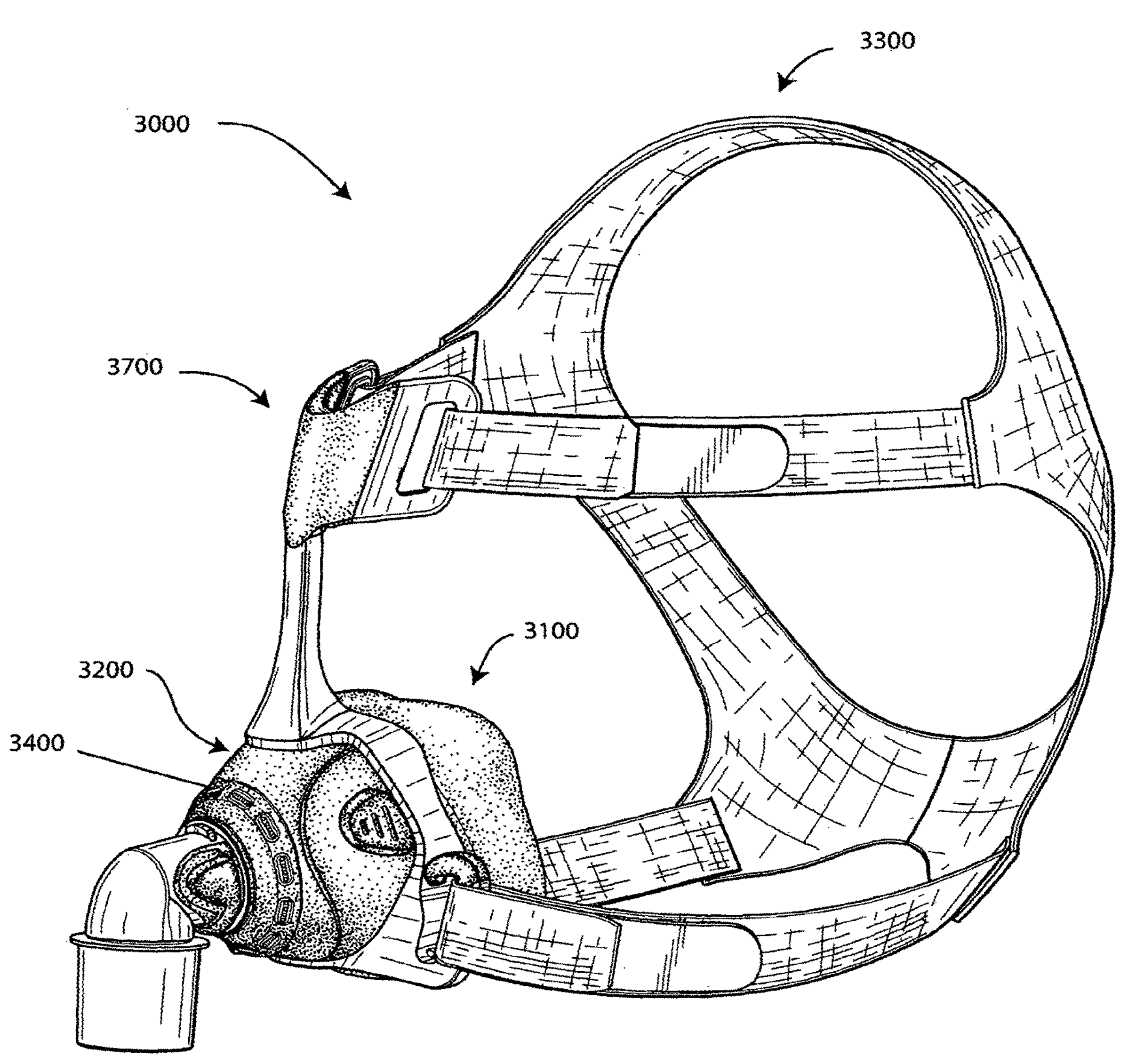

FIG. 3*a* shows a patient interface in accordance with one form of the present technology.

PAP Device

Figure 4A:
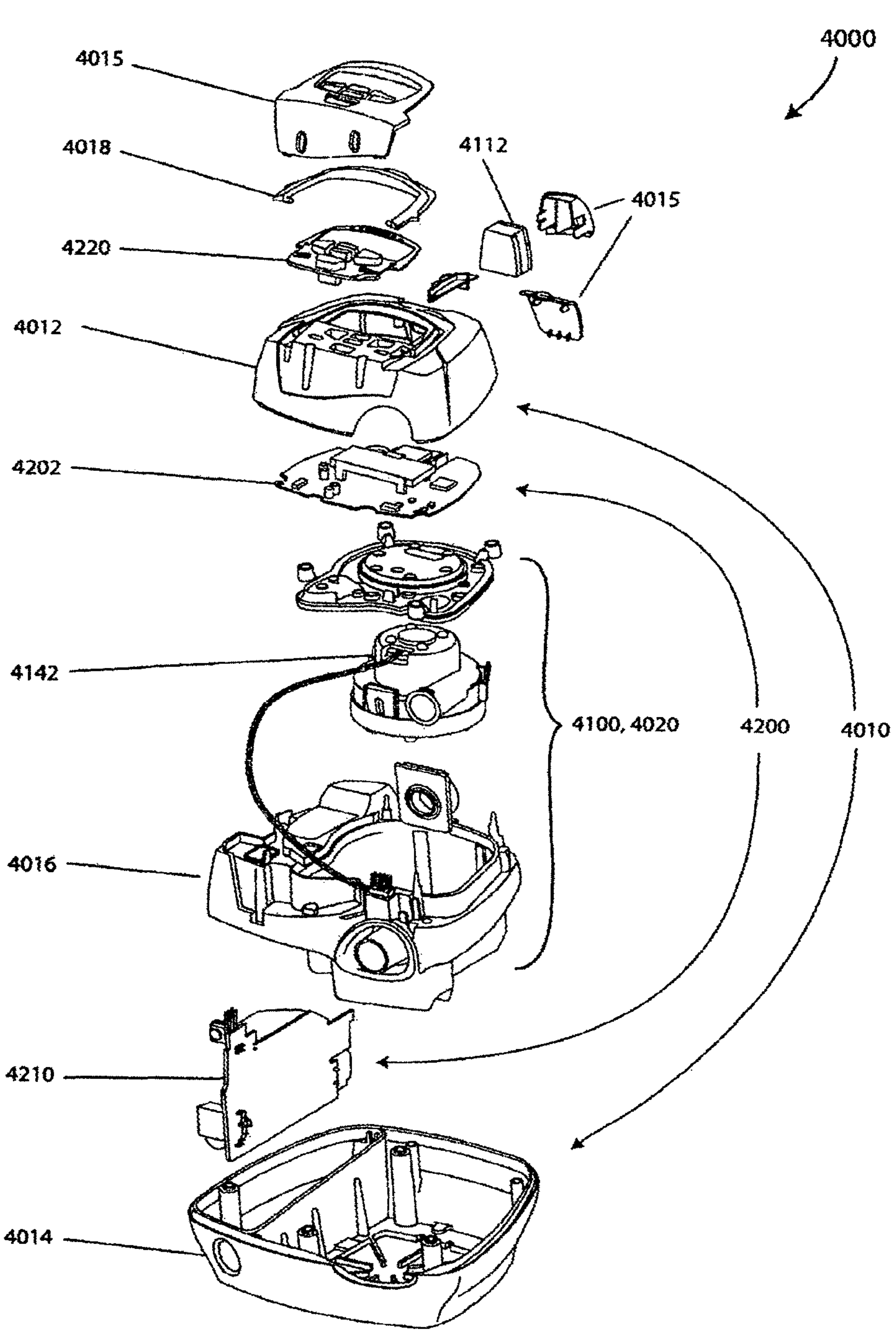

FIG. 4*a* shows a PAP device in accordance with one form of the present technology.

Figure 4B:
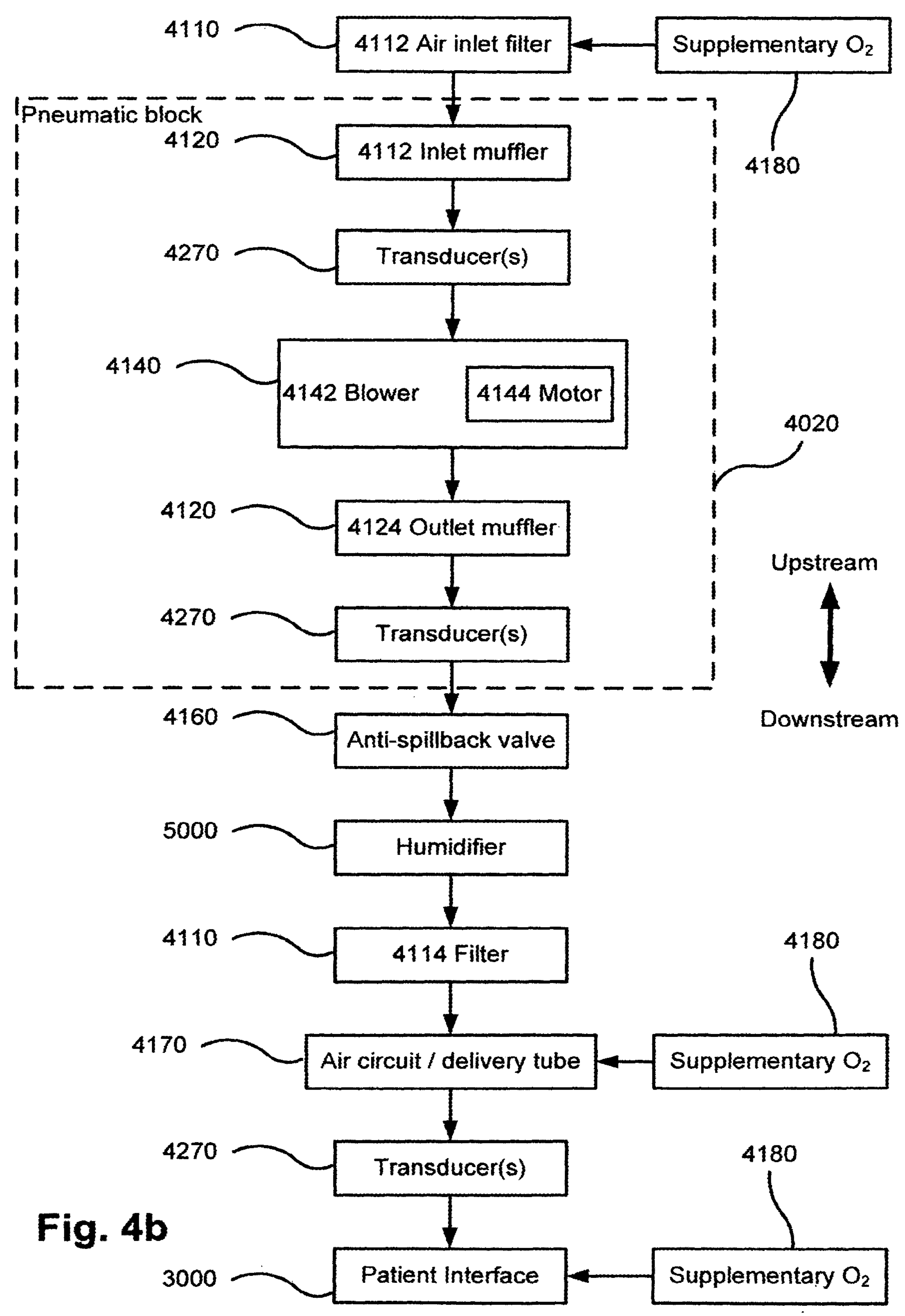

FIG. 4*b* shows a schematic diagram of the pneumatic circuit of a PAP device of FIG. 4*a*. The directions of upstream and downstream are indicated.

Figure 4C:
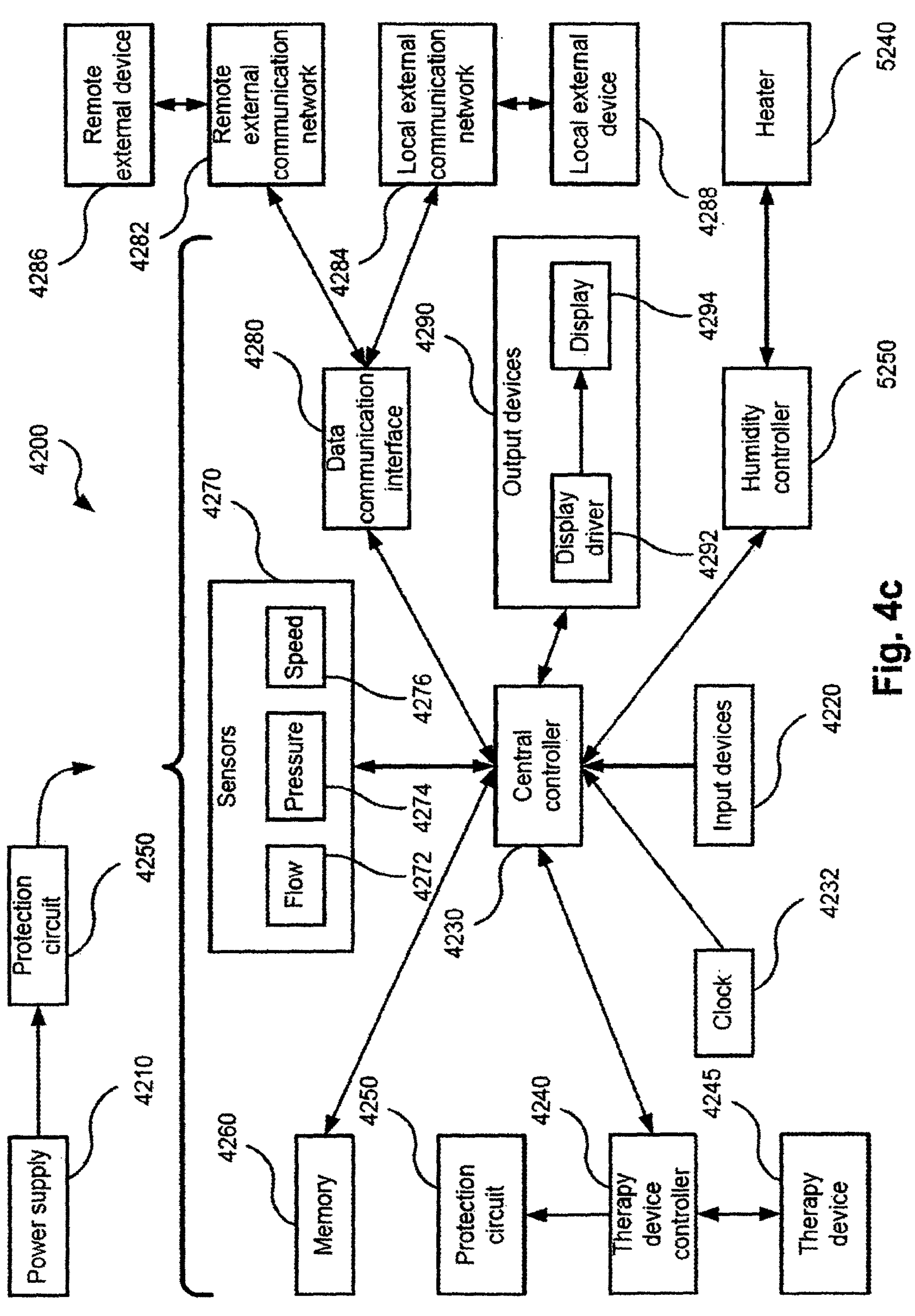

FIG. 4*c* shows a schematic diagram of the electrical components of the PAP device of FIG. 4*a*.

Figure 4D:
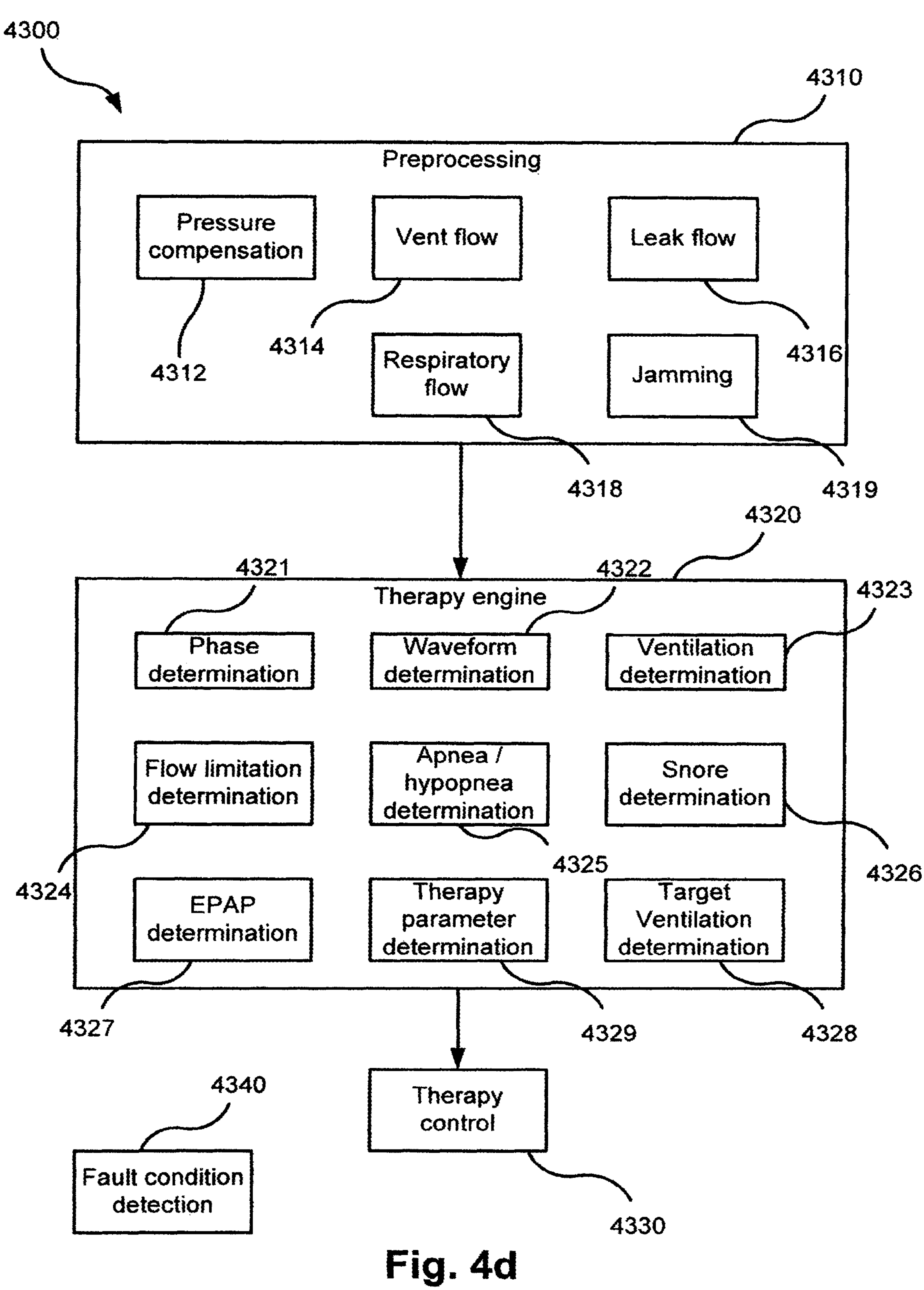

FIG. 4*d* shows a schematic diagram of the algorithms implemented in the PAP device of FIG. 4*a*. In this figure, arrows with solid lines indicate an actual flow of information, for example via an electronic signal.

Humidifier

Figure 5A:
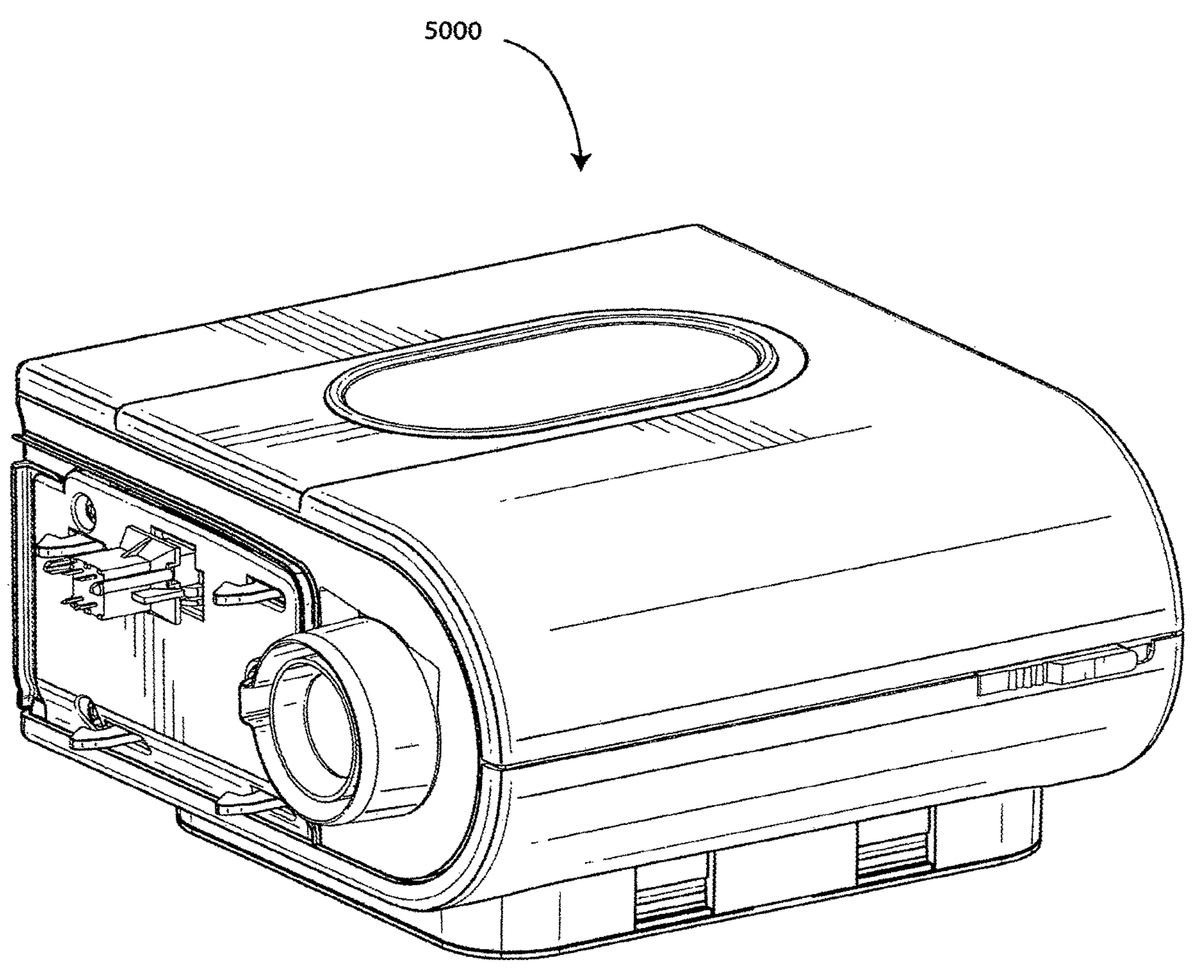

FIG. 5*a* shows a humidifier in accordance with one aspect of the present technology.

Breathing Waveforms

Figure 6A:
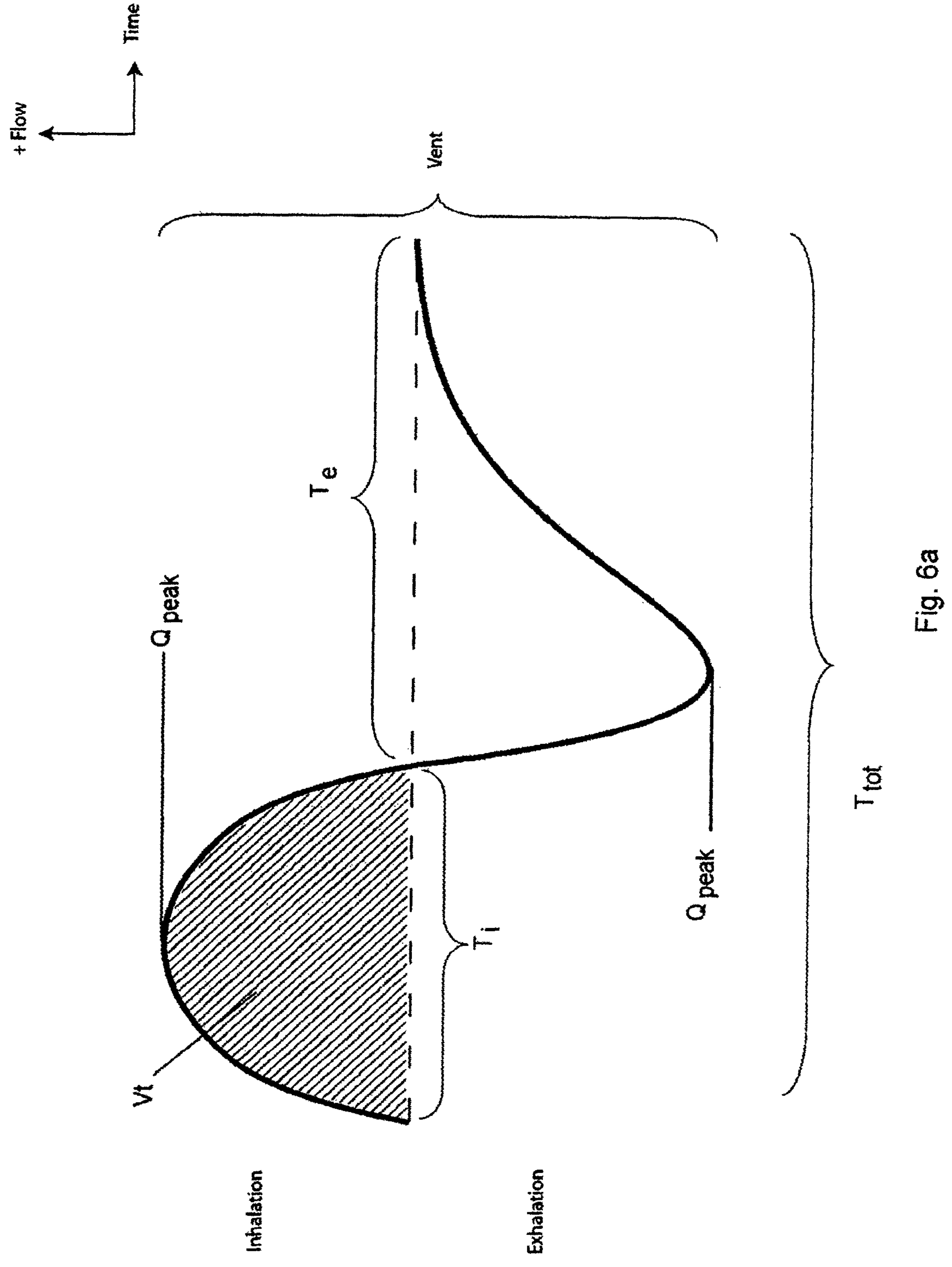

FIG. 6*a* shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a breathing rate of about 15 breaths per minute (BPM), with Ventilation, Vent, about 7.5 L/minute. A typical duty cycle, the ratio of Ti to Ttot is about 40%.

Figure 6B:
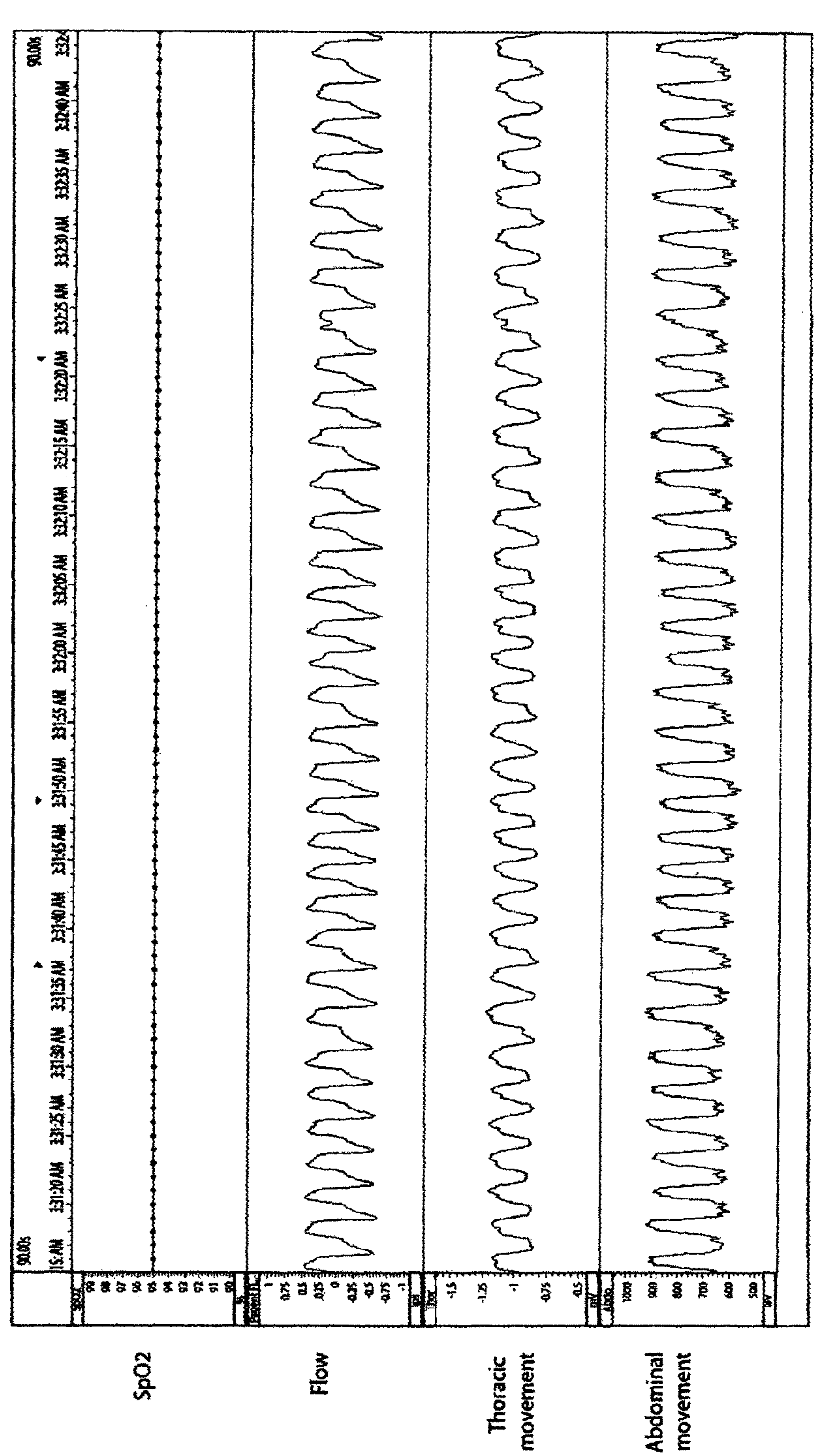

FIG. 6*b* shows a patient during non-REM sleep breathing normally over a period of about ninety seconds, with about 34 breaths, being treated with Automatic PAP, and the mask pressure being about 11 $cmH_2O$. The top channel shows oximetry ($SpO_2$), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

Figure 6C:
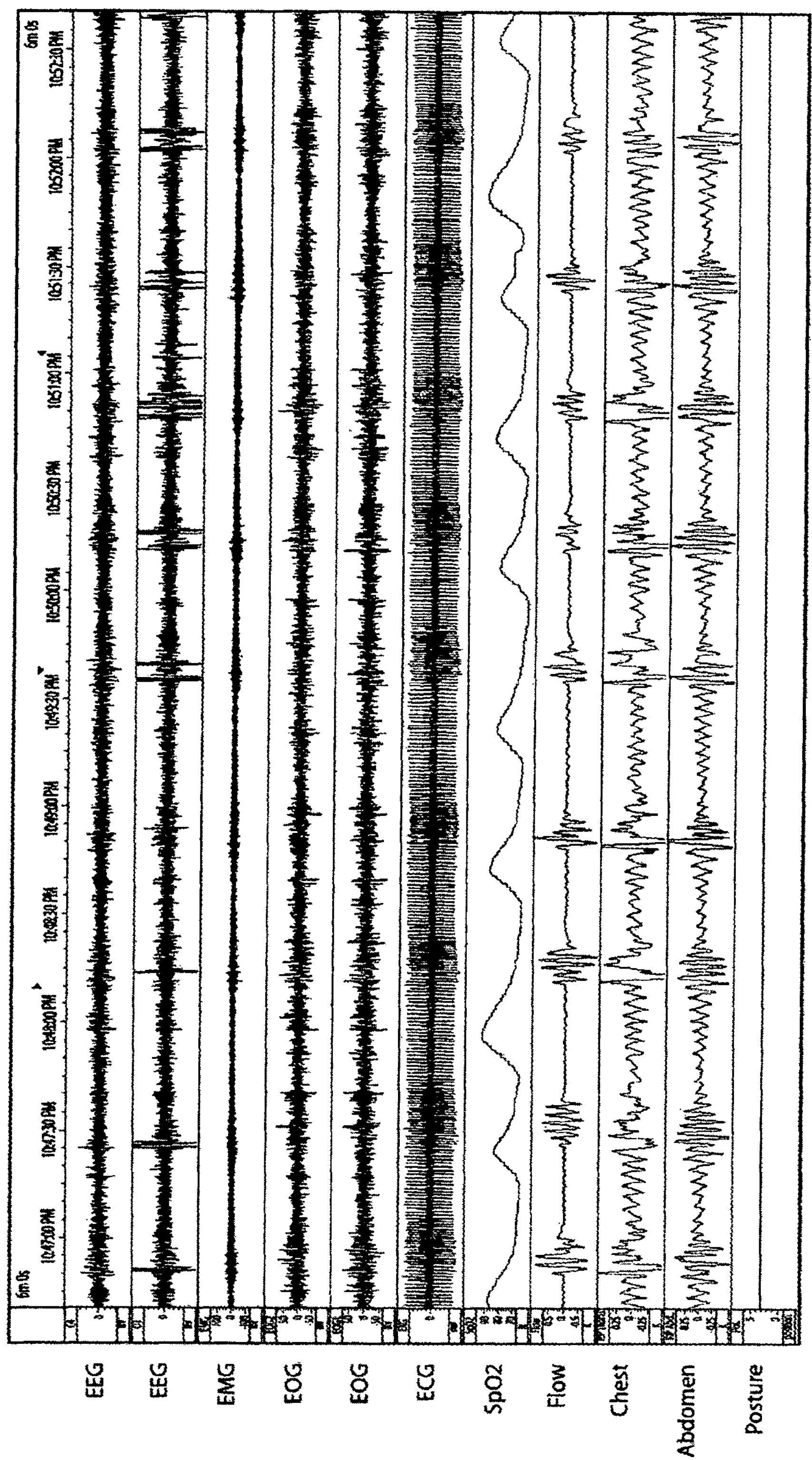

FIG. 6*c* shows polysomnography of a patient before treatment. There are eleven signal channels from top to bottom with a 6 minute horizontal span. The top two channels both are EEG (electoencephalogram) from different scalp locations. Periodic spikes in second represent cortical arousal and related activity. The third channel down is submental EMG (electromyogram). Increasing activity around time of arousals represent genioglossus recruitment. The fourth & fifth channels are EOG (electro-oculogram). The sixth channel is an electocardiogram. The seventh channel shows pulse oximetry ($SpO_2$) with repetitive desaturations to below 70% from about 90%. The eighth channel is respiratory airflow using nasal cannula connected to differential pressure transducer. Repetitive apneas of 25 to 35 seconds alternating with 10 to 15 second bursts of recovery breathing coinciding with EEG arousal and increased EMG activity. The ninth shows movement of chest and tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

Figure 6D:
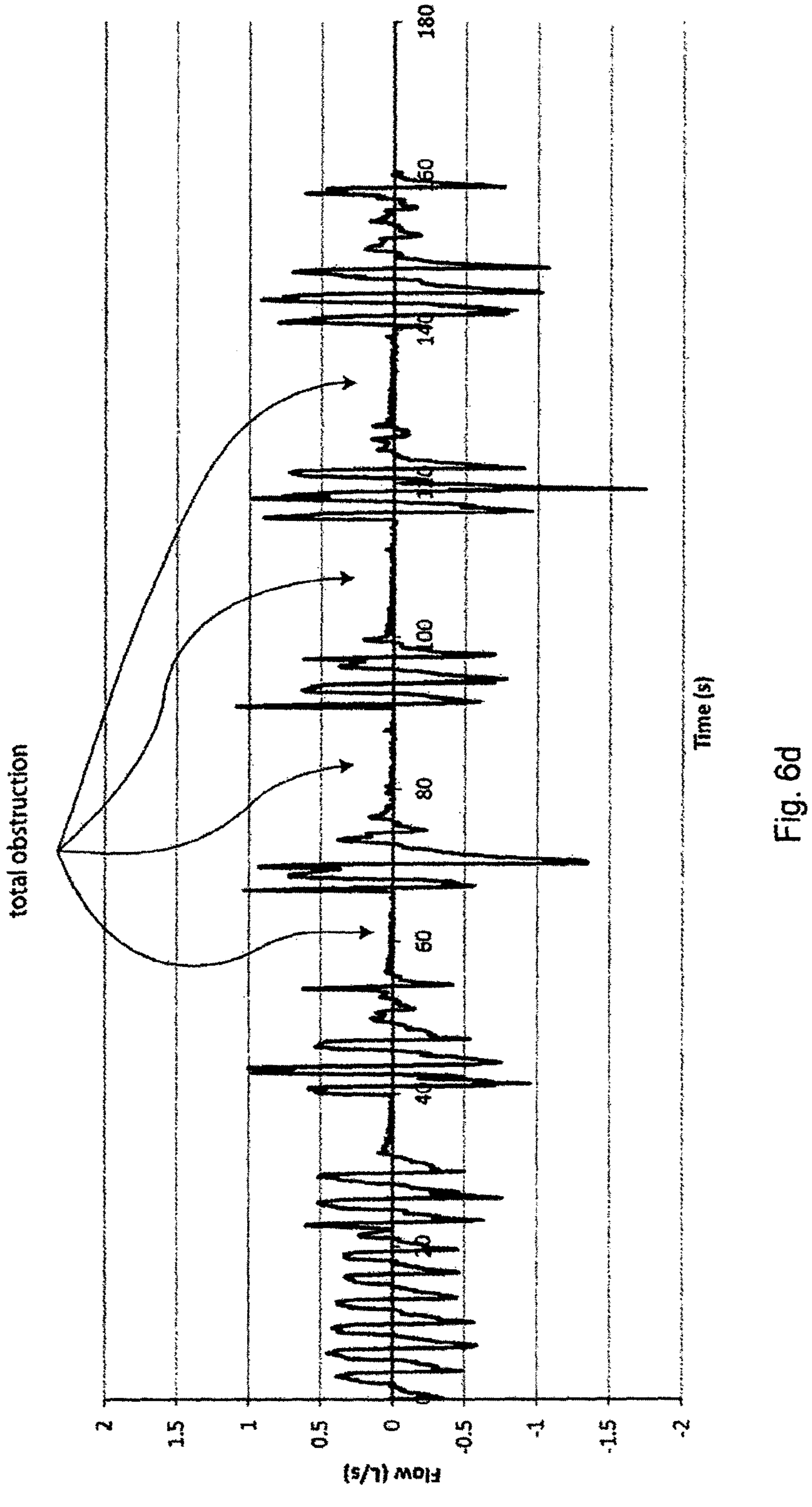

FIG. 6*d* shows patient flow data where the patient is experiencing a series of total obstructive apneas. The duration of the recording is approximately 160 seconds. Flow ranges from about +1 L/s to about −1.5 L/s. Each apnea lasts approximately 10-15 s.

Figure 6E:
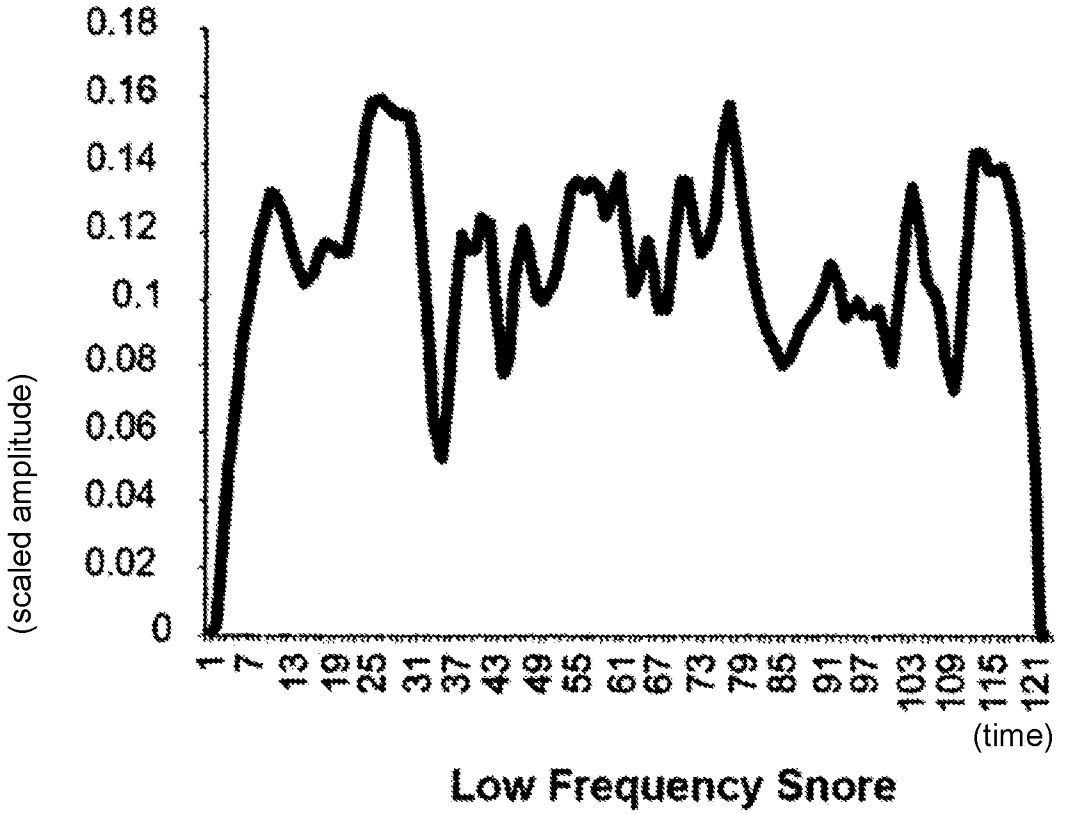

FIG. 6*e* shows a scaled inspiratory portion of a breath where the patient is experiencing low frequency inspiratory snore.

Figure 6F:
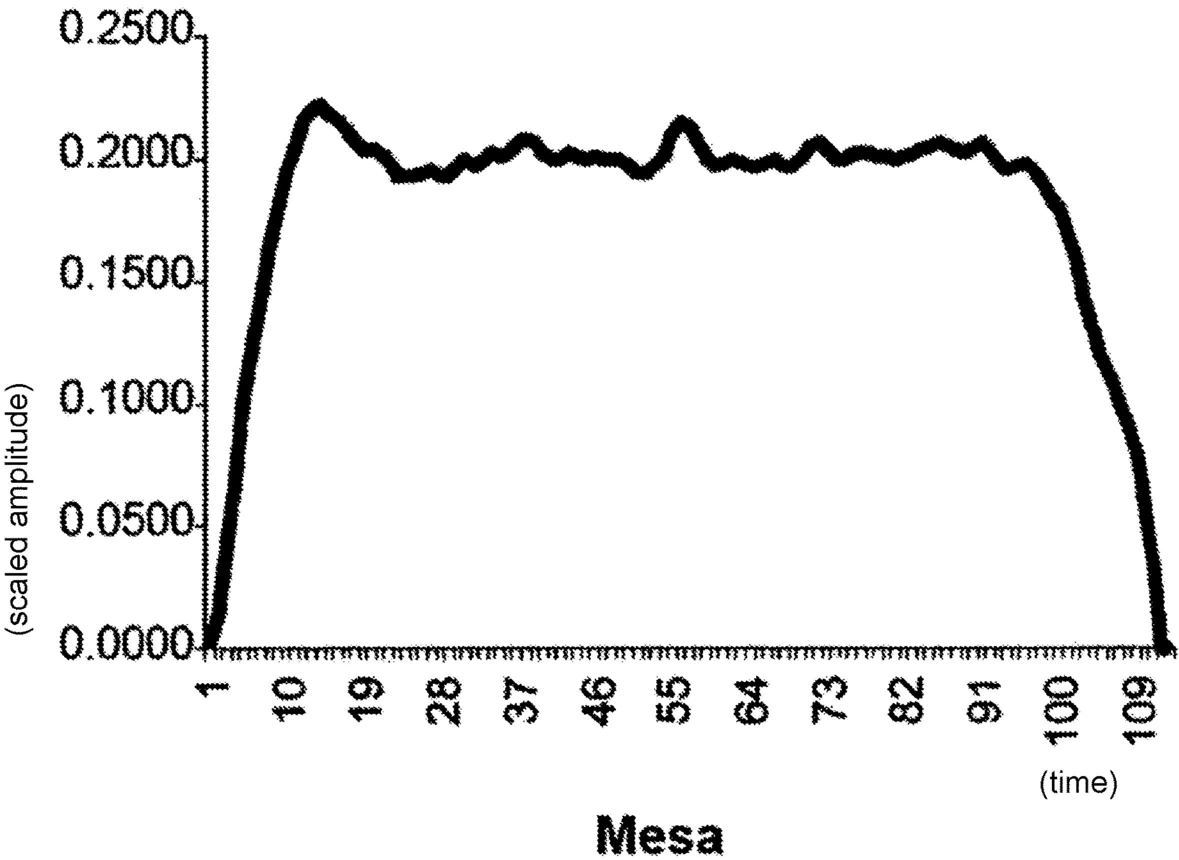

FIG. 6*f* shows a scaled inspiratory portion of a breath where the patient is experiencing an example of ordinary or "mesa" flatness inspiratory flow limitation.

Figure 6G:
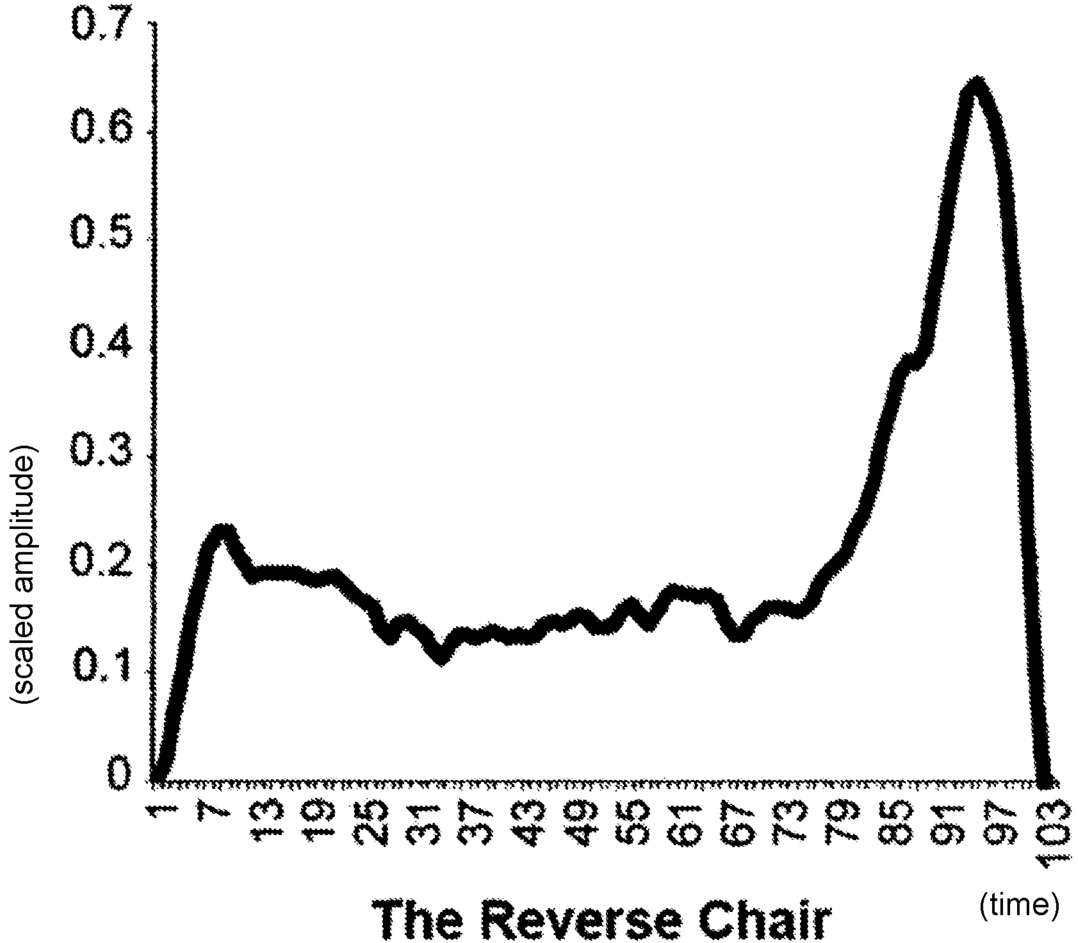

FIG. 6*g* shows a scaled inspiratory portion of a breath where the patient is experiencing an example of "reverse chair" inspiratory flow limitation.

Figure 6H:

FIG. 6*h* shows a scaled inspiratory portion of a breath where the patient is experiencing an example of "M-shaped" inspiratory flow limitation.

Figure 6I:
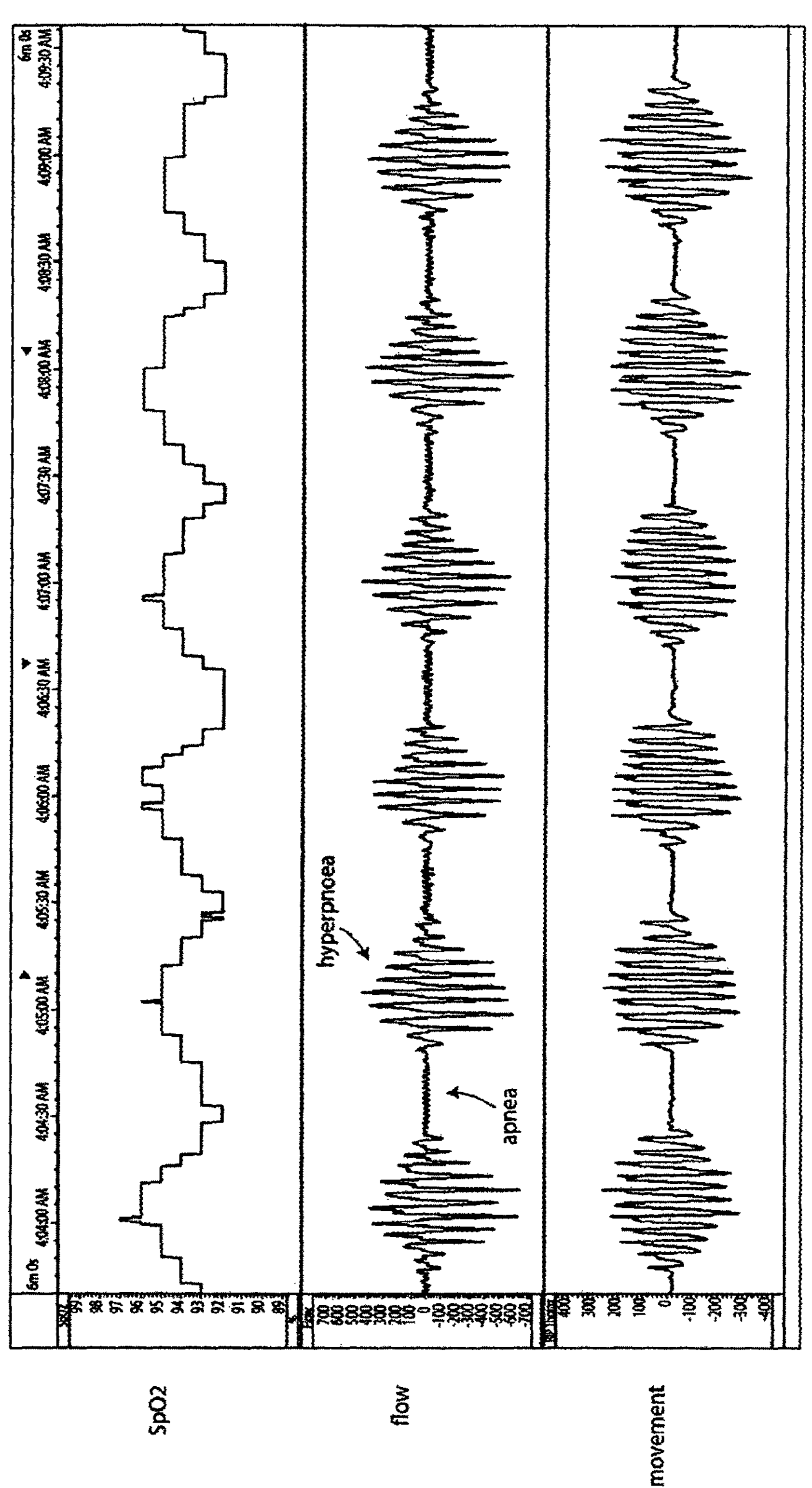

FIG. 6*i* illustrates an example of Cheyne-Stokes respiration. There are three channels: oxygen saturation ($SpO_2$), a signal indicative of flow, and movement. The data span six minutes. The signal representative of flow was measured using a pressure sensor connected to nasal cannulae. The patient exhibits apneas of about 22 seconds and hyperpneas of about 38 seconds. Higher frequency low amplitude oscillation during apnea is cardiogenic.

Figure 7A:
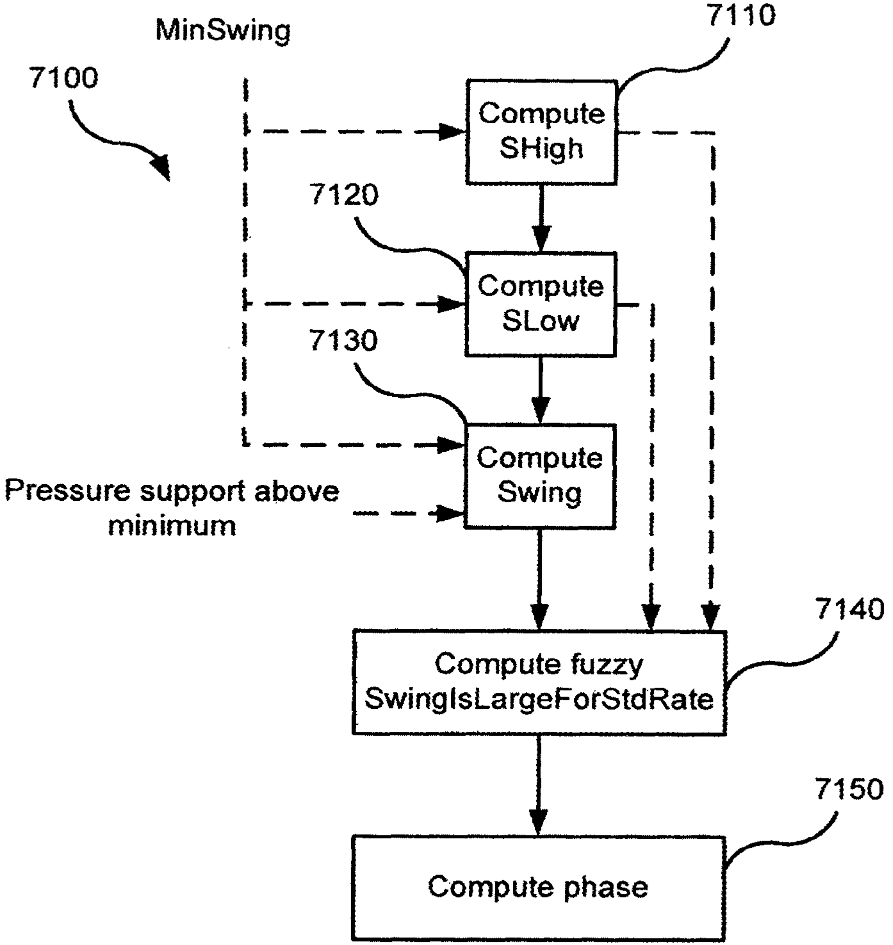
Figure 7B:
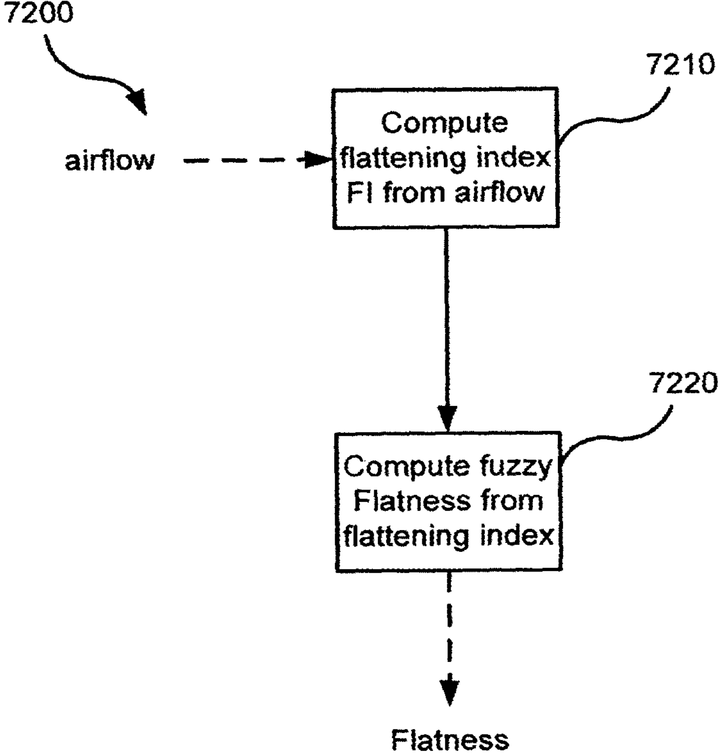
Figure 7C:
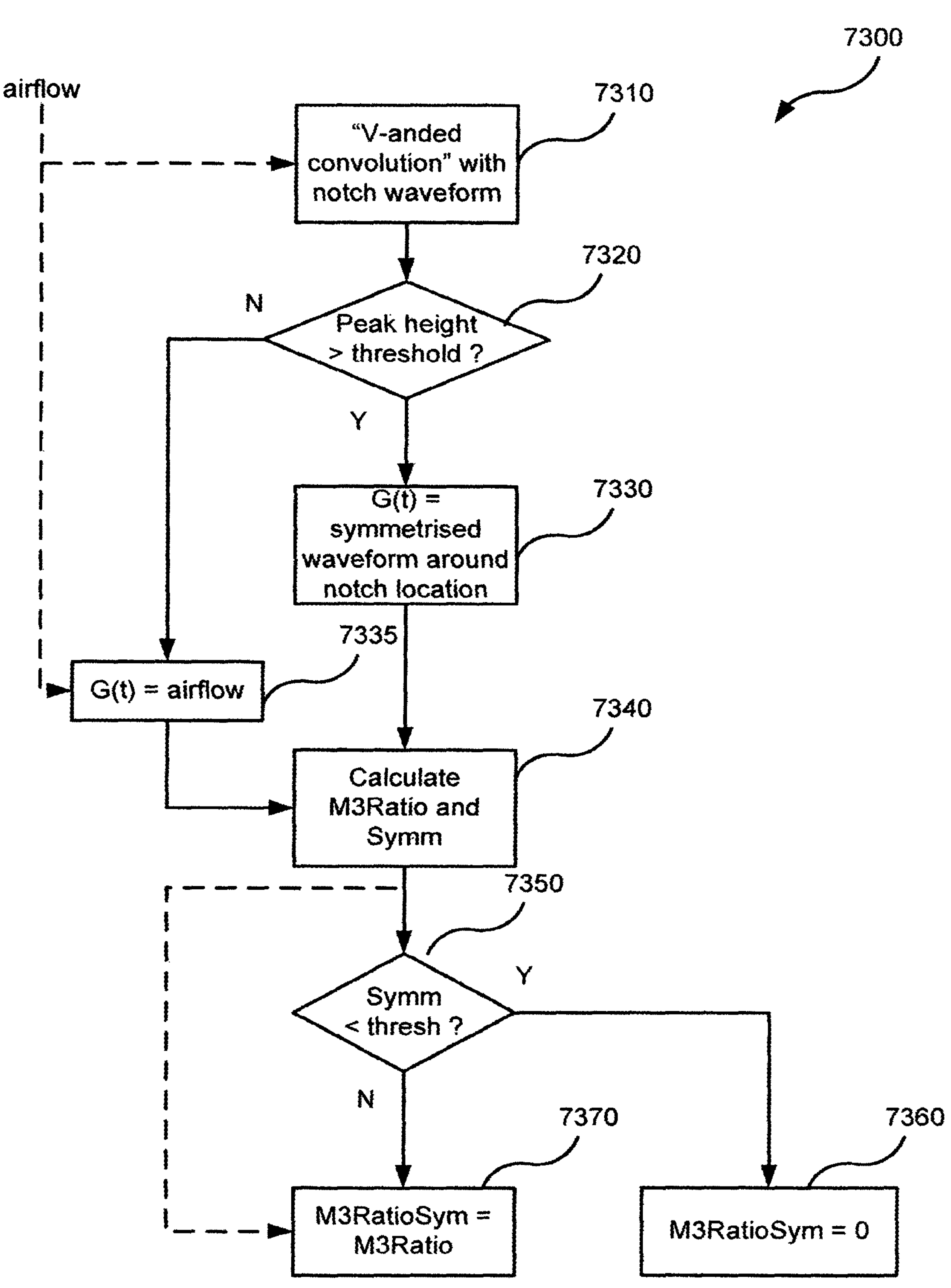
Figure 7D:
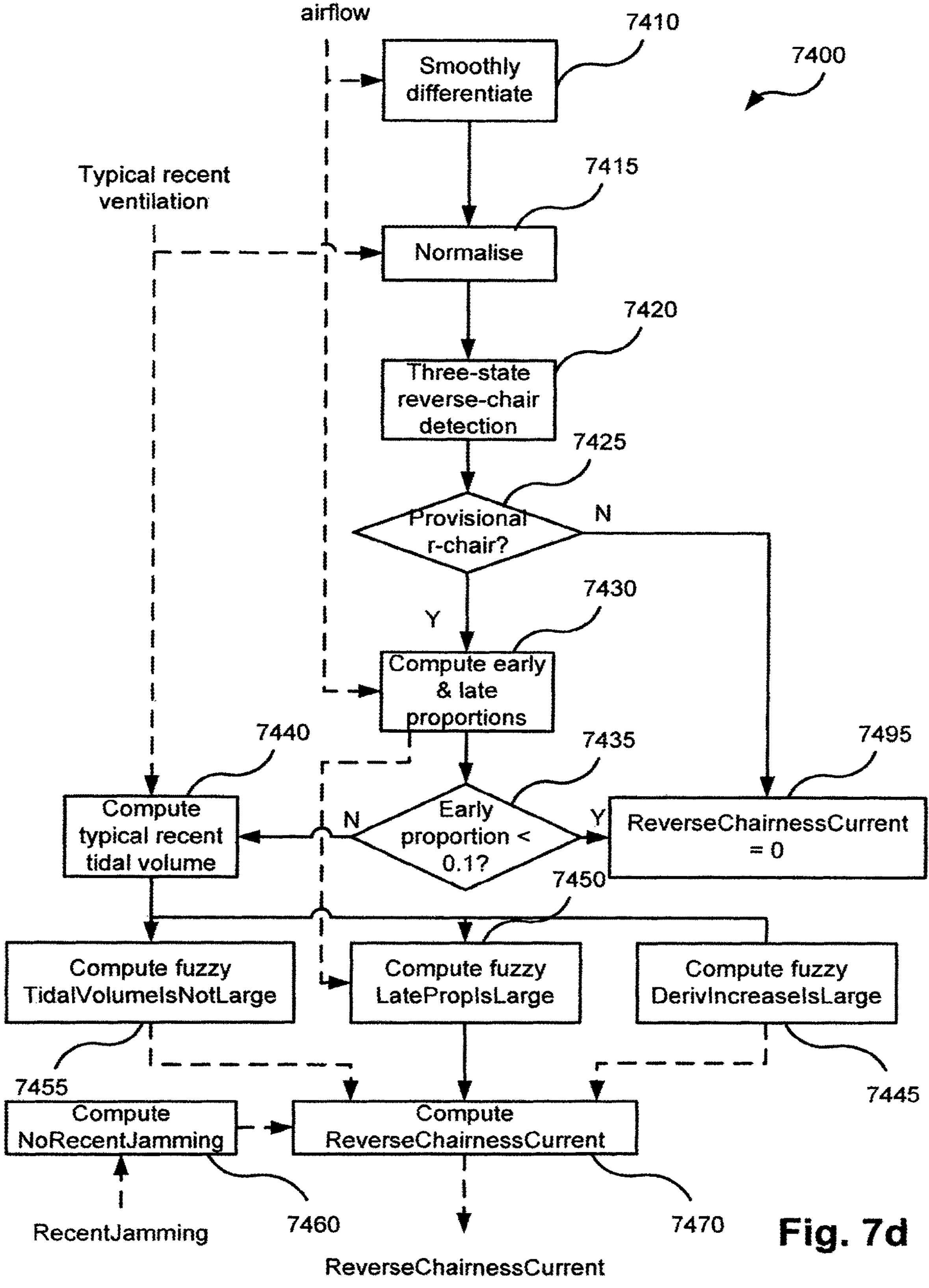
Figure 7E:
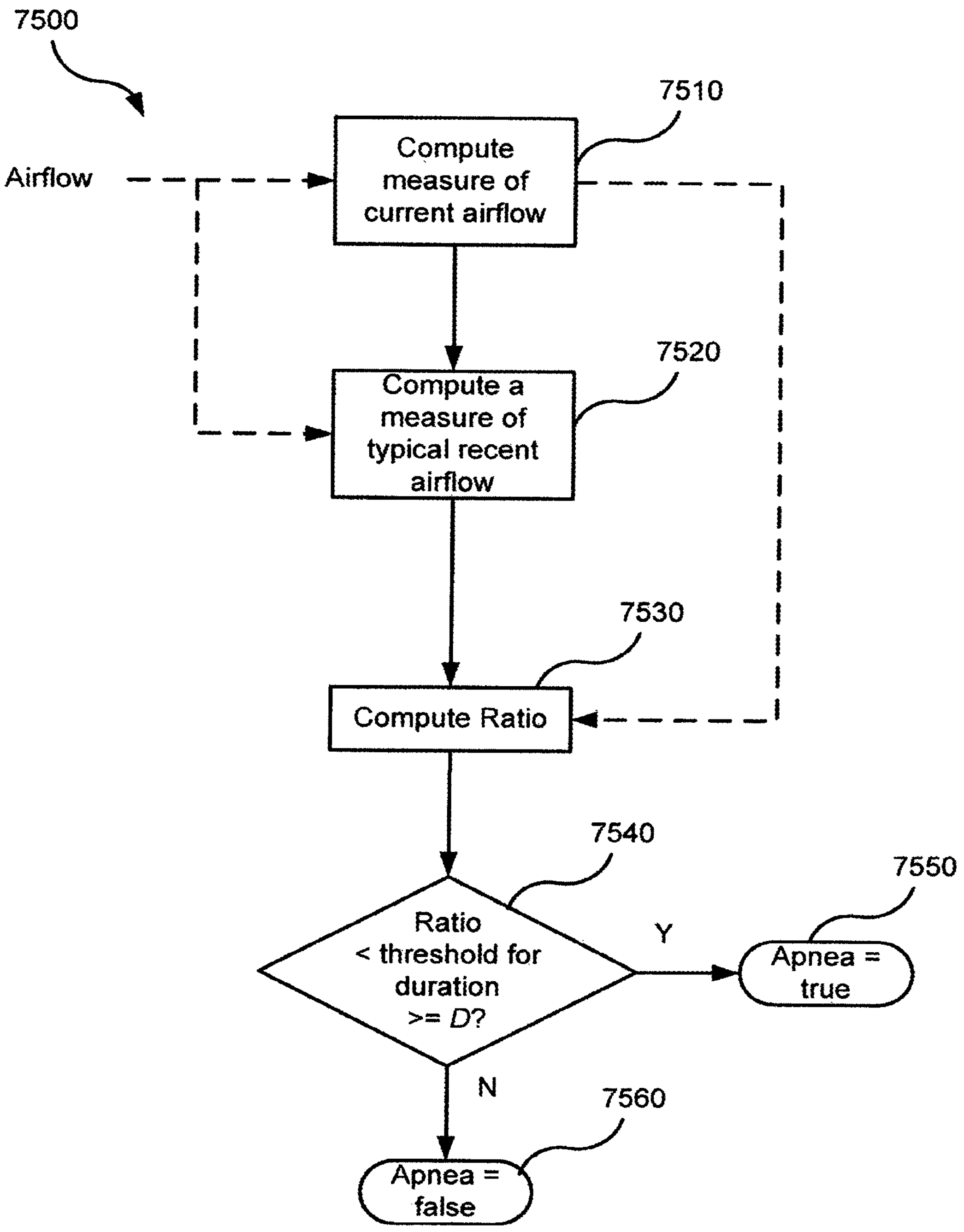
Figure 7F:
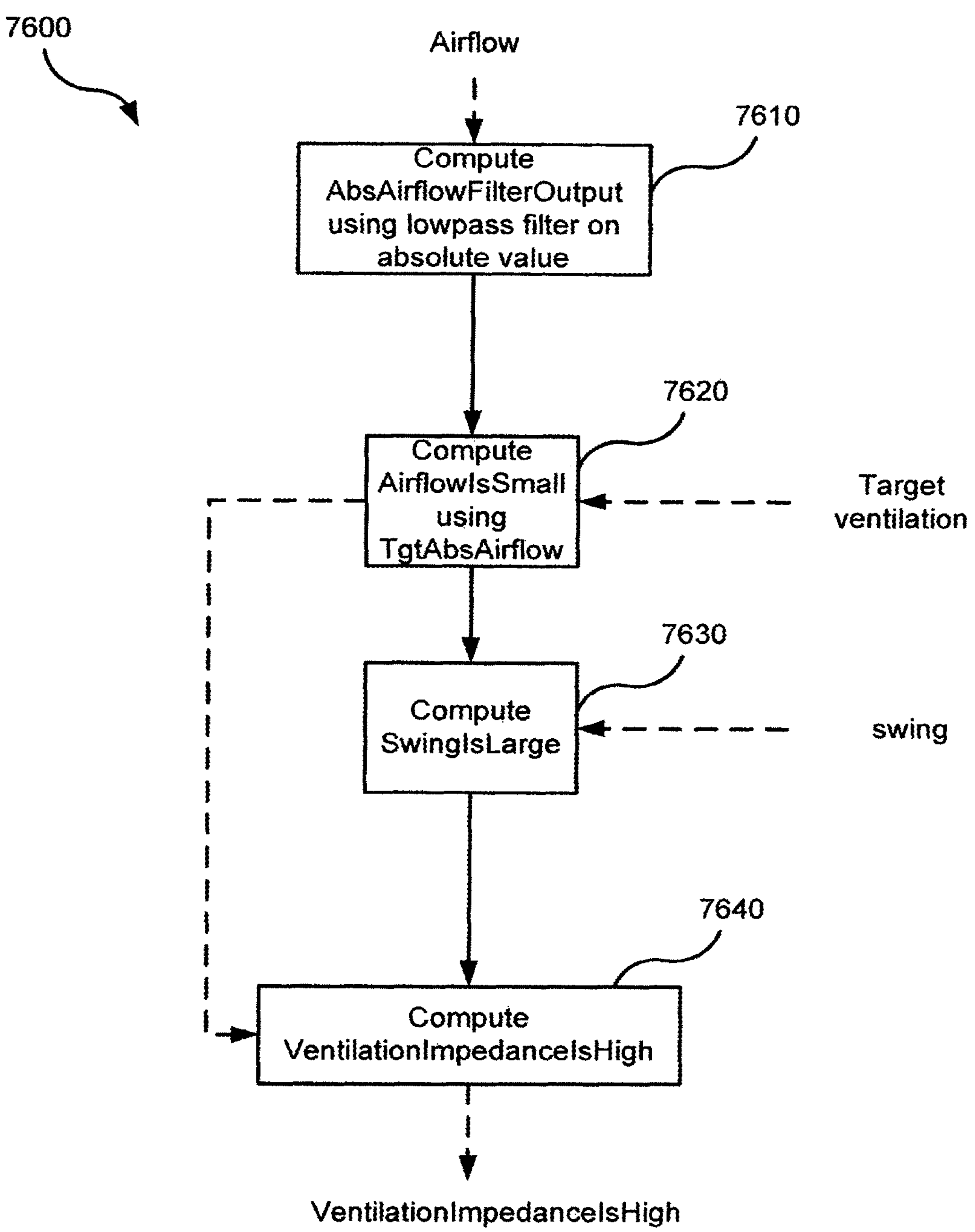
Figure 7G:
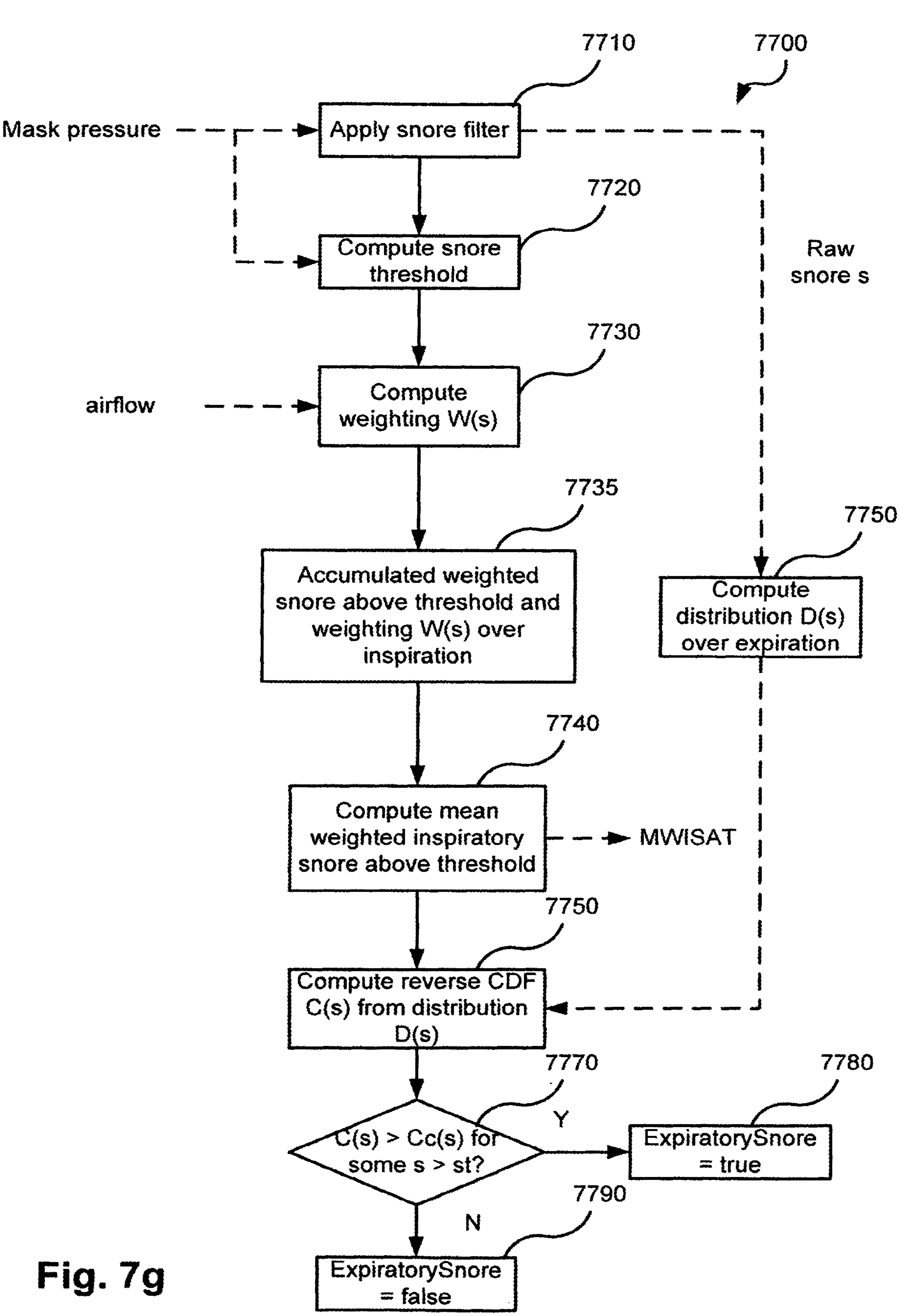
Figure 7H:
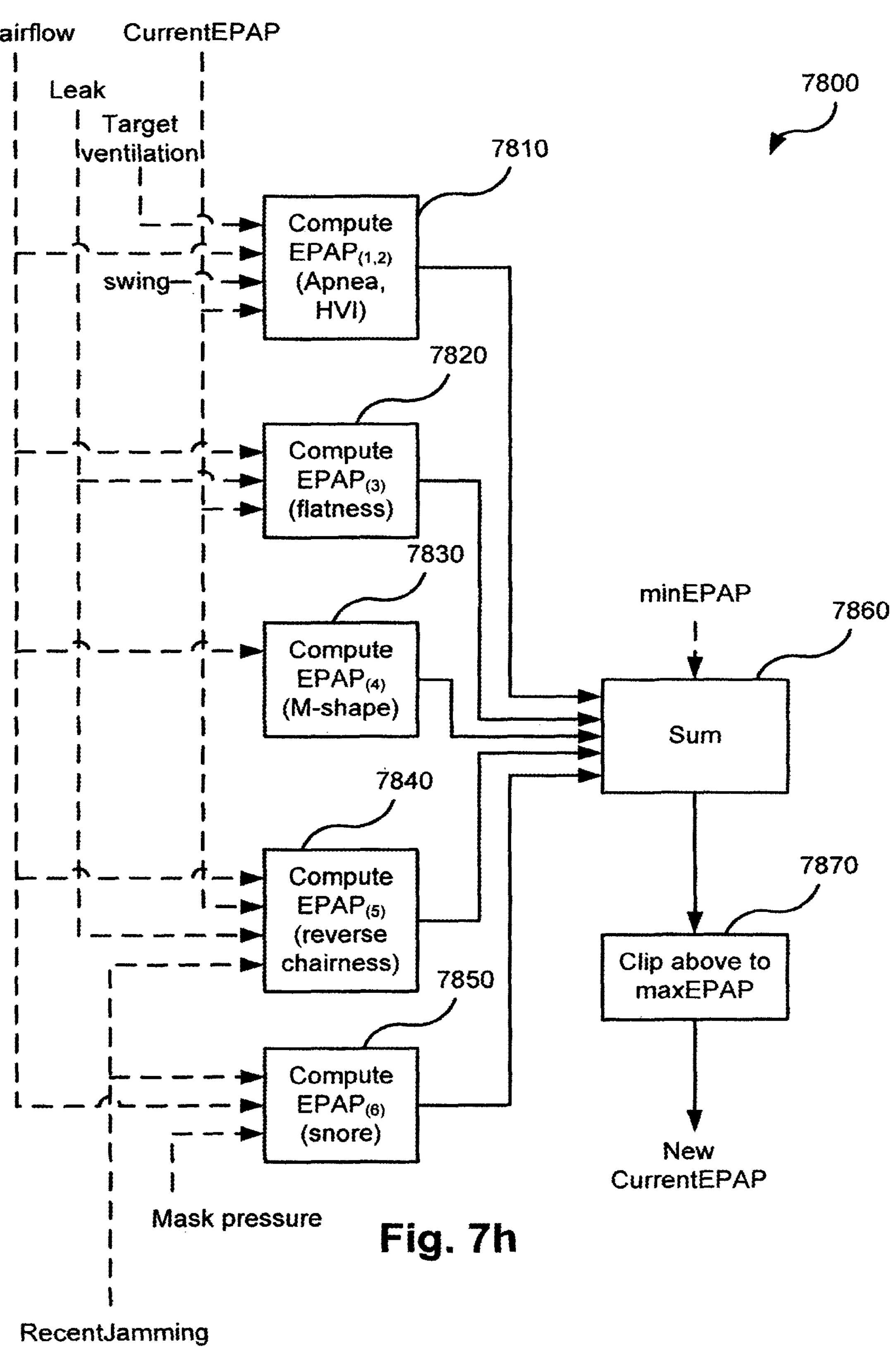
Figure 7I:
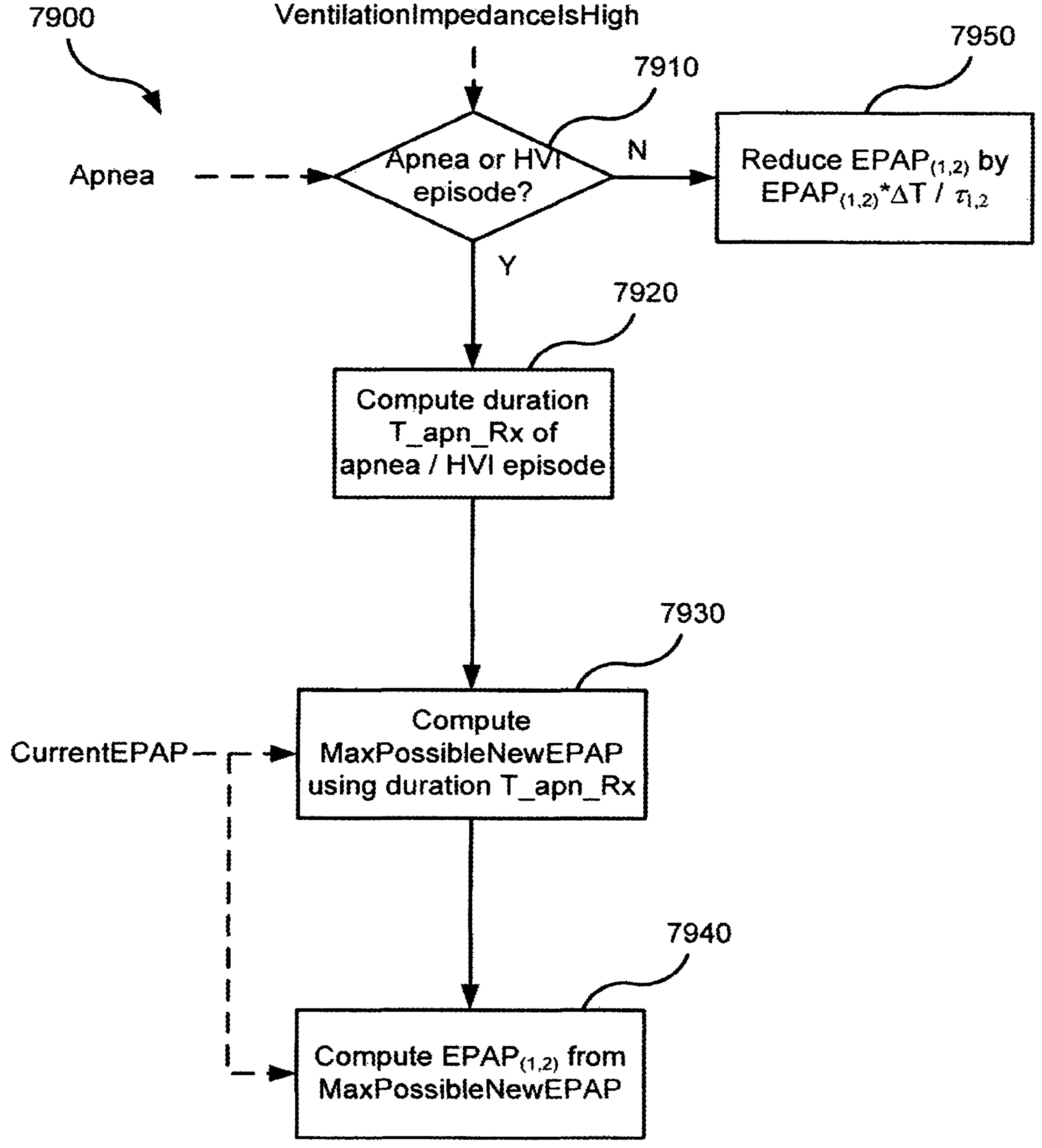
Figure 7J:
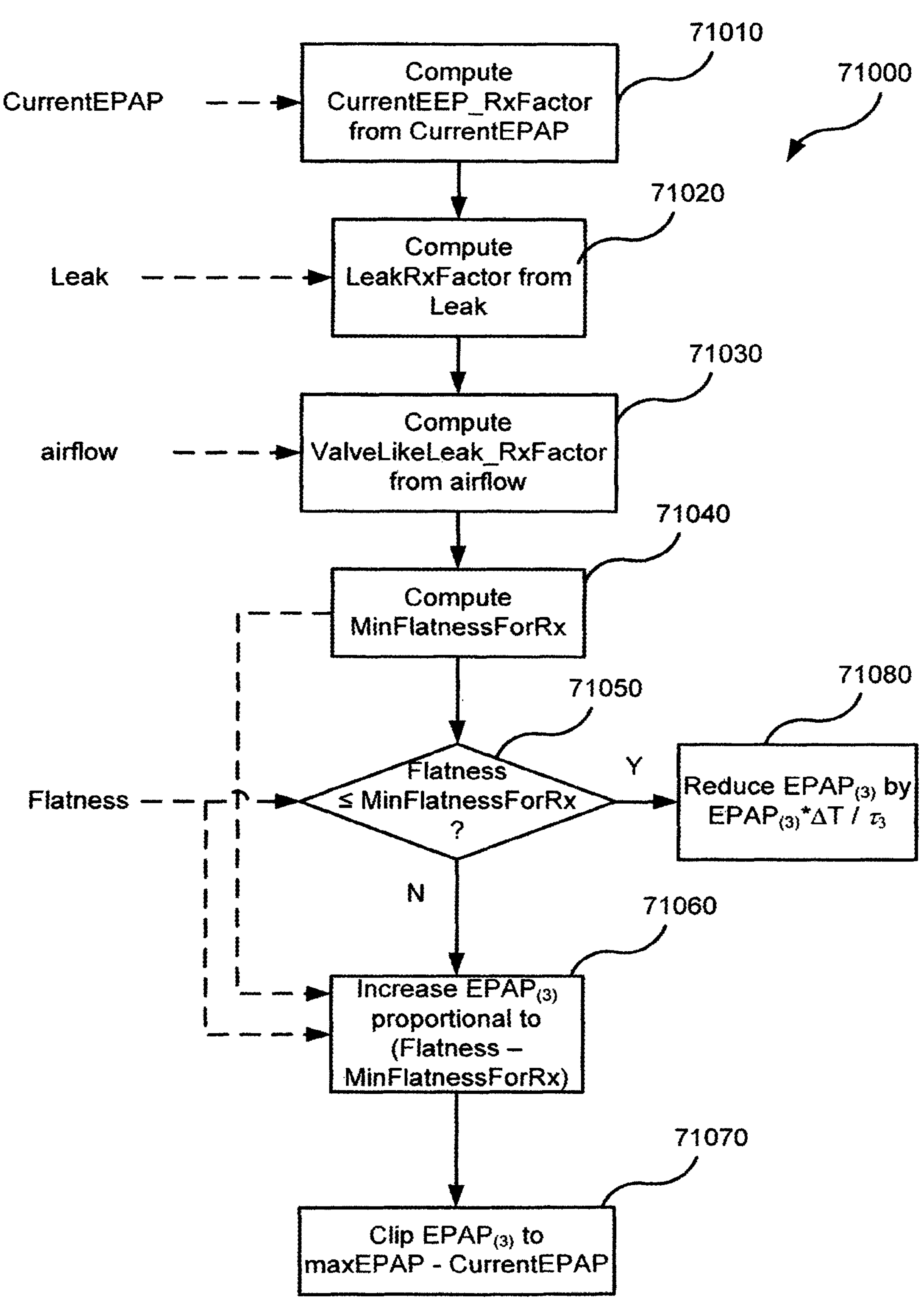
Figure 7K:
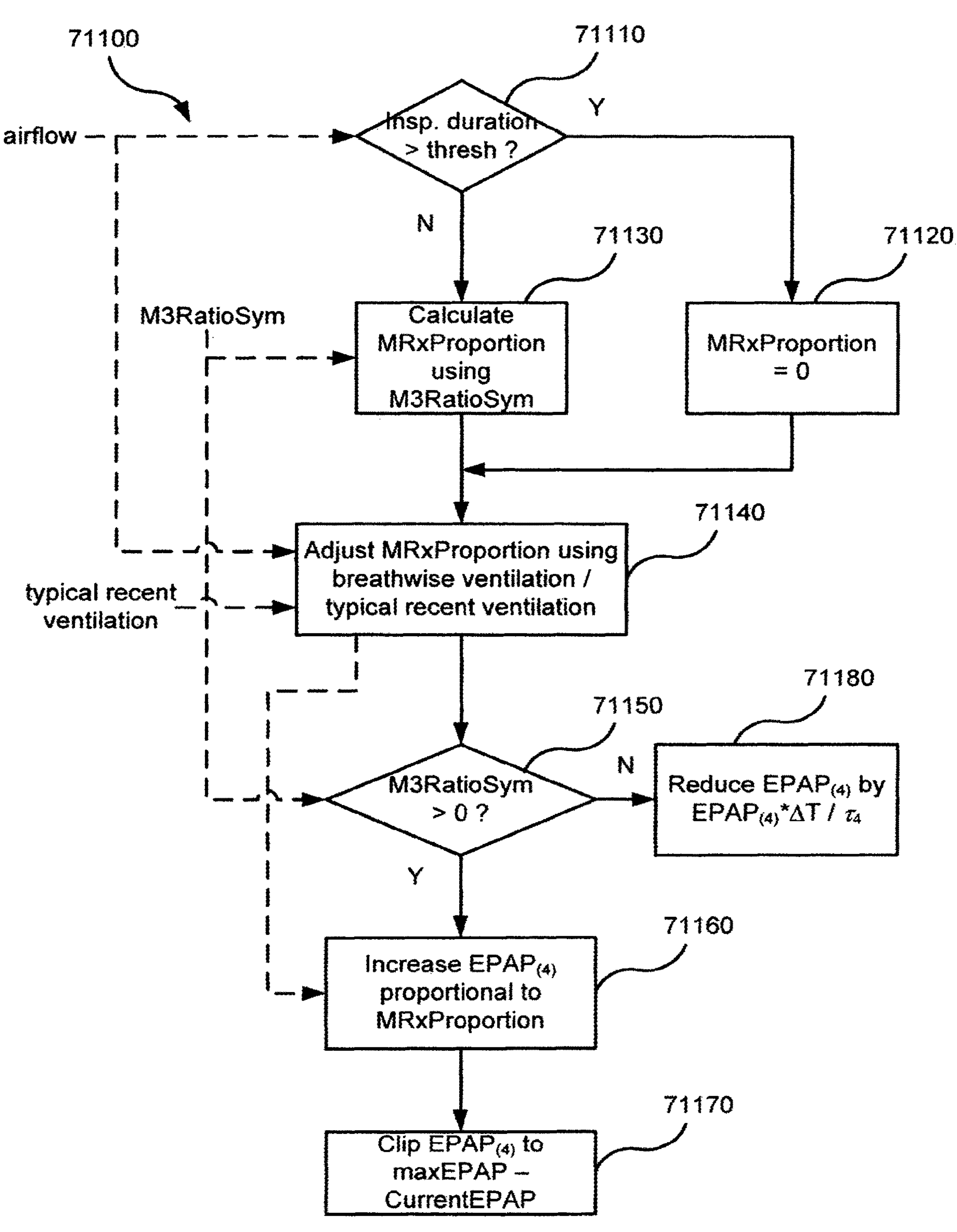
Figure 7I:
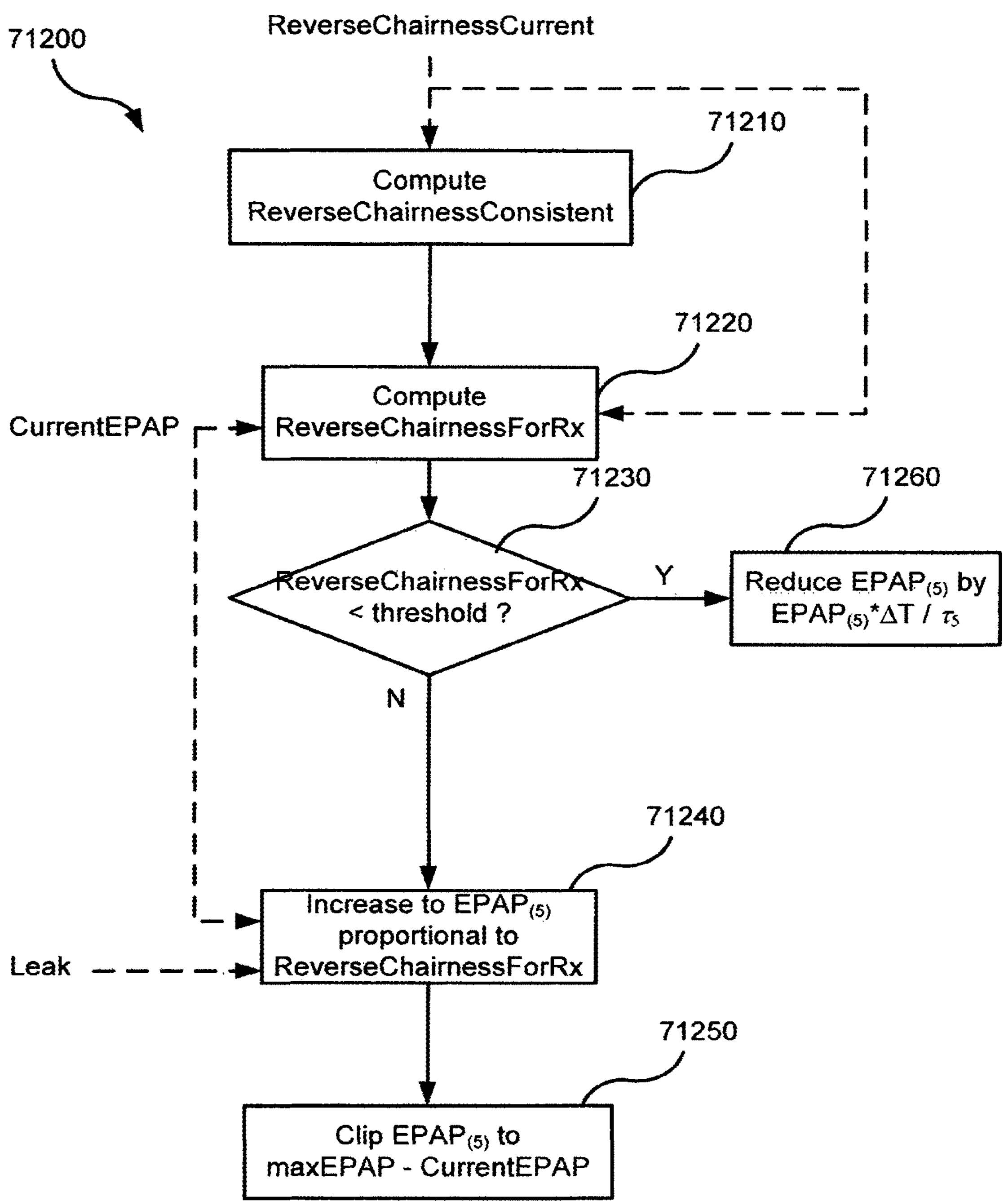
Figure 7M:
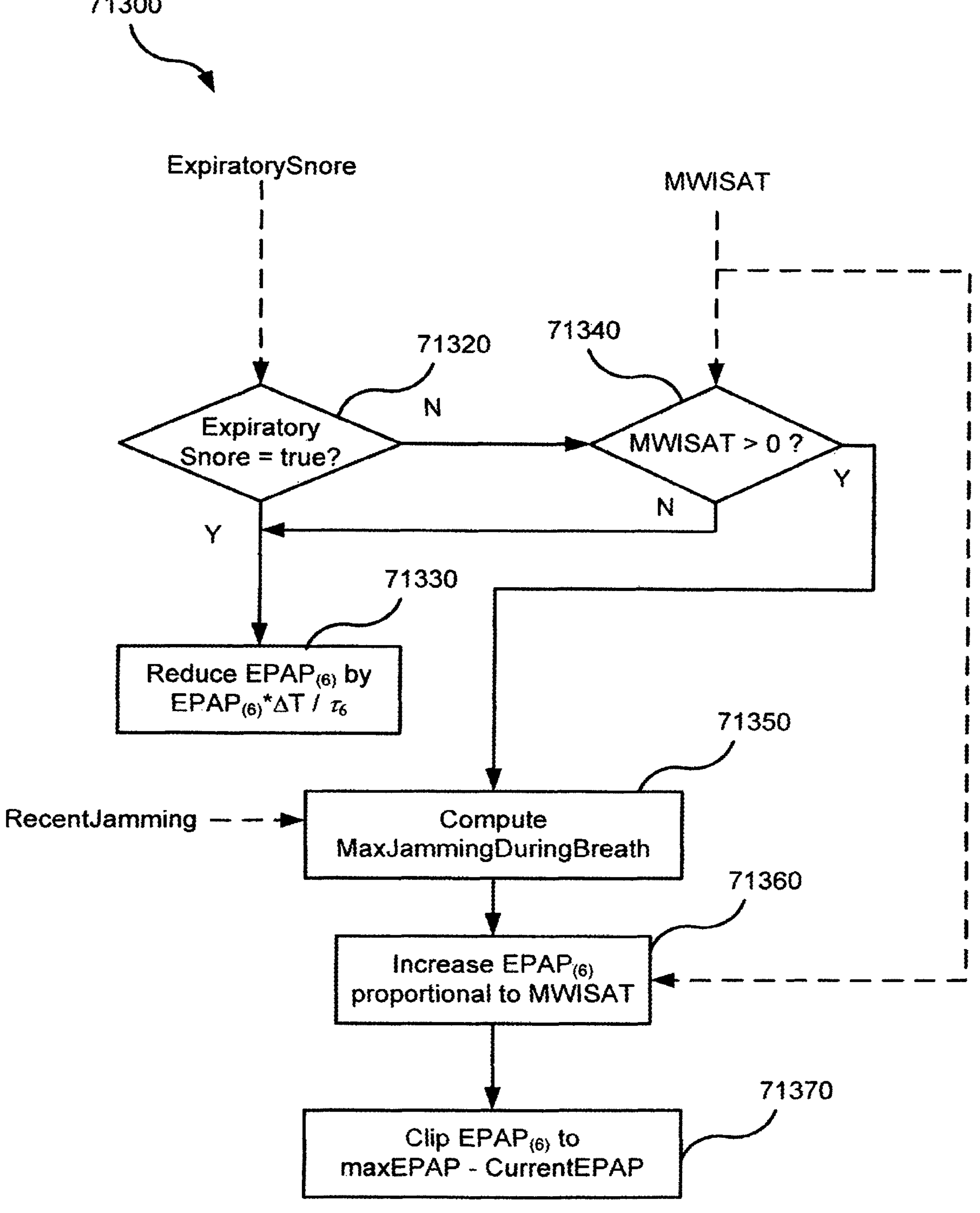
Figure 7N:
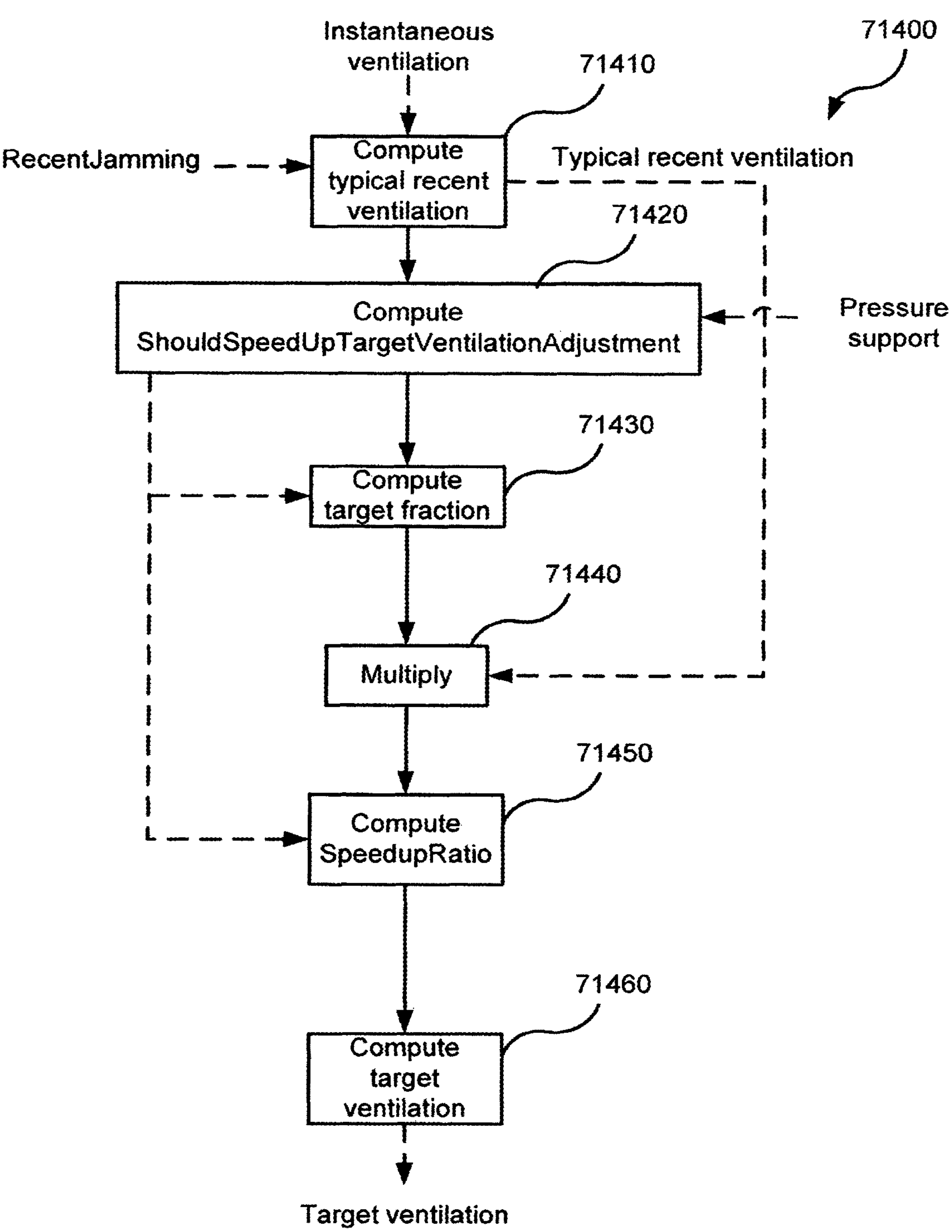
Figure 7O:
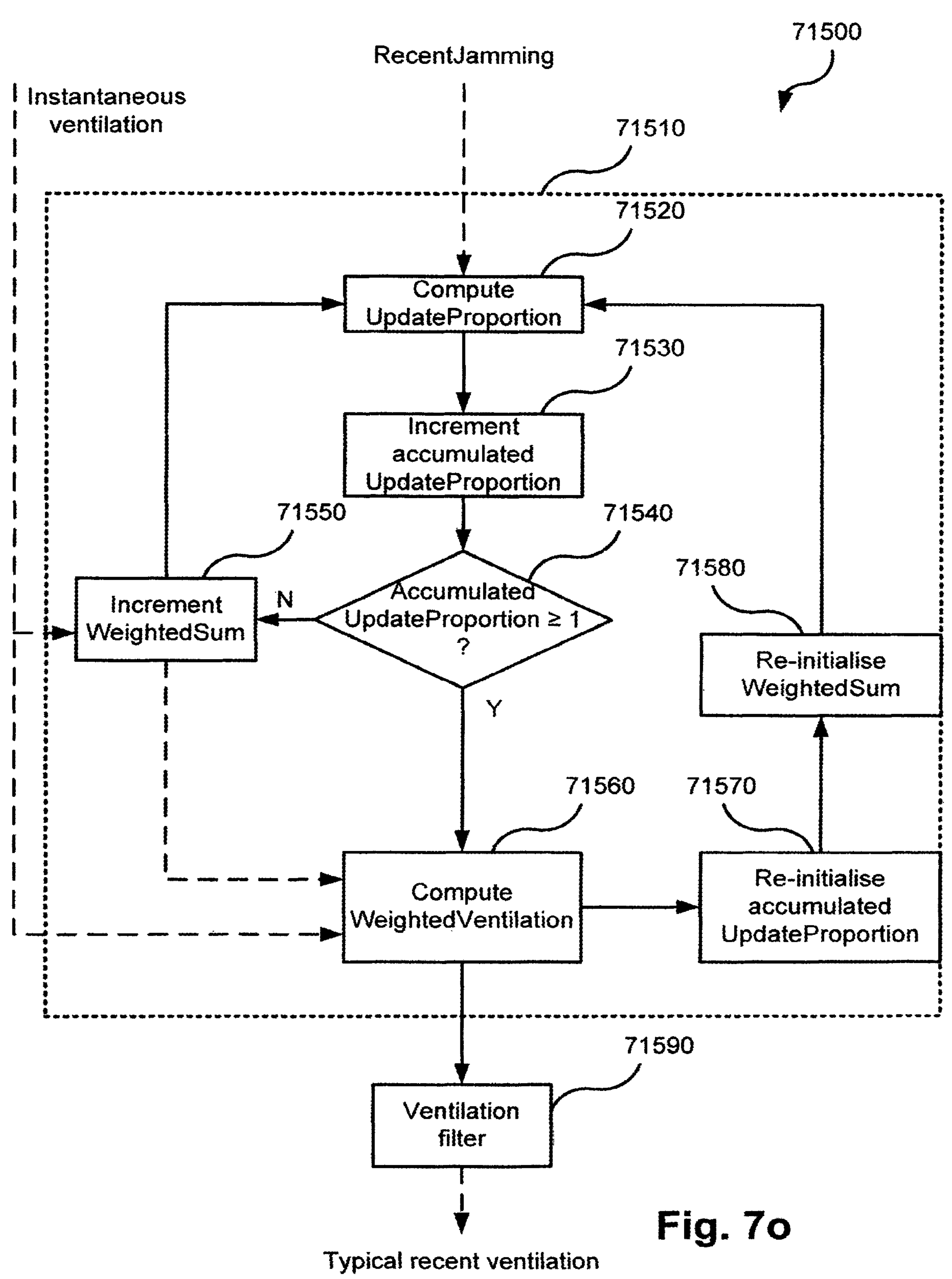
Figure 7P:
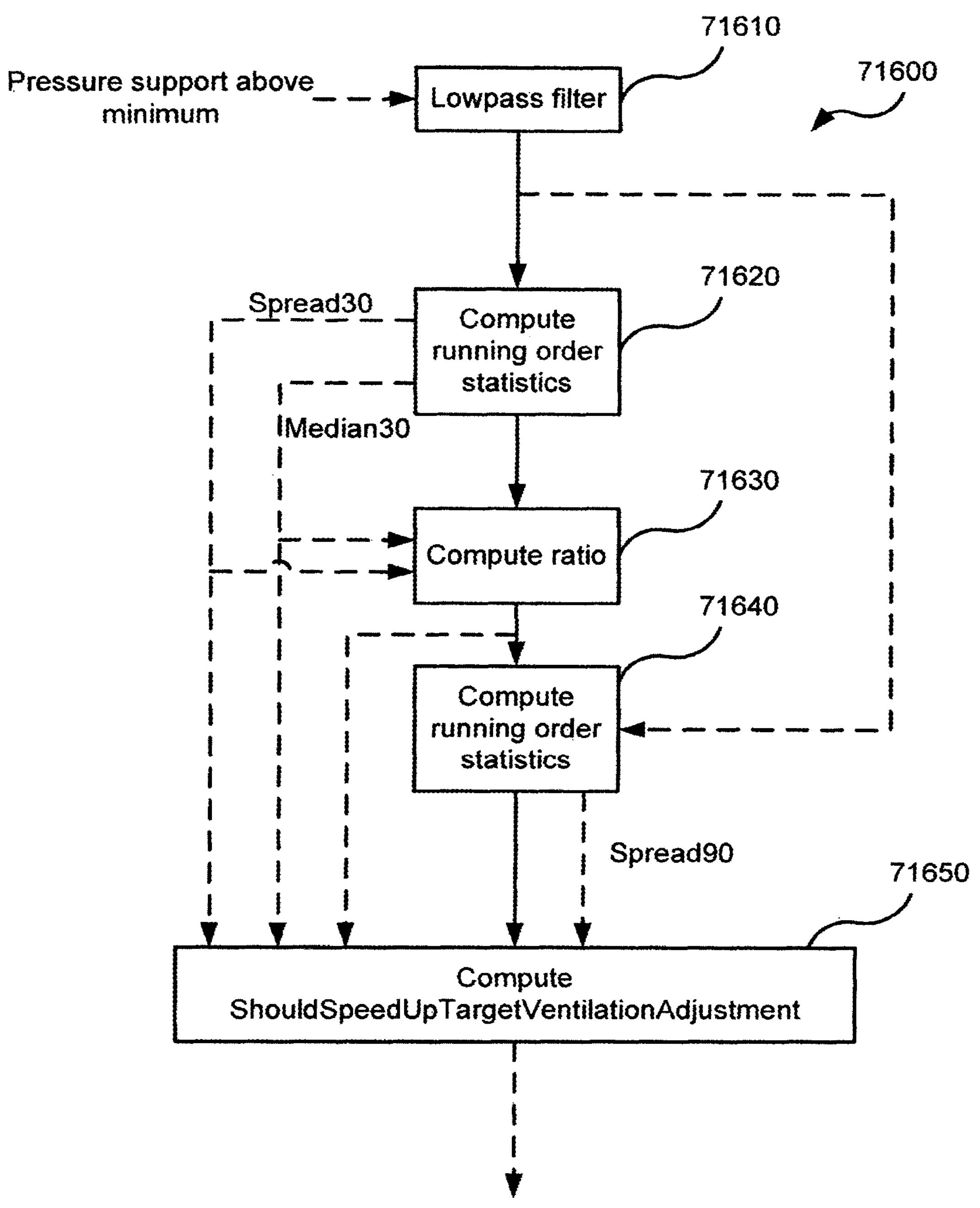
Figure 7Q:
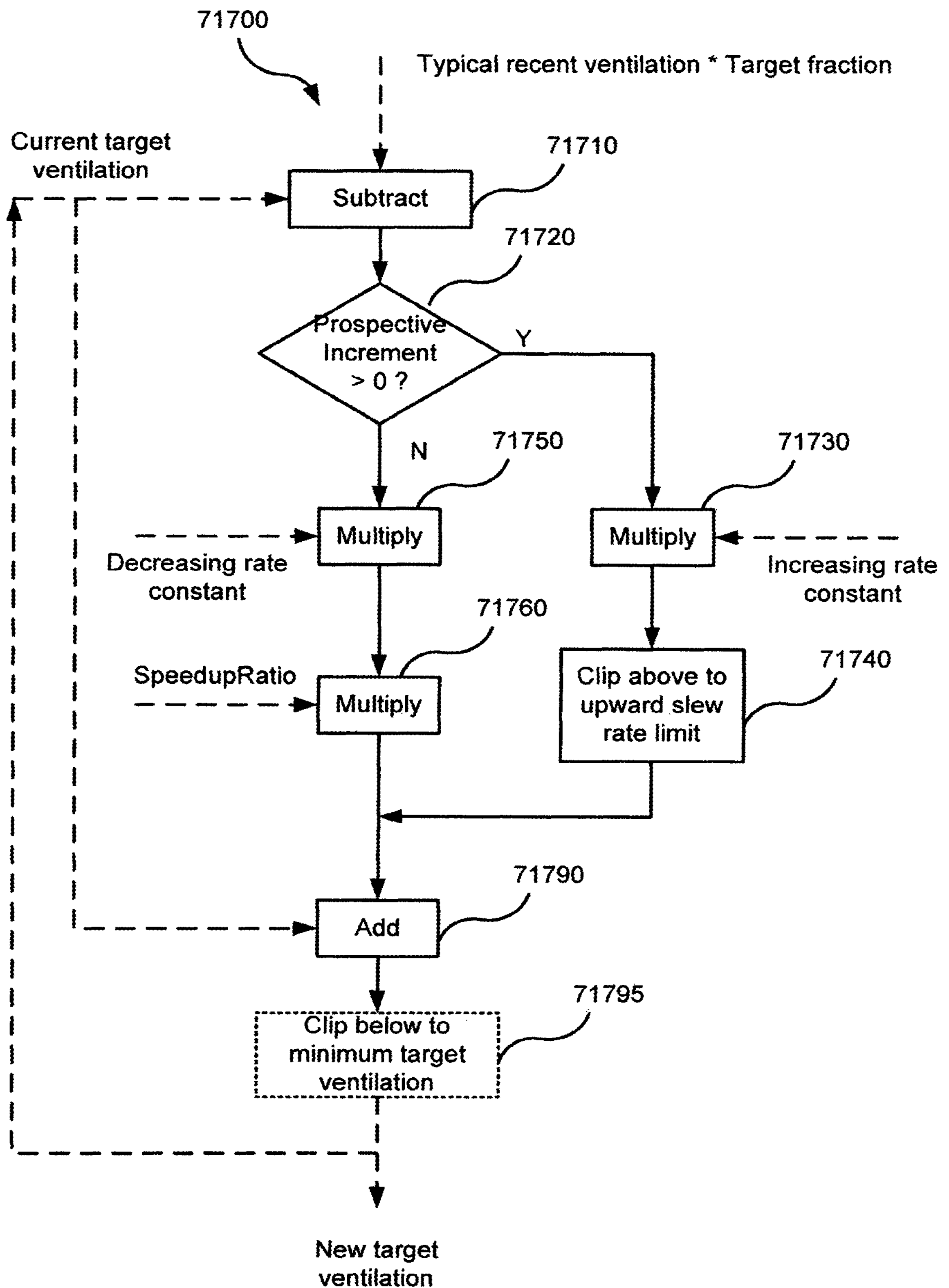

FIGS. 7*a* to 7*q* are flow charts illustrating the operation of the algorithms of FIG. 4*d* in one form of the PAP device of FIG. 4*a*.

Figure 8:
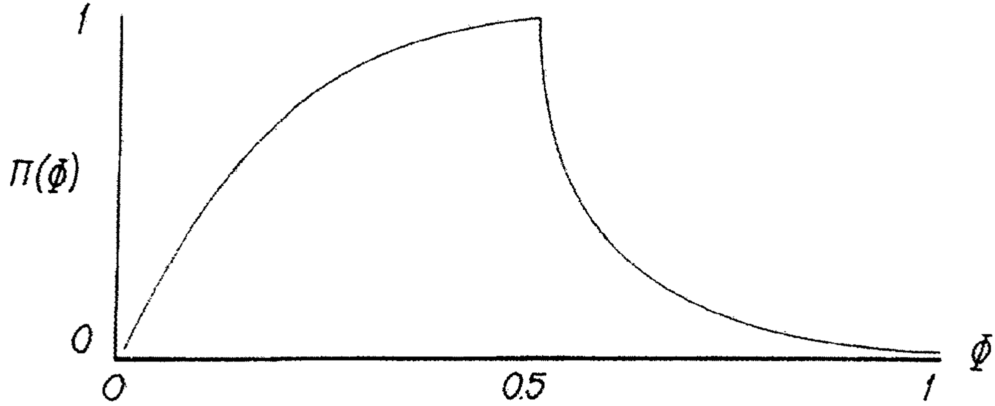

FIG. 8 illustrates an example "smooth and comfortable" treatment pressure waveform as a function of phase in accordance with one form of the present technology.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3000.

Therapy

In one form, the present technology comprises a method for treating a respiratory disorder comprising the step of applying positive pressure to the entrance of the airways of a patient 1000.

Nasal CPAP for OSA

In one form, the present technology comprises a method of treating Obstructive Sleep Apnea in a patient by applying nasal continuous positive airway pressure to the patient.

In certain embodiments of the present technology, a supply of air at positive pressure is provided to the nasal passages of the patient via one or both nares.

Patient Interface 3000

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

PAP Device 4000

A PAP device 4000 in accordance with one aspect of the present technology comprises mechanical and pneumatic components 4100, electrical components 4200 and is programmed to execute one or more algorithms 4300. The PAP device has an external housing 4010 formed in two parts, an upper portion 4012 of the external housing 4010, and a lower portion 4014 of the external housing 4010. In alternative forms, the external housing 4010 may include one or more panel(s) 4015. The PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 comprises an inlet air filter 4112, an inlet muffler 4122, a controllable pressure device 4140 capable of supplying air at positive pressure (preferably a blower 4142), and an outlet muffler 4124. One or more pressure sensors 4272 and flow sensors 4274 are included in the pneumatic path.

The pneumatic block 4020 comprises a portion of the pneumatic path that is located within the external housing 4010.

The PAP device 4000 has an electrical power supply 4210, one or more input devices 4220, a central controller 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 is programmed to execute one or more algorithm modules 4300, including in one implementation a pre-processing module 4310, a therapy engine module 4320, a pressure control module 4330, and a fault condition module 4340.

In what follows, the PAP device 4000 is referred to interchangeably as a ventilator.

PAP Device Mechanical & Pneumatic Components 4100

Air Filter(s) 4110

A PAP device in accordance with one form of the present technology may include an air filter 4110, or a plurality of air filters 4110.

In one form, an inlet air filter 4112 is located at the beginning of the pneumatic path upstream of a blower 4142. See FIG. 4*b*.

In one form, an outlet air filter 4114, for example an antibacterial filter, is located between an outlet of the pneumatic block 4020 and a patient interface 3000. See FIG. 4*b*.

Muffler(s) 4120

In one form of the present technology, an inlet muffler 4122 is located in the pneumatic path upstream of a blower 4142. See FIG. 4*b*.

In one form of the present technology, an outlet muffler 4124 is located in the pneumatic path between the blower 4142 and a patient interface 3000. See FIG. 4*b*.

Pressure Device 4140

In one form of the present technology, a pressure device 4140 for producing a flow of air at positive pressure is a controllable blower 4142. For example, the blower may include a brushless DC motor 4144 with one or more impellers housed in a volute. The blower is capable of delivering a supply of air, for example about 120 litres/minute, at a positive pressure in a range from about 4 $cmH_2O$ to about 20 $cmH_2O$, or in other forms up to about 30 $cmH_2O$.

The pressure device 4140 is under the control of the therapy device controller 4240.

Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

Air Circuit 4170

An air circuit 4170 in accordance with an aspect of the present technology is constructed and arranged to allow a flow of air or breathable gasses between the pneumatic block 4020 and the patient interface 3000.

Oxygen Delivery 4180

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

PAP Device Electrical Components 4200

Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

Central Controller 4230

In one form of the present technology, the central controller 4230 is a processor suitable to control a PAP device 4000 such as an x86 INTEL processor.

A processor 4230 suitable to control a PAP device 4000 in accordance with another form of the present technology includes a processor based on ARM Cortex-M processor from ARM Holdings. For example, an STM32 series microcontroller from ST MICROELECTRONICS may be used.

Another processor 4230 suitable to control a PAP device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the processor 4230 for the PAP device 4000. For example a processor from the MSP430 family of microcontrollers, manufactured by TEXAS INSTRUMENTS, may be used.

The processor 4230 is configured to receive input signal (s) from one or more transducers 4270, and one or more input devices 4220.

The processor 4230 is configured to provide output signal (s) to one or more of an output device 4290, a therapy device controller 4240, a data communication interface 4280 and humidifier controller 5250.

The processor 4230, or multiple such processors, may be configured to implement the one or more methodologies described herein such as one or more algorithms 4300 expressed as computer programs stored in a computer readable storage medium, such as memory 4260. In some cases, as previously discussed, such processor(s) may be integrated with a PAP device 4000. However, in some devices the processor(s) may be implemented discretely from the flow generation components of the PAP device, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

Clock 4232

Preferably PAP device 4000 includes a clock 4232 that is connected to processor 4230.

Therapy Device Controller 4240

In one form of the present technology, therapy device controller 4240 is a pressure control module 4330 that forms part of the algorithms 4300 executed by the processor 4230.

In one form of the present technology, therapy device controller 4240 is a dedicated motor control integrated circuit. For example, in one form a MC33035 brushless DC motor controller, manufactured by ONSEMI is used.

Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes removable form of memory 4260, for example a memory card made in accordance with the Secure Digital (SD) standard.

In one form of the present technology, the memory 4260 acts as a computer readable storage medium on which is stored computer program instructions expressing the one or more methodologies described herein, such as the one or more algorithms 4300.

Transducers 4270

Transducers may be internal of the device, or external of the PAP device. External transducers may be located for example on or form part of the air delivery circuit, e.g. the patient interface. External transducers may be in the form of non-contact sensors such as a Doppler radar movement sensor that transmit or transfer data to the PAP device.

Flow 4274

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal or total flow Qt signal, from the flow transducer 4274, is received by the processor 4230. However, other sensors for producing such a flow signal or estimating flow may be implemented. For example, a mass flow sensor, such as a hot wire mass flow sensor, may be implemented to generate a flow signal in some embodiments. Optionally, flow may be estimated from one or more signals of other sensors described here, such as in accordance with any of the methodologies described in a U.S. patent application Ser. No. 12/192,247, the disclosure of which is incorporated herein by reference.

Pressure 4272

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the processor 4230. In one form, the signal from the pressure transducer 4272 is filtered prior to being received by the processor 4230.

Motor Speed 4276

In one form of the present technology a motor speed signal 4276 is generated. A motor speed signal 4276 is preferably provided by therapy device controller 4240. Motor speed may, for example, be generated by a speed sensor, such as a Hall effect sensor.

Data Communication Systems 4280

In one preferred form of the present technology, a data communication interface 4280 is provided, and is connected to processor 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor 4230. In another form, data communication interface 4280 is an integrated circuit that is separate from processor 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

Output Devices Including Optional Display, Alarms 4290

An output device 4290 in accordance with the present technology may take the form of one or more of a visual, audio and haptic unit. A visual display may be a Liquid Crystal Display (LCD) or Light Emitting Diode (LED) display.

Display Driver 4292

A display driver 4292 receives as an input the characters, symbols, or images intended for display on the display 4294, and converts them to commands that cause the display 4294 to display those characters, symbols, or images.

Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

PAP Device Algorithms 4300

Pre-Processing Module 4310

A pre-processing module 4310 in accordance with the present technology receives as an input raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation 4312, vent flow 4314, leak flow 4316, respiratory flow 4318, and jamming detection 4319.

Pressure Compensation 4312

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop in the air circuit 4170 and provides as an output an estimated pressure, Pm, in the patient interface 3000.

Vent Flow 4314

In one form of the present technology, a vent flow calculation algorithm 4314 receives as an input an estimated pressure, Pm, in the patient interface 3000 and estimates a vent flow of air, Qv, from a vent 3400 in a patient interface 3000.

Leak Flow 4316

In one form of the present technology, a leak flow algorithm 4316 receives as an input a total flow, Qt, and a vent flow Qv, and provides as an output a leak flow Ql by calculating an average of Qt-Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and interface pressure, Pm. In one implementation, leak conductance is calculated as the quotient of low pass filtered non-vent flow Qt-Qv, and low pass filtered square root of mask pressure Pm, where the low pass filter time constant has a value sufficiently long to include several breathing cycles, e.g. about 10 seconds.

Respiratory Flow 4318

In one form of the present technology, a respiratory flow algorithm 4318 receives as an input a total flow, Qt, a vent flow, Qv, and a leak flow, Ql, and estimates a respiratory flow to the patient, Qr, by subtracting the vent flow Qv and the leak flow Ql from the total flow Qt.

Jamming Detection 4319

When the leak has recently changed and the leak flow algorithm 4316 has not fully compensated for the change, a state designated as "jamming" exists, which may be determined according to the methods described in U.S. Pat. No. 6,532,957, 6,810,876 or U.S. Patent Application Publication No. 2010/0101574 A1, the disclosures of which are incorporated herein by reference. In the jamming state, the respiratory flow baseline is usually incorrect to some degree, which distorts flow shapes and affects the detection of flow limitation. For example, if the respiratory flow baseline is above the true level, respiratory flow in late expiration will be positive and thus be taken as early inspiratory flow; if this is expiratory pause flow, the true start of inspiration may be taken as the increase after the flat portion of a reverse chair waveform. Hence a fuzzy truth variable, RecentJamming, which represents the extent to which jamming, i.e. uncompensated leak, has recently existed, is calculated by the jamming algorithm 4319.

In the algorithm 4319, an instantaneous jamming fuzzy truth variable J is calculated as the fuzzy extent to which the absolute magnitude of the respiratory flow Qr has been large for longer than expected. The fuzzy extent $A_I$ to which the airflow has been positive for longer than expected is calculated from the time $t_{ZI}$ since the last positive-going zero crossing of the respiratory flow Qr, and the inspiratory duration Ti, using the following fuzzy membership function:

$$A_I = FuzzyMember(t_{ZI}, Ti, 0, 2*Ti, 1) \tag{1}$$

The fuzzy extent $B_I$ to which the airflow is large and positive is calculated from the respiratory flow Qr using following the fuzzy membership function:

$$B_I = FuzzyMember(Qr, 0, 0, 0.5, 1) \tag{2}$$

The fuzzy extent $I_1$ to which the leak has suddenly increased is calculated as the fuzzy "and" of the fuzzy truth variables $A_I$ and $B_I$.

Precisely symmetrical calculations are performed for expiration, deriving $I_E$ as the fuzzy extent to which the leak has suddenly decreased. The fuzzy extent $A_E$ to which the airflow has been negative for longer than expected is calculated from the time $t_{ZE}$ since the last negative-going zero crossing of the respiratory flow Qr, and the expiratory duration Te, using the fuzzy membership function in equation (1). The fuzzy extent $B_E$ to which the airflow is large and negative is calculated from the negative of the respiratory flow Qr using the fuzzy membership function in equation (2), and $I_E$ is calculated as the fuzzy "and" of the fuzzy truth variables $A_E$ and $B_E$. The instantaneous jamming index J is calculated as the fuzzy "or" of the fuzzy truth variables $I_I$ and $I_E$.

If the instantaneous jamming value J is larger than the recent peak value of J, then RecentJamming is set to the instantaneous jamming value J. Otherwise, RecentJamming is set to the instantaneous jamming value J, low pass filtered with a time constant of 10 seconds.

Therapy Engine Module 4320

In one form of the present technology, a therapy engine module 4320 receives as inputs one or more of a pressure, Pm, in a patient interface 3000, a respiratory flow of air to a patient, Qr, a leak flow, Ql, a jamming fuzzy truth variable, RecentJamming, and provides as an output one or more therapy parameters.

In one form of the present technology, the therapy parameter is the CPAP treatment pressure Pt.

In another form of the present technology, the therapy parameters are the EPAP, a waveform value, and a level of pressure support.

In another form of the present technology, the therapy parameters are the EPAP, a waveform value, a target ventilation, and an instantaneous ventilation.

In various forms of the present technology, the therapy engine module 4320 comprises one or more of the following algorithms: phase determination 4321, waveform determination 4322, ventilation determination 4323, flow limitation determination 4324, apnea/hypopnea determination 4325, snore determination 4326, EPAP determination 4327, target ventilation determination 4328, and therapy parameter determination 4329.

In FIGS. 7*a* to 7*q* that illustrate the operation of the therapy engine module 4320, solid connecting lines indicate control flow, while dashed connecting lines indicate data flow.

Phase Determination 4321

In one form of the present technology, a phase determination algorithm 4321 receives as an input a signal indicative of respiratory flow, Qr, and provides an estimate $\Phi$ of the phase of a breathing cycle of the patient 1000. The rate of change of phase is indicative of the respiratory rate.

In one form, the phase estimate $\Phi$ is a discrete variable with values of either inhalation or exhalation. In one form, the phase estimate $\Phi$ is determined to have a discrete value of inhalation when a respiratory flow Qr has a positive value that exceeds a positive threshold. In one form, the phase estimate $\Phi$ is determined to have a discrete value of exhalation when a respiratory flow Qr has a negative value that is more negative than a negative threshold.

In one form, the phase estimate $\Phi$ is a discrete variable with values of one of inhalation, mid-inspiratory pause, and exhalation.

In one form, the phase estimate Φ is a continuous variable, for example varying from 0 to 1, or 0 to 2π, or 0° to 360°. A phase estimate Φ equal to 0.5 (or π or 180°) occurs at the transition from inspiration to expiration.

In one form of the present technology, the phase determination algorithm 4321 uses fuzzy phase estimation as described in U.S. Pat. No. 6,532,957, the disclosure of which is incorporated herein by reference, with a number of adjustments. In general, the philosophy behind the adjustments is to be more tolerant of lower respiratory rates and short-term variations in respiratory rate. The general phase rules are given more weight at lower levels of ventilation than previously, improving patient synchronisation. This more than compensates for the mild reduction in prescriptiveness of the ventilator with respect to maintenance of target ventilation and respiratory rate in the very short term, over one or two breaths.

The "standard rate" of respiration, which corresponds to a kind of backup rate in conventional ventilators, is given a certain weight that depends on the degree of "trouble", a fuzzy logical variable dependent on the degree of jamming, the degree of hypopnea, and the extent to which leak is large. Even in the absence of "trouble", the standard rate is given significant weight. This tends to cause the ventilator's breath rate to be pulled towards the standard rate, and tends to cause dyssynchrony when the patient's respiratory rate is lower than the standard rate, which in one implementation is set at 15 breaths/minute. Awake patients who want to breathe at lower rates, particularly during the sleep onset phase, can feel pushed along by this. A common reaction is to fight the ventilator, resulting in hypoventilation (from the perspective of the ventilator), which further increases the weight given to the standard rate, and higher pressure support.

To counteract this effect, and thereby increase patient comfort, in one form of the present technology, the weight given to the standard rate independent of "trouble" by the algorithm 4321 depends on the minimum pressure support (minimum swing) and the amount of pressure support above the minimum pressure support ("servo swing"), which is determined by the algorithm 4329. Broadly, the idea is that low servo swing levels indicate that the patient has recently been achieving ventilation at or above the target ventilation, and so should be allowed to breathe at whatever rate the patient chooses. Progressively higher servo swing levels progressively indicate that this is less the case. The actual fuzzy membership calculation is performed using the current swing (the sum of the minimum and servo swings), using boundaries (SLow and SHigh) which depend on the minimum swing. The fuzzy truth variable SwingIsLargeForStdRate is the fuzzy extent to which the swing is large, for the purposes of determining the weight to be given to the standard rate (in fact the weight to be given to the standard rates of change of phase for inspiration and expiration, since in general these are different) independent of "trouble".

FIG. 7*a* is a flow chart illustrating a method 7100 that may be used to implement algorithm 4321 in one form of the present technology. The method 7100 begins at step 7110 by computing the lower boundary SLow as a generally increasing function of the minimum swing value MinSwing. In one implementation, SLow is computed as follows:

$$SLow = Interp(MinSwing, 0, 3, 6, 6, 8, 8) \tag{3}$$

At step 7120, the upper boundary SHigh is computed as a generally increasing function of the minimum swing, such that SHigh is always greater than or equal to the lower boundary SLow. In one implementation, SHigh is computed as follows:

$$SHigh = Interp(MinSwing, 0, 6, 6, 8, 8, 8) \tag{4}$$

At step 7130, the method 7100 computes the swing as the sum of the minimum swing and the current servo swing (pressure support above minimum). The method 7100 then at step 7140 computes the fuzzy truth variable SwingIsLargeForStdRate as follows: At or above some rather high level of minimum swing, which in one implementation is 8 $cmH_2O$ (which should not really occur in a ventilator designed to treat periodic breathing of central origin), SwingIsLargeForStdRate is set to fuzzy true. Otherwise, SwingIsLargeForStdRate transitions from fuzzy false to fuzzy true as swing increases between the lower and upper boundaries SLow and SHigh:

$$SwingIsLargeForStdRate = FuzzyMember(\text{Swing}, SLow, 0, SHigh, 1) \tag{5}$$

Finally, at step 7150 the method 7100 estimates the phase in the manner described in U.S. Pat. No. 6,532,957, except that the weight to the standard breath rate, independent of "trouble", is set to the computed value of the fuzzy truth variable SwingIsLargeForStdRate.

The effect of the fuzzy truth function defined by equations (3), (4), and (5) is that both SLow and SHigh rise progressively as MinSwing increases, and that the transition region, between SLow and SHigh, gets progressively narrower as MinSwing increases, particularly as MinSwing exceeds 6, narrowing to zero at MinSwing=8, at which point SLow and SHigh both also equal 8, so that any value of swing equal to or above the minimum swing makes SwingIsLargeForStdRate fuzzy true.

An alternative implementation of the algorithm 4321 omits steps 7110 to 7140 and instead directly computes a fuzzy truth variable indicating the extent to which the patient has recently been achieving ventilation at or above the target ventilation, rather than using low servo swing as an indication of this extent. Step 7150 estimates the phase as described above, giving weight to the standard breath rate, in the absence of "trouble", equal to the value of the computed fuzzy truth variable Waveform Determination 4322

In one form of the present technology, a control module 4330 controls a therapy device 4245 to provide positive airway pressure according to a predetermined waveform of pressure vs phase.

In one form of the present technology a waveform determination algorithm 4322 receives as an input a value Φ indicative of the phase of the current breathing cycle of the patient, and provides as an output a waveform value Π(Φ) in the range [0, 1].

In one form, the waveform is a square wave, having a value of 1 for early values of phase corresponding to inspiration, and a value of 0 for later values of phase corresponding to expiration. In other forms, the waveform is a more "smooth and comfortable" waveform with a gradual rise to 1 for early values of phase, and a gradual fall to 0 for later values of phase. FIG. 8 illustrates an exemplary "smooth and comfortable" waveform Π(Φ), which rises to 1 as the phase increases from 0 to 0.5 during inspiration, and falls to 0 as the phase increases from 0.5 to 1 during expiration.

Ventilation Determination 4323

In one form of the present technology, a ventilation determination algorithm 4323 receives an input a respiratory flow Qr, and determines a value of instantaneous patient ventilation, Vent.

In one form, the ventilation determination algorithm 4323 determines a current value of instantaneous patient ventilation, Vent, as the half the absolute value of respiratory flow, Qr.

Detection of Inspiratory Flow Limitation 4324

In one form of the present technology, a processor executes one or more algorithms 4324 for the detection of inspiratory flow limitation.

In one form, the algorithm 4324 receives as an input a respiratory flow signal Qr and computes one or more measures of the extent to which the inspiratory portion of the breath exhibits inspiratory flow limitation.

The algorithm 4324 computes measures of at least one of the following three types of inspiratory flow limitation: ordinary flatness, M-shape, and "reverse chairness" (see FIGS. 6*f*, 6*h*, and 6*g*).

Flatness

Upper airway flow limitation not infrequently produces a respiratory flow pattern during inspiration in which the airflow stabilises after a relatively short period of inspiration at a fairly stable level, being the level to which airflow is limited by a Starling valve phenomenon well described in the literature, dropping typically late in inspiration. This period of fairly stable airflow appears "flat" in a graphical representation (see FIG. 6*f*). An indication of flatness of an inspiratory waveform may be termed a flattening index (FI). The flattening index of a square waveform is zero. A waveform which is constant during its middle half at a value equal to the overall mean also has a FI of zero; this can occur in practice when the initial rise above the mean in the first quarter of the waveform balances the value below the mean in the last quarter of the waveform. "High" values of the FI (e.g. >0.2) indicate mild or absent flow limitation.

FIG. 7*b* is a flow chart illustrating a method 7200 that may be used to compute a measure of flatness of inspiratory flow limitation as part of the algorithm 4324 in one form of the present technology. The method 7200 starts at step 7210, which computes a flattening index from the inspiratory airflow waveform. In one implementation of step 7210, the mean value of the inspiratory airflow waveform is calculated, the flow values are divided by the mean to produce a normalised waveform, and the RMS deviation of the middle half of the normalised waveform is the flattening index.

In some implementations of step 7210, the pointwise average of the most recent 5 breaths is carried out before the above FI calculation. In other implementations, the FI is calculated on individual breaths and some kind of filtering operation is performed on the recent FI values, such as taking the median of the last three FI values. In yet other implementations, there is no such filtering, such that the FI is derived from only a single breath and a treatment response is directly based on that single breath FI. The rationale for such single-breath implementations is that during periodic breathing of predominantly central origin, such as CSR, the decline of respiratory effort and the onset of upper airway obstruction may be so rapid that there are only one or two flow-limited breaths before the onset of closed (i.e. obstructive) central apnea, or the flow-limited breaths may be intermingled with a variety of shapes not typically indicative of UAO, and it is desirable to respond rapidly to this evidence of flow limitation.

Step 7220 calculates a fuzzy truth variable Flatness at the end of each breath that generally decreases as the flatness index for that breath increases. In one implementation, Flatness is computed as follows:

$$\text{Flatness} = \mathit{FuzzyMember}(FI, 0.05, 1, 0.15, 0) \tag{6}$$

According to equation (6), Flatness is fuzzily true for any value of FI less than or equal to 0.05, because waveforms with FI≤0.05 appear equivalently flow limited to human assessment, the differences between them mostly being due to noise or features unrelated to the degree of flow limitation.

M-Shape

M-shaped inspiratory flow waveforms, with tidal volumes or breathwise ventilation values not much greater than the typical recent values, are indicative of flow limitation. Such waveforms have a relatively rapid rise and fall and a dip or "notch" in flow approximately in the middle, the dip being due to flow limitation (see FIG. 6*h*). At higher tidal volumes or ventilation values, such waveforms are generally behavioural, i.e. microarousals during sleep, or sighs, and are not indicative of flow limitation. In a CPAP device, tidal volume or ventilation is generally decreased by M-shape, but a rapidly responding servo-ventilator will tend to counteract such a fall in ventilation by increasing the pressure support, so that a low ventilation level is not generally a helpful feature in deciding whether the waveform is actually flow-limited.

To detect M-shaped waveforms, the similarity of the inspiratory flow waveform to a waveform which is broadly similar to an M shape is determined.

FIG. 7*c* is a flow chart illustrating a method 7300 that may be used to compute a measure of M-shaped inspiratory flow limitation as part of the algorithm 4324 in one form of the present technology.

Since the notch may not be at the centre of the inspiratory flow waveform, the method 7300 attempts to find the location of the notch, and then linearly time-distorts the waveform so that the notch is at the centre of the waveform. To find the notch, the first step 7310 performs a modified convolution of the normalised inspiratory flow waveform f(t) (wherein the normalisation division by the mean) with a V-shaped kernel V(t) of length Ti/2, centred on zero, where Ti is the duration of inspiration:

$$V(t) = 8\left|\frac{t}{T_i}\right| - 1 \tag{7}$$

The modified convolution is based on separate convolutions with the left and right halves of the kernel V(t). The left half convolution is calculated as $$I_L(\tau) = \int_{\frac{-T_i}{4}}^{0} V(t) f(t-\tau)\,dt \tag{8}$$

and the right half convolution as $$I_R(\tau) = \int_0^{\frac{T_i}{4}} V(t) f(t - \tau) dt \tag{9}$$

The modified convolution I(τ) is computed as a combination of the left and right half convolutions $I_L(\tau)$ and $I_R(\tau)$ such that if either of the left and right half convolutions is zero, the result is zero, regardless of the other quantity, and if both are 1, the result is 1. Thus constrained, the combination of the left and right half convolutions resembles a logical "and" function in some sense, hence is given the name "V-anded convolution". In one implementation, the combination is a modified geometric mean of the left and right half convolutions:

$$I(\tau) = \begin{cases} \sqrt{I_L(\tau) I_R(\tau)}, & I_L(\tau) > 0 \text{ and } I_R(\tau) > 0 \\ 0 & \text{otherwise} \end{cases} \tag{10}$$

The above constraint provides a condition that the inspiratory flow waveform to the left of the posited notch is generally increasing leftwards, and that to the right of the notch is generally increasing rightwards. This provides more specificity than simply summing the left and right integrals. In the implementation given in equation (10), the integrals of the product of the time-shifted normalised inspiratory flow waveform with each half-V must be strictly positive, otherwise the V-anded convolution is zero. This prevents a variety of pathologies, for example, when the part of the inspiratory flow to the left of the centre of the V does not actually increase leftwards, but the integral of the right half of the V waveform is so large that it overwhelms an actually decreasing left half.

The V-anded convolution is performed with the position of the centre of the kernel V(t) ranging from Ti/4 to 3Ti/4, thus yielding results for the central half of the inspiratory flow waveform.

Step 7320 finds the location at which the modified convolution I(τ) peaks, and if the height of this peak is greater than a threshold, a notch is deemed to exist at the location $t_{notch}$ of the centre of the kernel V(t) at which this peak is located. In one implementation, the threshold is set to 0.15.

If a notch is found by step 7320 ("Y") at the location $t_{notch}$, the inspiratory flow waveform f(t) is then, at step 7330, time distorted or "symmetrised" so that half the waveform is to the left of $t_{notch}$ and half is to the right. This operation gives a time-distorted or "symmetrised" version G(t) of the flow waveform f(t):

$$G(t) = \begin{cases} f\left(\frac{t}{\left(\frac{T}{2}\right)} t_{notch}\right), & t < \frac{T}{2} \\ f\left(t_{notch} + \left(\frac{t - \frac{T}{2}}{\frac{T}{2}}\right)(T - t_{notch})\right) & t \geq \frac{T}{2} \end{cases} \tag{11}$$

If no notch is found at step 7320 ("N"), step 7335 sets G(t) to the inspiratory flow waveform f(t), since some waveforms that do not exhibit a detectable notch may still have M-shaped flow limitation.

Define the inner product of two functions on some interval I in the usual way, $$\langle f, g \rangle_I = \int_I f(t) g(t) dt \tag{12}$$

Define first and third sinusoidal harmonic functions of half-width Ti as $$F_1(t) = \sin\left(\pi \frac{t}{Ti}\right) \text{ and } \tag{13}$$

$$F_3(t) = \sin\left(3\pi \frac{t}{Ti}\right) \tag{14}$$

These two harmonic functions are orthogonal on [0, Ti]. For t in [0, Ti], $F_3(t)$ is broadly similar to an M-shaped inspiratory waveform, and $F_1(t)$ is broadly similar to a normal inspiratory waveform. Hence the extent to which the symmetrised waveform G(t) resembles $F_3(t)$ is an indicator of how much the waveform resembles an M. Step 7340 calculates this extent. In one implementation, step 7340 calculates the extent as the ratio M3Ratio of the power in the third harmonic of the symmetrised waveform G(t) to the sum of the power in the first and third harmonics, where it is understood that if the inner product operator has no subscript, the interval is the inspiratory interval [0, Ti]:

$$M3Ratio = \frac{\langle F_3, G \rangle^2}{\langle F_1, G \rangle^2 + \langle F_3, G \rangle^2} \tag{15}$$

When M3Ratio is large, the inspiratory flow waveform typically resembles an M. But M3Ratio can also be large if the waveform is very asymmetric, with a much higher mean flow in either the first or second half of the waveform than in the other half. To exclude this possibility, step 7340 also calculates a measure Symm of the symmetry of the inspiratory flow waveform f(t) about the notch location. In one implementation, step 7340 calculates the third harmonic components of the first and second halves of the symmetrised waveform G(t):

$$M_{3L} = \langle F_3, G \rangle_{\left[0, \frac{Ti}{2}\right]} \tag{16}$$

$$M_{3R} = \langle F_3, G \rangle_{\left[\frac{Ti}{2}, Ti\right]} \tag{17}$$

Step 7340 then calculates the measure Symm as the ratio of the lesser of these components to the sum of their absolute values:

$$Symm = \frac{\min(M_{3L}, M_{3R})}{|M_{3L}| + |M_{3R}|} \tag{18}$$

Step 7350 then tests whether the measure Symm is less than a low threshold, set in one implementation to 0.3. If so ("Y"), the inspiratory flow waveform is deemed not to be symmetrically M-shaped, and a quantity M3RatioSym, which is a measure of the extent to which the inspiratory flow waveform is symmetrically M-shaped, is set equal to zero at step 7360. Otherwise ("N"), M3RatioSym is set equal to M3Ratio at step 7370.

Reverse Chairness

In some patients with partial upper airway obstruction, the flow waveform increases somewhat at the start of inspiration, stays approximately steady, then later in inspiration rises significantly, to levels suggesting an absence of obstruction, then declines to zero in a fairly normal fashion towards the end of inspiration (see FIG. 6*g*). This somewhat resembles a chair seen side-on, with the back of the chair at the end of inspiration; this is termed "reverse chairness", because the typical obstructive sleep apnea flow-limited waveform resembles this shape, but with the back of the chair near the start of inspiration. In the presence of significant pressure support, particularly with a "smooth and comfortable" pressure waveform such as illustrated in FIG. 8, reverse chairness is thought to be due to an initial state of partial obstruction, with the rising pressure opening the upper airway during inspiration, so that in the latter part of inspiration the airway is substantially unobstructed. It has been observed that if this phenomenon is untreated, and the EPAP is progressively lowered, total upper airway obstruction may result. Hence it is desirable to detect reverse chairness and raise EPAP in response to it.

Various non-obstructive behavioural waveforms, most notably a microarousal during sleep, or a sigh, may produce a waveform exhibiting reverse chairness, and so in the present technology measures are taken to attempt not to respond to these non-obstructive causes of reverse chairness.

FIG. 7*d* is a flow chart illustrating a method 7400 that may be used to compute a measure of reverse chairness of inspiratory flow limitation as part of the algorithm 4324 in one form of the present technology.

The method 7400 starts at step 7410, at which a smoothed derivative of the inspiratory flow waveform is calculated. In one implementation, step 7410 convolves the inspiratory flow waveform with the first derivative of a Gaussian function with standard deviation 0.1 seconds. In other implementations of step 7410, various other means with similar frequency response characteristics, such as a suitable low-pass filter followed by differentiation, are used. For detection of a shape characteristic such as reverse chairness, it is desirable that a largely scale-independent derivative be used, and so in one implementation the smoothed derivative (in litres/sec/sec) is normalised at step 7415 by TypVent/9, where TypVent is a measure of typical recent ventilation (in litres/min) (e.g., calculated as described below with reference to FIG. 7*o*), giving a normalised derivative with the units $sec^{-1}$.

Step 7420 then performs shape recognition using a state machine with three states, corresponding to the initial rise, the approximately flat region, and the further rise. Starting at the beginning of the inspiratory flow waveform, in state "LookingForInitialPositive", the normalised derivative is traversed until it is found to be at least 0.3, whereupon the state transitions to "LookingForLevel". In this state, a search is performed, starting from the current position in the normalised derivative, for a normalised derivative value less than 0.05, whereupon the state transitions to "LookingForPositive". The minimum and maximum normalised derivatives from this location onward are continuously updated as the search again proceeds, this time looking for a location at which the maximum normalised derivative has surpassed 0.15, and the normalised derivative is at least 0.05 less than the maximum normalised derivative. The idea of the latter criterion is to provide some hysteresis.

It is clear that as the search proceeds, the maximum normalised derivative can increase, and for what follows it is desirable that a moderately large value is found. Without the criterion that the normalised derivative has decreased moderately from its maximum, the search may terminate rather quickly. Step 7420 returns the difference between the maximum and minimum normalised derivatives, called DerivativeRange. If the third state is never reached, DerivativeRange is returned as zero. Step 7425 then tests whether DerivativeRange is greater than some low threshold, equal to 0.2 in one implementation. If so ("Y"), the waveform is provisionally deemed reverse-chair-shaped, the location tmin of the minimum derivative is recorded, and the method 7400 proceeds to step 7430. Otherwise ("N"), the method 7400 at step 7495 sets a fuzzy truth variable ReverseChairnessCurrent to 0, and concludes.

Step 7430 computes a variable LateProportion, which is the proportion of the inspiratory tidal volume in the latter half of the inspiration, ignoring the first and last 10% of the inspiration by time:

$$LateProportion = \frac{\int_{0.5Ti}^{0.9Ti} |f(t)|dt}{\int_{0.1Ti}^{0.9Ti} |f(t)|dt} \tag{19}$$

Step 7430 also calculates a variable EarlyProportion, the proportion of the inspiratory tidal volume which occurs before the minimum derivative location tmin:

$$EarlyProportion = \frac{\int_{0}^{tmin} |f(t)|dt}{\int_{0}^{Ti} |f(t)|dt} \tag{20}$$

Note the denominator of equation (20) is the inspiratory tidal volume, a quantity that is used later in the method 7400.

Step 7435 compares EarlyProportion to a low threshold, equal to 0.1 in one implementation. If EarlyProportion is less than the threshold ("Y"), the waveform is deemed not reverse-chair shaped, and the method 7400 proceeds to step 7495 as described above. Otherwise ("N"), at step 7440 the typical recent tidal volume (in litres per breath) is calculated. In one implementation, step 7440 divides the typical recent ventilation in litres per minute (e.g. computed as described below with reference to FIG. 7*o*) by the typical respiratory rate in breaths per minute.

Following step 7440, the method 7400 computes three fuzzy truth variables. Step 7445 computes DerivIncreaseIsLarge as a generally increasing function of the DerivativeRange returned by the three-state detection step 7420. In one implementation, step 7445 computes DerivIncreaseIsLarge as follows:

$$DerivIncreaseIsLarge = FuzzyMember(DerivativeRange, 0.25, 0, 0.2, 1) \tag{21}$$

Step 7450 computes LateProportionIsLarge as a generally increasing function of LateProportion. In one implementation, step 7450 computes LateProportionIsLarge as follows:

$$LateProportionIsLarge = FuzzyMember(LateProportion, 0.55, 0, 0.7, 1) \quad (22)$$

Step 7455 computes TidalVolumeIsNotLarge as a generally decreasing function of the inspiratory tidal volume computed at step 7430, with thresholds proportional to the typical recent tidal volume computed at step 7440. In one implementation, step 7455 computes TidalVolumeIsNotLarge as follows $$TidalVolumeIsNotLarge = FuzzyMember(InspTidalVolume, TypicalTidalVolume * 1.3, 1, TypicalTidalVolume * 2.0, 0) \quad (23)$$

Step 7460 computes a real-valued variable NoRecentJamming as a generally decreasing function of the fuzzy truth variable RecentJamming computed by the jamming preprocessing algorithm 4319. In one implementation, step 7460 computes NoRecentJamming as follows:

$$NoRecentJamming = Interp(RecentJamming, 0.25, 1, 0.5, 0) \quad (24)$$

Finally, the method 7400 at step 7470 computes a variable ReverseChairnessCurrent, the fuzzy extent to which the current inspiration is reverse-chair-shaped, as the fuzzy And of DerivIncreaseIsLarge, LateProportionIsLarge, and TidalVolumeIsNotLarge, multiplied by NoRecentJamming:

$$ReverseChairnessCurrent = FuzzyAnd(DerivIncreaseIsLarge, LateProportionIsLarge, TidalVolumeIsNotLarge) * NoRecentJamming \quad (25)$$

Thus the current inspiration is reverse-chair-shaped to the extent that an increase in the derivative after the flat section is moderately large, the proportion of the tidal volume in the latter half of the breath is large, the tidal volume is not large (to help exclude microarousals and sighs), and there has not been any recent jamming.

Detection of Apneas and Hypopneas 4325

In one form of the present technology, a processor 4230 executes one or more algorithms 4325 for the detection of apneas and/or hypopneas.

Total upper airway obstruction produces zero true respiratory airflow. In the presence of ventilatory support, the respiratory airflow as estimated by the ventilator will in general not be zero, even in the absence of leak. The rise in pressure during inspiration in the airpath and the mask results in compression of gas in the airpath, down to the site of upper airway obstruction, and thus there is a true, if small inflow, into the system. In addition, the rise in pressure during inspiration may cause part of the mask to move away from the face, even while maintaining a seal sufficient to prevent any leak, which results in a further inflow of gas into the airpath during inspiration. Corresponding outflows occur during expiration. In addition, the model of leak as a function of mask pressure may be imperfect, particularly at higher leak levels, so that even during zero true airflow the estimated flow may be alternately positive (during inspiration) and negative during expiration. For these reasons a criterion of zero or almost zero respiratory airflow for detecting apneas will often not be met during true closed (i.e. obstructive) apnea, and is thus inappropriate.

Hence, in one form of the present technology, the criterion for detecting apnea is that the airflow is low relative to typical recent airflow.

FIG. 7*e* is a flow chart illustrating a method 7500 that may be used to implement apnea detection as part of the algorithm 4325 in one form of the present technology. In the first step 7510, a measure of the current respiratory airflow is computed. In one implementation, step 7510 computes the RMS value of the respiratory airflow over a short recent interval, in one implementation equal to the last two seconds.

At step 7520, a measure of the typical recent airflow is computed. In one implementation, the measure of typical recent airflow is computed directly, by calculating the RMS value of respiratory airflow in a window of length longer than the interval used in step 7510, in one implementation 60 seconds before the present. In an alternative implementation, step 7520 calculates the square root of the output of a lowpass filter on the square of the value of respiratory airflow, where the lowpass filter has a typical time response of the order of 60 seconds, such as a first-order lowpass filter with time constant 60 seconds.

At step 7530, the ratio of the measure of the current airflow to the measure of typical recent airflow is computed. Step 7540 then tests whether the computed ratio is continuously less than or equal to a low threshold (0.25 in one implementation) for some duration that is greater than or equal to a predetermined duration D (10 seconds in one implementation). If so ("Y"), a Boolean variable (flag), Apnea, indicating whether an apnea was detected, is set to true at step 7550. Otherwise ("N"), the flag is cleared at step 7560. Contiguous periods of time during which Apnea is true are regarded as apnea episodes. According to step 7540, apnea periods must be at least D in duration.

Under conditions of severe but not total upper airway obstruction, a ventilator may produce some true respiratory flow, particularly if it is a ventilator that rapidly increases pressure support in response to hypopnea, as in one form of the present technology. Alternatively, when leak is not well modelled, there may appear to be a modest respiratory airflow, large enough for the method 7500 to not detect an apnea. The true respiratory airflow may be low enough so that if respiratory airflow estimation (algorithm 4318) had been accurate, the method 7500 would have detected an apnea. In either "false negative" situation of apnea detection, the combination of moderate to large pressure support and small absolute airflow, referred to as high ventilation impedance, may be taken as an indication of a hypopnea.

FIG. 7*f* is a flow chart illustrating a method 7600 that may be used to implement hypopnea detection as part of the algorithm 4325 in one form of the present technology. The method 7600 starts at step 7610, which applies a lowpass filter with a characteristic response time on the order of one or two typical breaths to the absolute value of airflow. In one implementation of step 7610, the lowpass filter is a second order Bessel lowpass filter, implemented digitally using the bilinear transform method, with a frequency response having its −3 dB point at 3.2/60 seconds. The output of step 7610 is denoted AbsAirflowFilterOutput.

At the next step 7620, the target absolute airflow (denoted TgtAbsAirflow), is computed as twice the current target ventilation, a continuously changing quantity that is based on the measure of typical recent ventilation, and is computed using the algorithm 4328 described below. Step 7620 then computes a fuzzy truth variable AirflowIsSmall, indicating the extent to which the absolute airflow is small, as a generally decreasing function of AbsAirflowFilterOutput, with thresholds proportional to TgtAbsAirflow. In one implementation, step 7620 computes AirflowIsSmall as follows:

$$AirflowIsSmall = FuzzyMember(AbsAirflowFilterOutput, TgtAbsAirflow*0.15, 1, TgtAbsAirflow*0.25, 0) \quad (26)$$

Step 7630 then computes a fuzzy truth variable SwingIsLarge indicating the extent to which the pressure support (i.e., the swing) is large. In one implementation, step 7630 computes SwingIsLarge as follows:

$$SwingIsLarge = FuzzyMember(\text{Swing}, 6, 0, 8, 1) \quad (27)$$

A fuzzy truth variable VentilationImpedanceIsHigh indicative of high ventilation impedance is calculated at step 7640 as the fuzzy "And" of AirflowIsSmall and SwingIsLarge:

$$\text{VentilationImpedanceIsHigh=FuzzyAnd (AirflowIsSmall, SwingIsLarge)} \quad (28)$$

In a manner corresponding broadly to the apnea detection method 7500, contiguous periods of time during which VentilationImpedanceIsHigh is greater than zero, i.e. is not fuzzily false, are regarded as hypopnea episodes.

Detection of Snore 4326

In one form of the present technology, a processor 4230 executes one or more snore algorithms for the detection of snore.

Snore is generally indicative of upper airway obstruction. A relatively simple technique to obtain a snore signal may include applying a bandpass filter to a pressure signal measured at a suitable location, typically in the ventilator airpath, and deriving an indicator of the magnitude of the filter output, for example by full-wave rectification and low-pass filtering. Some compensation for noise produced by the ventilator is typically necessary.

Mask leak, to some extent vent flow, and various other factors, may produce sounds (designated "spurious snore") which this or other methods of evaluating the degree of snore treat as snore. This can lead to a "positive feedback" situation in which EPAP is increased in response to mask leak, further increasing the amount of mask leak, which is treated as snore, resulting in a further increase in EPAP, and so on.

The broad goal of the algorithm 4326 is to compute a measure of true inspiratory snore and to detect apparent snore during expiration. The aim is to provide an EPAP increase generally increasing with the degree of inspiratory snore, but if the apparent expiratory snore is too large, not to provide any increase in EPAP, because the expiratory snore is very likely to represent mask leak or possibly another source of spurious snore. This means that true expiratory snore is not treated, but true expiratory snore appears to be quite rare, especially in a ventilator rather than a CPAP device, and the resulting gain in specificity is well worthwhile. True snore is generally inspiratory only, maximal in mid to late inspiration, and generally decreases markedly or disappears in the last part of inspiration.

FIG. 7*g* is a flow chart illustrating a method 7700 of computing a measure of inspiratory snore and detecting apparent expiratory snore, that may be used to implement the algorithm 4326 in one form of the present technology.

Since there is no generally accepted standard for measuring snore, in the following the magnitude of snore is expressed in "snore units". In these units, 0 represents no snore, 0.2 represents a very soft snore, 1.0 represents a moderately loud snore, and 2.0 a louder snore. These units are linear in amplitude.

The method 7700 starts at step 7710, which applies a snore filter to the instantaneous mask pressure Pm. In one implementation, the snore filter is a bandpass filter with passband between 30 and 300 Hz, followed by full wave rectification and lowpass filtering with a high frequency cutoff of between 0.5 and 2 Hz. The output of the snore filter is termed "raw snore".

At the next step 7720, a snore threshold is computed. The snore threshold depends not on the EPAP, but on the instantaneous mask pressure Pm, because the spurious snore signal generally varies almost instantaneously with mask pressure, possibly with a small delay due to physical properties, such as inertia, of the mask and face. The snore threshold tsn follows a generally increasing course with increasing mask pressure Pm. In one implementation, step 7720 computes tsn (in snore units) as follows:

$$tsn=\text{Interp}(Pm, 8, 0.20, 10, 0.25, 12, 0.30, 14, 0.40, 16, 0.60, 18, 1.00) \quad (29)$$

Step 7730 follows, at which the method 7700 computes a weighting W(s) to be applied to the amount of raw inspiratory snore s above the snore threshold tsn. If the inspiratory flow is high, the noise produced both in the patient's respiratory system and in the airpath may be considerable, producing spurious snore. In such a situation, the high flow indicates that there cannot be any significant degree of UAO. Raw snore occurring at very high respiratory flows is therefore given a low weighting.

Because, as described above, due to uncompensated leak, there is generally some uncertainty about the baseline of respiratory flow (i.e. a calculated respiratory flow of 0 does not correspond exactly to zero true respiratory flow), raw snore occurring at very low respiratory flows is also given a low weighting.

The weighting function W(s) computed at step 7730 is therefore, in one implementation, given by $$W(s) = Interp(Qr, 0.05, 0, 0.1, 1, 0.5, 1, 0.8, 0) \quad (30)$$

Step 7735 accumulates the weighted difference between the amount of raw snore and the snore threshold tsn over the inspiratory portion of the current breath, by multiplying the difference at each sample (e.g. at 50 Hz) by the weighting function W(s). Step 7740 then, at the end of the inspiratory portion of the current breath, divides the accumulated weighted difference by the accumulation of W(s) over the inspiratory portion. The result is the mean weighted inspiratory snore in excess of threshold (MWISAT) for the current breath.

The method 7700 uses joint thresholds on intensity and duration of raw snore during the expiratory portion for detecting significant expiratory snore. The thresholds are "joint" in the sense that the threshold on duration generally decreases as the threshold on intensity increases. This means that if there has been loud expiratory snore for a short period of time, or softer expiratory snore for a longer period of time, or yet softer expiratory snore for a yet longer period of time, significant expiratory snore is deemed to be present. In one implementation, the durations are measured in terms of time, but in other implementations the durations are normalised by dividing by the duration Te of expiration.

Step 7750 of the method 7700 therefore accumulates a distribution D(s) (analogous to an observed probability distribution function) of the intensity s of raw snore during the expiratory portion of the current breath. In one implementation, step 7750 maintains D(s) as a histogram of raw snore intensities s during expiration. At the conclusion of the current breath, step 7760 converts the distribution D(s) into a reverse cumulative distribution function (CDF) C(s) of raw snore intensity s during the expiration. The reverse CDF C(s) is the proportion of the expiratory duration Te spent at a snore intensity greater than or equal to s. The reverse CDF C(s) is then, at step 7770, compared with a predetermined "critical" snore function Cc(s) that expresses the joint thresholds on intensity and duration. The critical snore function Cc(s) decreases generally with increasing raw snore intensity s. In one implementation, the critical snore function Cc(s) is defined as follows:

$$Cc(s) = Interp(s, 0.2, 10, 0.5, 0.3, 1, 0.1) \quad (31)$$

If the actual snore reverse CDF C(s) is above the critical snore function Cc(s) at any value of raw snore intensity s above a minimum intensity st of raw snore (i.e. if there exists s>st such that C(s)>Cc(s)) ("Y"), step 7780 sets a Boolean variable ExpiratorySnore indicating that significant expiratory snore has been detected to True. Otherwise ("N"), step 7790 sets ExpiratorySnore to False. In one implementation, the minimum intensity st of raw snore is 0.2 snore units.

For example, based on the definition of the critical snore function Cc(s) in equation (31), if expiratory snore intensity has been greater than or equal to 1 snore unit for 0.1 seconds, or if expiratory snore intensity has been greater than or equal to 0.5 snore units for 0.3 seconds, apparent expiratory snore is detected.

Determination of EPAP 4327

In one form of the present technology, a number of different features indicative of upper airway obstruction, if present, cause a rise in the EPAP above a pre-set minimum value minEPAP, to a degree which is broadly proportional to the severity of the upper airway obstruction. When no features indicative of UAO are present, the EPAP decays progressively towards the pre-set minimum EPAP. This decay tends to minimise the EPAP delivered. At any given time, the EPAP is a balance between the forces tending to make it rise and the tendency to decay. An approximate equilibrium may be reached in which occasional indicators of mild UAO cause upward movements in EPAP which are counterbalanced by the decay that occurs when there are no indicators of UAO.

The EPAP response to the indications of flow limitation is progressive (i.e., more flow limitation results in a greater EPAP component compared to the EPAP component due to less flow limitation), because with progressively more severe flow limitation the need to respond rapidly to try to prevent an apnea or arousal increases, and also because there is less uncertainty about the presence of flow limitation. Control systems with progressive responses to signals are also almost invariably more stable and generally better behaved than those with large changes in response to small changes in the level of signals.

When the algorithm 4327 prescribes an increase in EPAP, that increase may not occur instantaneously. Such rises in EPAP may be controlled by the processor 4230 and timed to occur only during what the PAP device 4000 considers to be inspiration. It is believed that rises in EPAP during expiration are more prone to cause arousals than the same rises during inspiration, probably because a rise in inspiration decreases inspiratory work, but a rise in expiration tends to push the patient into the next inspiration. An example of such a technique is disclosed in U.S. Patent Application Publication No. 2011/0203588 A1, the disclosure of which is incorporated herein by reference.

FIG. 7*h* is a flow chart illustrating a method 7800 of determining a new value of EPAP, CurrentEPAP, as a function of the various indications of upper airway obstruction computed by the algorithms 4324, 4325, and 4326. The method 7800 may be used to implement the algorithm 4327 in one form of the present technology.

The method 7800 computes five separate components of EPAP above the pre-set minimum value minEPAP: $EPAP_{(1,2)}$ (due to apnea and/or high ventilation impedance) at step 7810, $EPAP_{(3)}$ (due to flatness of inspiratory flow) at step 7820, $EPAP_{(4)}$ (due to M-shaped inspiratory flow) at step 7830, $EPAP_{(5)}$ (due to reverse chairness of inspiratory flow) at step 7840, and $EPAP_{(6)}$ (due to snore) at step 7850. Step 7860 adds these five components to the pre-set minimum value minEPAP. Finally at step 7870, the method 7800 ensures that the resulting new value of CurrentEPAP does not exceed a pre-set maximum value maxEPAP. In other words, step 7870 "clips above" the newly computed value of CurrentEPAP to maxEPAP. The method 7800 then concludes.

Each of the steps 7810 to 7850 takes as input, in addition to the corresponding measure(s) of UAO, one or more of the following PAP device variables or signals: the respiratory flow Qr, the amount Leak of leak (equal to the leak flow Ql, in litres per second), the current target ventilation Vtgt, the present value of CurrentEPAP, the amount of swing (or pressure support), the instantaneous mask pressure Pm, and the recent jamming fuzzy truth variable RecentJamming.

In general, it makes sense to require stronger evidence of UAO for the same rise in EPAP as the current value of EPAP increases, because the potential adverse consequences of raised EPAP increase as the EPAP increases. These consequences are that the maximum possible pressure support, given a fixed maximum pressure, decreases, and leak becomes more likely. As leak increases, the level of confidence in the accuracy of the calculated respiratory flow waveform decreases, because leak models tend to become increasingly inaccurate as the magnitude of the leak increases.

EPAP Component Due to Apnea/Hypopnea

In step 7810, the EPAP component $EPAP_{(1,2)}$ increases with the duration of the detected episode of apnea or high ventilation impedance (HVI). Since episodes of apnea and high ventilation impedance as calculated by the algorithm 4325 may overlap, it is desirable to combine them in some way.

FIG. 7*i* is a flow chart illustrating a method 7900 which may be used to implement step 7810 of the method 7800. The method 7900 starts at step 7910, which determines whether an episode of apnea or HVI, i.e. a period during which it is continuously the case that FuzzyOr (VentilationImpedanceIsHigh, Apnea)>0 (here taking Apnea to be a fuzzy truth variable which is either 0 or 1), has just ceased. If so ("Y"), the next step 7920 computes the duration T_apn_Rx of the episode for therapy purposes. In one implementation of step 7920, the duration is computed by calculating a weight function W(t) for each time t as follows: where Apnea is true, W(t)=1; when Apnea is false but VentilationImpedanceIsHigh is not fuzzily false, W(t) depends on the value of VentilationImpedanceIsHigh, for example W(t) is a scaling factor multiplied by VentilationImpedanceIsHigh. The integral with respect to time of W(t) over the episode may then be taken as the duration T_apn_Rx of the combined apnea and high ventilation impedance episode for therapy purposes.

Another implementation of step 7920, which is simpler and more conservative, is as follows. If there was an apnea during the episode, the period of high ventilation impedance is ignored and T_apn_Rx is taken just to be the actual apnea duration as described above. Otherwise, T_apn_Rx is set equal to the weighted duration of high ventilation impedance, determined by integrating VentilationImpedanceIsHigh as described above, multiplied by a scaling factor.

In either implementation of step 7920, the scaling factor is set to be between 0 and 1, for example 0.75, due to the fact that when only the state of high ventilation impedance exists, either the hypopnea is not as severe as that which obtains when the apnea detection method 7500 detects an apnea, or that there has actually been an apnea, but there is lower confidence that this is the case, or some combination of these two possibilities, so the hypopnea deserves less therapy than a clearly diagnosed apnea of the same duration.

In steps 7930 and 7940, the EPAP component $EPAP_{(1,2)}$ due to apnea/hypopnea is computed in such a way that with increasing T_apn_Rx, the maximum possible new value of EPAP as a result of $EPAP_{(1,2)}$, termed MaxPossibleNewEPAP, exponentially approaches a value, termed HighApneaRollOffPressure, that is set somewhat above the maximum possible EPAP value maxEPAP. In one implementation of step 7930, $$HighApneaRollOffPressure = maxEPAP + 2 \tag{32}$$

and $$MaxPossibleNewEPAP = CurrentEPAP + (HighApneaRollOffPressure - CurrentEPAP) * (1 - \exp(k * \text{T\_apn\_Rx})) \tag{33}$$

The rate constant k in equation (33) (with units 1/sec) is decreased as HighApneaRollOffPressure increases, to avoid too rapid an increase in pressure at low EPAP values. In one implementation of step 7930, $$k = 1/45 * 10/HighApneaRollOffPressure \tag{34}$$

The actual new EPAP as a result of $EPAP_{(1,2)}$ is then limited at step 7940 to be no more than maxEPAP. The component $EPAP_{(1,2)}$ is therefore computed at step 7940 as $$EPAP_{(1,2)} = \min(MaxPossibleNewEPAP, maxEPAP) - CurrentEPAP \tag{35}$$

If step 7910 returns "N", i.e. no increase in EPAP due to apnea/hypopnea is prescribed, at step 7950 the EPAP component $EPAP_{(1,2)}$ decayed exponentially towards zero using a time constant $\tau_{1,2}$. This is accomplished by reducing $EPAP_{(1,2)}$ by $EPAP_{(1,2)}*\Delta T/\tau_{1,2}$, where $\Delta T$ is the interval since the last update of $EPAP_{(1,2)}$. In one implementation, the time constant $\tau_{1,2}$ is 40 minutes.

EPAP Component Due to Flatness

FIG. **7*j* is a flow chart illustrating a method 71000 that may be used to implement step 7820 of the method 7800**.

As the value of CurrentEPAP rises, the level of flatness of inspiratory flow limitation required for any increase in the EPAP component $EPAP_{(3)}$ due to flatness increases. The method 71000 therefore starts at step 71010, which calculates a value CurrentEEP_RxFactor that generally decreases as CurrentEPAP increases. In one implementation, $$\text{CurrentEEP\_RxFactor} = Interp(CurrentEPAP, 12, 1, 16, 0.6) \tag{36}$$

In addition, the increase in $EPAP_{(3)}$ is decreased progressively as the amount of leak increases. The method 71000 therefore at step 71020 computes a variable LeakRxFactor which generally decreases as Leak increases. In one implementation, step 71020 computes LeakRxFactor as follows:

$$LeakRxFactor = Interp(\text{Leak}, 0.5, 1, 1, 0) \tag{37}$$

The thresholds 0.5 and 1.0 on Leak in equation (37) are higher than in previous technology.

In addition, as "valve-like leak", an indicator of mouth leak, increases, the minimum level of flatness required for any increase in $EPAP_{(3)}$ increases. Step 71030 therefore computes a variable EarlyExpLeakRatio as the ratio of the peak flow in the first 0.5 seconds of expiration to the mean flow in the next 0.5 seconds of expiration. During valve-like leaks, EarlyExpLeakRatio typically exceeds 5:1. Normal breathing gives a ratio of about 1:1 to 4:1. Step 71030 then calculates a variable ValveLikeLeak_RxFactor that generally decreases as EarlyExpLeakRatio increases above the thresholds that indicate valve-like leak is likely to be happening. In one implementation, $$\text{ValveLikeLeak\_RxFactor} = Interp(EarlyExpLeakRatio, 4, 1, 5, 0) \tag{38}$$

From these three factors, step 71040 calculates a threshold MinFlatnessForRx on flatness for any increase in EPAP $_{(3)}$ to be prescribed, as follows:

$$MinFlatnessForRx = 1 - LeakRxFactor * \text{ValveLikeLeak\_RxFactor} * \text{CurrentEEP\_RxFactor} \tag{39}$$

According to equations (36) to (39), if any of CurrentEPAP, Leak, or valve-like leak is large, the threshold MinFlatnessForRx is close to 1, and hence only severe flatness will cause any increase in $EPAP_{(3)}$.

Step 71050 then tests whether the value of Flatness computed by the algorithm 4324 is less than or equal to the threshold MinFlatnessForRx. If not ("N"), the increase $\Delta EPAP_{(3)}$ in $EPAP_{(3)}$ is calculated at step 71060 in proportion to the excess of Flatness over the threshold MinFlatnessForRx. In one implementation, the constant of proportionality is 0.5 $cmH_20$:

$$\Delta EPAP_{(3)} = (\text{Flatness} - MinFlatnessForRx) * 0.5. \quad (40)$$

Step 71060 then increases $EPAP_{(3)}$ by $\Delta EPAP_{(3)}$. Step 71070 clips the increased value of $EPAP_{(3)}$ to maxEPAP–CurrentEPAP, to ensure the increased value of EPAP as a result of flatness does not exceed maxEPAP.

If step 71050 determines that Flatness is less than or equal to MinFlatnessForRx ("Y"), at step 71080 the value of $EPAP_{(3)}$ is decayed exponentially towards zero using a time constant $\tau_3$. This is accomplished by reducing $EPAP_{(3)}$ by $EPAP_{(3)}*\Delta T/\tau_3$, where $\Delta T$ is the interval since the last update of $EPAP_{(3)}$. In one implementation, the time constant $\tau_3$ is 20 minutes.

EPAP Component Due to M-Shape

FIG. **7*k* is a flow chart illustrating a method 71100 that may be used to implement step 7830 of the method 7800** in one form of the present technology.

Very long inspiratory flow waveforms may have an approximately M-shaped appearance, but this rarely reflects the flow-limited breathing. Hence, the method 71100 starts at step 71110, which tests whether the duration Ti of inspiration is greater than a "long" threshold, 3.5 seconds in one implementation. If so ("Y"), a variable MRxProportion, the proportion of the maximum increase per breath in $EPAP_{(4)}$, the EPAP component due to M-shaped inspiratory flow, to be applied in the current breath, is set to 0 at step 71120. Otherwise ("N"), step 71130 computes MRxProportion to increase generally with the value of M3RatioSym computed by the algorithm 4324. In one implementation, step 71130 computes MRxProportion from M3RatioSym as follows:

$$MRxProportion = Interp(M3RatioSym, 0.17, 0, 0.3, 1) \quad (41)$$

Breaths with ventilations significantly larger than the typical recent ventilation rarely reflect flow limitation, and are usually behavioural. Therefore, following either step 71120 or step 71130, step 71040 calculates the ratio of the breathwise ventilation (the mean of the instantaneous ventilation Vent over the breath) to the typical recent ventilation (e.g. computed as described below with reference to FIG. **7*o*). Step 71140 then adjusts MRxProportion to generally decrease as that ratio increases. In one implementation, step 71140** adjusts MRXProportion as follows:

$$MRxProportion := MRxProportion * Interp(BreathwiseVentilation/TypicalRecentVentilation, 1.1, 1, 1.3, 0) \quad (42)$$

Step 71150 tests whether M3RatioSym is greater than 0. If so ("Y"), step 71160 increases $EPAP_{(4)}$ by an amount $\Delta EPAP_{(4)}$ proportional to MRxProportion The constant of proportionality, i.e. maximum increase per breath in the EPAP component due to M-shaped inspiratory flow, in one implementation, is set to 0.3 $cmH_20$:

$$\Delta EPAP_{(4)} = MRxProportion * 0.3. \quad (43)$$

Step 71170 clips the increased value of $EPAP_{(4)}$ to maxEPAP–CurrentEPAP, to ensure the new value of EPAP does not exceed maxEPAP.

If step 71150 determines that M3RatioSym is not greater than zero ("N"), at step 71180 the value of $EPAP_{(4)}$ is decayed exponentially towards zero using a time constant $\tau_4$. This is accomplished by reducing $EPAP_{(4)}$ by $EPAP_{(4)}*\Delta T/\tau_4$, where $\Delta T$ is the interval since the last update of $EPAP_{(4)}$. In one implementation, the time constant $\tau_4$ is 20 minutes.

EPAP Component Due to Reverse Chairness

FIG. **7*l* is a flow chart illustrating a method 71200 that may be used to implement step 7840 of the method 7800**.

As the current value of EPAP increases, it is desirable to have greater confidence that the underlying state which causes reverse chairness is indeed present, before further increasing the EPAP. One way to achieve this is to assess the extent to which the preceding breath also exhibits reverse chairness, and then, as the current EPAP rises, increasingly favour that measure of "consistency" over the simple reverse chairness of the current breath when computing the increase in EPAP.

The first step 71210 of the method 71200 therefore calculates a variable ReverseChairnessConsistent as a weighted geometric mean of ReverseChairnessCurrent computed by the algorithm 4324 for the current and preceding breaths. This calculation can be interpreted as a particular kind of fuzzy "and" function over current and preceding breaths.

In one implementation, step 71210 finds the minimum and maximum of the values of ReverseChairnessCurrent for the current and preceding breaths, designating them MinChairness and MaxChairness. If either or both of MinChairness and MaxChairness is zero, the reverse chairness measure ReverseChairnessConsistent is set to zero. Otherwise, in one implementation step 71210 calculates ReverseChairnessConsistent as follows:

$$ReverseChairnessConsistent = \exp(0.6 * \log(MinChairness) + 0.4 * \log(MaxChairness)) \quad (44)$$

Step 71220 then computes a variable ReverseChairnessForRx, a measure of reverse chairness for therapy purposes, that transitions from ReverseChairnessCurrent to ReverseChairnessConsistent as CurrentEPAP increases. In one implementation, step 71220 computes ReverseChairnessForRx as $$ReverseChairnessForRx = Interp(CurrentEPAR, 8, ReverseChairnessCurrent, 10, ReverseChairnessConsistent) \quad (45)$$

Step 71230 then tests whether ReverseChairnessForRx is less than a low threshold, 0.05 in one implementation. If not ("N"), the reverse chairness is deemed significant, step 71240 increases the EPAP component $EPAP_{(5)}$ due to reverse chairness by an amount $\Delta EPAP_{(5)}$ that is proportional to ReverseChairnessForRx by an amount that decreases with increasing current EPAP and increasing leak. In one implementation, step 71240 increases $EPAP_{(5)}$ by $$\Delta EPAP_{(5)} = 0.2 * Interp(CurrentEPAP, 10, 1, 20, 0) * Interp(\text{Leak}, 0, 5, 1, 1, 0) * ReverseChairnessForRx \quad (46)$$

Step 71250 clips the increased value of $EPAP_{(5)}$ to maxEPAP–CurrentEPAP, to ensure the new value of EPAP does not exceed maxEPAP.

If step 71230 determines that ReverseChairnessForRx is insignificant ("N"), at step 71260 the value of $EPAP_{(5)}$ is decayed exponentially towards zero using a time constant $\tau_5$. This is accomplished by reducing $EPAP_{(5)}$ by $EPAP_{(5)}*\Delta T/\tau_5$, where $\Delta T$ is the interval since the last update of $EPAP_{(5)}$. In one implementation, the time constant $\tau_5$ is 20 minutes.

EPAP Component Due to Snore

FIG. 7*m* is a flow chart illustrating a method 71300 that may be used to implement step 7850 of the method 7800.

The method 71300 start at step 71320, which examines the Boolean variable ExpiratorySnore, indicating that significant expiratory snore has been detected, computed by the algorithm 4326. If step 71320 determines that ExpiratorySnore is true ("Y"), at step 71330 the value of the component $EPAP_{(6)}$ of EPAP due to snore is decayed exponentially towards zero using a time constant $\tau_6$. This is accomplished by reducing $EPAP_{(6)}$ by $EPAP_{(6)}*\Delta T/\tau_6$, where $\Delta T$ is the interval since the last update of $EPAP_{(6)}$. In one implementation, the time constant $\tau_6$ is 20 minutes.

Otherwise ("N"), step 71340 determines whether the mean weighted inspiratory snore above the threshold (MWISAT) computed by the algorithm 4326 is greater than zero, indicating inspiratory snore is present. If not ("N"), the method 71300 proceeds to step 71330 to decay the value of EPAP(6) towards zero as described above.

Otherwise ("Y"), the EPAP component $EPAP_{(6)}$ is increased according to the MWISAT value. As explained earlier, when there is jamming, there is greater uncertainty about the respiratory flow baseline. Hence the amount of increase in $EPAP_{(6)}$ is decreased with increasing jamming, and in particular with the maximum value of the fuzzy truth variable RecentJamming during the breath just completed. This maximum value, MaxJammingDuringBreath, is computed from RecentJamming at step 71350.

Step 71360 then increases $EPAP_{(6)}$ by an amount $\Delta EPAP_{(6)}$ that is proportional to MWISAT by an amount that decreases as MaxJammingDuringBreath increases. In one implementation, step 71360 increases $EPAP_{(6)}$ by $$\Delta EPAP_{(6)} = 1.5\ \text{cmH}_2\text{O} * Interp(MaxJammingDuringBreath, 0.15, 1, 0.3, 0) * MWISAT \quad (47)$$

Finally, step 71370 clips the increased value of $EPAP_{(6)}$ to maxEPAP–CurrentEPAP, to ensure the new value of EPAP does not exceed maxEPAP.

Determination of Target Ventilation 4328

In previous approaches, the target ventilation has been set to 90% of the typical recent ventilation, calculated as the output of a first-order lowpass filter with time constant 3 minutes (the ventilation filter) that is applied to the instantaneous ventilation.

Under such approaches, there is a fundamental asymmetry in the dynamics of target ventilation with respect to increases and decreases. The ventilator does nothing to counteract a rise in ventilation (it merely lowers its pressure support to minimum), but counteracts a fall in ventilation by supporting the ventilation at 90% of the typical recent value. Consider the simple case of a sudden reduction in patient effort to zero. If the maximum pressure support were zero, the actual ventilation would be zero, and so the ventilation filter output would fall towards zero with a time constant of 3 minutes. However, if maximum pressure support is adequate to maintain the target ventilation, the actual ventilation is maintained at 90% of the value just before patient effort dropped to zero. Hence the difference between the output and the input of the ventilation filter is 10% of what it would have been had there been no pressure support, and so the rate of fall of the output value is 10% of what it would have been, causing the ventilation to decline with a time constant of 1/0.1*3=30 minutes.

Because it is easy for target ventilation to rise, but hard for it to fall, brief rises in actual ventilation produce long-lived rises in target and actual ventilation. Such rises are typically due either to arousals during sleep or to awake breathing, where a brief rise in ventilation may be associated with the effort of getting into bed or moving around in bed, or to anxiety produced by the ventilator aggressively supporting ventilation during the brief apneas and hypopneas which are normal at sleep onset, but which the ventilator treats as the potential onset of a cycle of periodic breathing. In addition, when the ventilator's target ventilation is above the actual ventilation, the ventilator becomes increasingly insistent on delivering breaths at the standard rate, which in an awake patient, can cause further discomfort, anxiety, and fighting the ventilator followed by bursts of hyperventilation, which further raises the target ventilation and thus exacerbates the situation. Moreover, an aim of the present technology is to stabilise the ventilation, not to set any particular level, and the patients in whom it is generally used have arterial $CO_2$ levels below normal, with the goal in these patients being to raise the $CO_2$ level, so it is desirable to maintain pressure support at the lowest level consistent with awake comfort.

To this end, the present technology contains features designed to make it harder for the target ventilation to rise rapidly, and to make it easier for the target ventilation to fall when pressure support has been reasonably stable for a while, and hence by the above considerations is at an inappropriately high level.

FIG. 7*n* is a flow chart illustrating a method 71400 of computing the target ventilation, that may be used to implement the algorithm 4328 in one form of the present technology.

The method 71400 starts at step 71410, which computes a measure of the typical recent ventilation from the instantaneous ventilation (computed by the algorithm 4323), as described in detail below with reference to FIG. 7*o*. Step 71410 is sometimes referred to as the typical recent ventilation filter. The following step 71420 computes a fuzzy truth variable ShouldSpeedUpTargetVentilationAdjustment, the fuzzy extent to which any fall in target ventilation should be speeded up, from the current value of pressure support, as described below with reference to FIG. 7*p*. Step 71430 then computes a target fraction that is to be multiplied by the typical recent ventilation. In previous approaches, the target fraction was fixed at a value just below 1, e.g. 0.9. One mechanism for lowering the target ventilation more rapidly involves decreasing the target fraction to a value slightly further below 1 as ShouldSpeedUpTargetVentilationAdjustment increases. In one implementation, step 71430 computes the target fraction as $$Interp(ShouldSpeedUpTargetVentilationAdjustment, 0, 0.9, 1, 0.8) \quad (48)$$

which has the effect of producing a target fraction of 0.8 when ShouldSpeedUpTargetVentilationAdjustment is fully true.

The next step 71440 multiplies the computed target fraction by the measure of typical recent ventilation computed by step 71410. The resulting product is passed to step 71460 that computes the target ventilation, as described in detail below with reference to FIG. 7*q*. Step 71460 is sometimes referred to as the target ventilation filter. The rate constant (the reciprocal of the time constant) of the low pass filter that computed the target ventilation in previous approaches was fixed, typically at 1/180, and equal for both increases and decreases in target ventilation. However, another mechanism for lowering the target ventilation more rapidly is to increase the decreasing rate constant of the target ventilation filter as ShouldSpeedUpTargetVentilationAdjustment increases. Step 71450 therefore computes a factor SpeedUpRatio that generally increases with ShouldSpeedUpTargetVentilationAdjustment, to be multiplied by the decreasing rate constant in step 71460. In one implementation, step 71450 computes the factor SpeedUpRatio as follows:

$$SpeedUpRatio = 1 + 2 * ShouldSpeedUpTargetVentilationAdjustment \quad (49)$$

so that when ShouldSpeedUpTargetVentilationAdjustment is fully true, the decreasing rate constant has a maximum value of 3 times its basic value.

The combination of these two mechanisms (equations (48) and (49)) can thus produce a speedup in downward adjustment of target ventilation by a factor of 6.

The time taken to reduce the target ventilation to the patient's mean ventilation requirement depends on how much the target ventilation is above this requirement, but it is not unusual to see a reduction in target ventilation over a period of 1 to 3 minutes (after the initial 90 seconds of stable nontrivial pressure support) such that the target and hence actual ventilation is lowered to a level which results in the arterial $CO_2$ being above the apneic threshold, so that intrinsic respiratory drive returns, and thus pressure support drops rapidly to minimum.

FIG. 7*o* is a flow chart illustrating a method 71500 of computing a measure of the typical recent ventilation, as used to implement step 71410 in the method 71400 in one form of the present technology.

Jamming (described above), by shifting the respiratory flow baseline, almost always causes an unjustified increase in apparent ventilation, and therefore the typical recent ventilation. Thus, in one form of the present technology, the rate of adjustment of typical recent ventilation is reduced when there is, or has recently been, jamming.

The instantaneous ventilation (computed by the algorithm 4323) is input to a jam-dependent lowpass filter 71510 that comprises the steps 71520 to 71580, executed on receipt of each input sample. The jam-dependent filter 71510 effectively slows down time to the extent that there is, or has recently been, jamming. The time-slowing in the jam-dependent filter 71510 is implemented by accumulating the proportion of an update which should be performed to the jam-dependent filter output, and allowing the update to occur only when that accumulated proportion exceeds one. The rate of updating of output samples of the jam-dependent filter is thereby reduced by the value of the update proportion. The first step 71520 therefore computes a variable UpdateProportion that generally decreases from 1 to 0 as RecentJamming increases. In one implementation, step 71520 computes UpdateProportion as $$UpdateProportion = Interp(Recentjamming, 0, 1, 1, 0.3, 0) \quad (50)$$

The next step 71530 increments an accumulated value of UpdateProportion by UpdateProportion. Step 71540 then tests whether the accumulated value of UpdateProportion is greater than or equal to one. If not ("N"), a variable WeightedSum is incremented by the product of UpdateProportion and the ventilation filter's current output sample (step 71550). The method 71500 then returns to step 71520 to compute a new value of UpdateProportion from RecentJamming.

When the accumulated value of UpdateProportion is at least equal to 1 ("Y"), a variable WeightedVentilation is computed at step 71560 as the sum of WeightedSum and the product of the ventilation filter's current output sample and one minus the previous value of the accumulated UpdateProportion (which was less than one).

Next, at step 71570 the accumulated value of UpdateProportion is re-initialised (to a value between 0 and 1) by subtracting one from the accumulated value of UpdateProportion. Finally, step 71580 re-initialises WeightedSum by multiplying the new value of the accumulated UpdateProportion by the ventilation filter's current output sample. The method 71500 then returns to step 71520 to compute a new value of UpdateProportion from RecentJamming.

The output of the jam-dependent filter 71510 is the sequence of values of WeightedVentilation produced by step 71560. If UpdateProportion is 1 (as when RecentJamming is fully false), the output of the jam-dependent filter 71510 is simply the instantaneous ventilation. If UpdateProportion becomes zero (as when RecentJamming is fully true), the output of the jam-dependent filter 71510 is frozen at its current value. In the intermediate case where UpdateProportion is between 0 and 1, (as when RecentJamming is between 0.1 and 0.3), say 1/N where N is an integer, the output of the jam-dependent filter 71510 is an N-sample average of the instantaneous ventilation, updated once every N samples.

Because there is necessarily some delay in deciding whether jamming is present (for example, at quiet end-expiration, a sudden rise in leak is indistinguishable from true inspiratory flow; the difference takes a little while to become apparent), the output of the jam-dependent filter 71510 is, in one form of the present technology, passed to a ventilation filter 71590 whose response has a similar time course to the jamming detection algorithm 4319. Hence the output of the ventilation filter 71590 does not rise in response to a sudden uncompensated leak until RecentJamming starts to become fuzzily true. The output of the ventilation filter 71590 is then the typical recent ventilation.

In one implementation, the ventilation filter 71590 is a second-order Bessel lowpass filter with a minus 3 db point of 0.0178 Hz. In other implementations, the response of the ventilation filter 71590 is slow enough to reduce within-breath fluctuations in ventilation to a value much lower than the upward slew rate limit described below, and fast enough that its time constant is less than the three-minute time constant used in the typical recent ventilation filter of previous approaches.

In an alternative implementation of step 71410, the ventilation filter 71590 precedes the jam-dependent filter 71510. The output of the jam-dependent filter 71510 is then used as the measure of typical recent ventilation.

Despite imposing a maximum limit on the rate of increase of target ventilation as described below, it is still relatively easy for the target ventilation to be above what the patient actually requires in mean. This may occur when target ventilation rises due to arousals, or may simply be a result of the wake to sleep transition, when both metabolic rate decreases and respiratory controller $CO_2$ response decreases, and “awake drive” disappears. Again, an aim of the present technology is to deliver pressure support above minimum only when actually necessary to deal with relatively brisk and brief falls in central drive, in order to stabilise ventilation in a respiratory system in which ventilation would otherwise oscillate.

Hence, as described above, the method 71400 incorporates a step 71420 of detecting a state of fairly stable pressure support significantly above the minimum, and mechanisms (equations (48) and (49)) to speed target ventilation adjustment downwards when that occurs.

FIG. 7*p* is a flow chart illustrating a method 71600 of computing the fuzzy truth variable ShouldSpeedUpTargetVentilationAdjustment as used at step 71420 of the method 71400 in one form of the present technology.

Broadly, the method 71600 computes the fuzzy extent to which the pressure support above minimum (the “servoassistance” or “servo swing”) has been fairly stable for a first recent period and also for a second recent period substantially shorter than the first recent period, then pressure support has been fairly stable for a while and is currently fairly stable. This could be determined by a variety of statistical measures of spread, such as standard deviation, mean absolute deviation, or a high pass filter of some type; a fairly low value of spread obtained by any of these indicates that the pressure support is fairly stable. In the method 71600, order statistics are used to determine stability, generally being more robust, especially when the distribution in the particular individual is unknown, as it typically is in this case.

In one implementation of the method 71600, the first recent period is the most recent 90 seconds and the second recent period is the most recent 30 seconds. The choice of 90 seconds as the period over which to assess stability is determined by the fact that essentially all Cheyne-Stokes oscillations of central drive have a period of 90 seconds or less, 40 to 60 seconds being the usual range. Periodic breathing of other causes tends to have periods of 60 seconds or less. Thus if the ventilator were delivering significant servoassistance only to stabilise such oscillations, it could not be fairly stable over a period of 90 seconds.

The method 71600 starts at step 71610, at which the pressure support above minimum is lightly lowpass filtered, in one implementation with a time constant of 2 seconds. The next step 71620 calculates running order statistics over the most recent 30 seconds. In one implementation of step 71620, a histogram of values over the most recent 30 seconds is continually updated by means of a circular buffer of input values 30 seconds in length. When a new input value is to be added, the histogram categories of the newest and oldest sample in the circular buffer are determined, the count in the histogram category of the oldest sample is decremented by one and the count in the histogram of the newest sample is incremented by one. Determination of approximate order statistics from histograms is routine. In particular, step 71620 computes a measure of spread referred to as Spread30 as the difference between the 0.8 and the 0.2 order statistic, equivalently the difference between the 80th percentile value and the 20th percentile value. Step 71620 also computes the median, referred to as Median30. The following step 71630 computes the ratio of Spread30 to Median30.

Step 71640 follows, at which running order statistics over the most recent 90 seconds are calculated in similar fashion to step 71620. In particular, step 71640 computes a measure of spread referred to as Spread90 as the difference between the 0.8 and the 0.2 order statistic, equivalently the difference between the 80th percentile value and the 20th percentile value.

The final step 71650 computes the fuzzy truth variable ShouldSpeedUpTargetVentilationAdjustment based on the computed order statistics and the constant MaxPossibleServoAssistance, the difference between maximum and minimum pressure support.

If Median30 is less than a low threshold value, set to 2 in one implementation, step 71650 sets ShouldSpeedUpTargetVentilationAdjustment to zero, because recent pressure support cannot be stable and high under these circumstances. Otherwise, step 71650 computes ShouldSpeedUpTargetVentilationAdjustment as the fuzzy “And” of five fuzzy truth variables. The first of the five fuzzy truth variables that is fuzzy “Anded” to compute ShouldSpeedUpTargetVentilationAdjustment indicates the extent to which MaxPossibleServoAssistance is large compared to predetermined thresholds. This variable is present because when MaxPossibleServoAssistance is small, it is fairly easy for the servoassistance to be small even in the presence of large fluctuations in actual ventilation, so any apparent stability in pressure support is discounted.

The next two fuzzy truth variables evaluate the extent that pressure support has been fairly stable over the most recent 30 seconds. The fourth fuzzy truth variable evaluates the extent to which servoassistance has been nontrivial (e.g., generally sufficient to affect the patient's respiratory pattern) over the last 30 seconds, and the last fuzzy truth variable evaluates the extent to which pressure support has been stable over the last 90 seconds.

In one implementation step 71650 computes ShouldSpeedUpTargetVentilationAdjustment as follows:

$$\begin{aligned} &ShouldSpeedUpTargetVentilationAdjustment = FuzzyAnd \quad (51)\\ &(FuzzyMember(MaxPossibleServoAssistance, 5, 0, 7, 1),\\ &FuzzyMember(Spread30/Median30, 0.25, 1, 0.5, 0),\\ &FuzzyMember(Spread30, 2, 1, 5, 0),\\ &FuzzyMember(Median30, 2, 0, 6, 1),\\ &FuzzyMember(Spread90, 2, 1, 5, 0)) \end{aligned}$$

Order statistics are cleared at each “mask-on” event, so that from 90 seconds after such an event, step 71650 is permitted to compute the variable ShouldSpeedUpTargetVentilationAdjustment.

FIG. 7*q* is a flow chart illustrating a method 71700 of computing the target ventilation from the typical recent ventilation, which may be used to implement step 71460 of the method 71400 in one form of the present technology.

The method 71700 imposes an upper limit on the rate of increase (the upward slew rate) of the target ventilation.

The method 71700 starts at step 71710, which subtracts the current value of target ventilation from the typical recent ventilation multiplied by the target fraction, as provided by step 71440 of the method 71400, yielding a prospective increment to the target ventilation.

Step 71720 determines whether the prospective increment is greater than zero. If so ("Y"), the prospective increment is multiplied at step 71730 by the increasing rate constant, which in one implementation is set to a fixed value, typically $1/180$ $sec^{-1}$. The next step 71740 clips the resulting adjusted increment above to the upward slew rate limit, which in one implementation is set at 0.93 litres/minute/minute, corresponding to a target ventilation increase of 2.5 litres/minute per three minutes. The method 71700 then proceeds to step 71790, described below.

If step 71720 determined that the prospective increment is not greater than zero ("N"), step 71750 multiplies the prospective increment (actually a decrement) by the decreasing rate constant, and the following step 71760 multiplies the product by the SpeedUpRatio computed at step 71450 of the method 71400 to obtain the adjusted increment.

After either of steps 71740 and 71760, the method 71700 adds the adjusted increment to the current target ventilation to generate the new value of target ventilation. Step 71795 is an optional step described below.

Determination of Therapy Parameters 4329

The processor 4230 executes one or more algorithms 4329 for the determination of therapy parameters.

In one form of the present technology, the algorithm 4329 receives as an input one of more of the following:

i. A waveform value $\Pi(\Phi)$ in the range [0, 1] (from the algorithm 4322);

ii. A measure of instantaneous ventilation Vent (from the algorithm 4323);

iii. A target ventilation Vtgt (from the algorithm4328); and iv. An EPAP value (from the algorithm 4327).

The algorithm 4329 first computes a pressure support value A that is sufficient to increase the instantaneous ventilation to the target ventilation. In one implementation, the algorithm 4329 computes A in proportion to the integral of the difference between the target ventilation and the instantaneous ventilation:

$$A = G\int_t (Vtgt - Vent)dt \quad (52)$$

where G is the controller gain, typically set to 0.3 $cmH_20$ litres/min/second. Note that the computed pressure support A is clipped to the range [minSwing, maxSwing].

In implementations of the algorithm 4329, other forms of controller are used to compute the pressure support value A, from the target ventilation and the instantaneous ventilation, for example, proportional, proportional-integral, proportional-integral-differential.

The algorithm 4329 then computes the target treatment pressure Pt using the following equation:

$$Pt = EPAP + A * \Pi(\Phi) \quad (53)$$

In other forms of the present technology, the algorithm 4329 computes the pressure support value A as in equation (52). The therapy engine module 4320 then outputs the EPAP, the waveform value, and the computed value of pressure support A. The control module 4330 then performs the remaining computation of the target treatment pressure Pt as described above.

In other forms of the present technology, the algorithm 4329 merely outputs the EPAP, the waveform value, the target ventilation, and the instantaneous ventilation. The control module 4330 then performs the remaining computation of the target treatment pressure Pt as described above.

Patients with periodic breathing of central origin (such as CSR) rarely have significant respiratory insufficiency, because insufficiency decreases plant gain and so tends to stabilise the patient, even in the presence of high respiratory controller gain. However, this combination does occur occasionally. The mechanism may involve a lung disease in which arterial oxygen saturations are relatively low without corresponding increases in work of breathing, the steep part of the oxyhaemoglobin saturation curve increasing the plant gain and, with these patients, operating in a region where oxygen is an important part of respiratory controller drive. Such patients may have central breathing instability in slow wave sleep, possibly exacerbated by some degree of cardiac failure, combined with marked REM desaturation. While oxygen is the principal therapy for these patients, it may be insufficient to stabilise the breathing stability, and the REM desaturation may be ameliorated to some extent by ventilatory support.

The conventional approach to such patients is to set a high enough level of minimum pressure support for there to be adequate ventilatory support in REM to address the respiratory insufficiency, as there is no periodic breathing during REM. However, this is unsatisfactory, because it diminishes the range of pressure support available to counteract the ventilatory instability at other times. A preferable approach is to set a minimum target ventilation. This may be implemented straightforwardly in the method 71700, by inserting an optional step 71795 (shown as a dashed box in FIG. 7*q*) that bounds the target ventilation below by the set minimum target ventilation. In one implementation, the minimum target ventilation rises gradually from zero to its set level, to allow the patient to get to sleep before the target ventilation is bounded below by the minimum target ventilation.

Another approach is to set a minimum target gross alveolar ventilation (as described in the commonly owned U.S. Patent Application Publication No. 20070163590 A1, the disclosure of which is incorporated herein by reference), and to combine the control methodology based on gross alveolar ventilation described in that disclosure with the control methodology of algorithm 4329 described above.

To combine the two methodologies, one implementation is to run both in parallel, and adjust the pressure support to some combination of the values of pressure support set by each methodology. In one implementation, the combination is the greater of the two values.

The advantage of this combined approach is that a small tidal volume at a high respiratory rate, which may produce a low gross alveolar ventilation but an adequate total ventilation, gets an appropriate increase in pressure support rather than being regarded as satisfactory ventilation and not producing any increase in pressure support. This is not normally an issue in patients with typical central breathing instability, such as Cheyne Stokes, whose respiratory rates are generally in the normal range, but is important in respiratory insufficiency, where rapid shallow breathing may occur.

Control Module 4330

A control module 4330 in accordance with one form of the present technology receives as an input a target treatment pressure Pt, and controls a therapy device 4245 to deliver that pressure.

A control module 4330 in accordance with another form of the present technology receives as inputs an EPAP, a waveform value, and a level of pressure support, computes a target treatment pressure Pt as in equation (53), and controls a therapy device 4245 to deliver that pressure.

A control module 4330 in accordance with another form of the present technology receives as an input an EPAP, a waveform value, a target ventilation, and an instantaneous ventilation, computes a level of pressure support from the target ventilation and the instantaneous ventilation as in equation (52), computes a target treatment pressure Pt using the EPAP, the waveform value, and the pressure support as in equation (53), and controls a therapy device 4245 to deliver that pressure.

Detection of Fault Conditions 4340

In one form of the present technology, a processor executes one or more methods for the detection of fault conditions. Preferably the fault conditions detected by the one or more methods includes at least one of the following:

- Power failure (no power, or insufficient power)
- Transducer fault detection
- Failure to detect the presence of a component
- Operating parameters outside recommended ranges (e.g. pressure, flow, temperature, $PaO_2$)
- Failure of a test alarm to generate a detectable alarm signal.

Upon detection of the fault condition, the corresponding algorithm signals the presence of the fault by one or more of the following:

- Initiation of an audible, visual &/or kinetic (e.g. vibrating) alarm
- Sending a message to an external device
- Logging of the incident Therapy Device 4245

In a preferred form of the present technology, the therapy device 4245 is under the control of the control module 4330 to deliver therapy to a patient 1000.

Preferably the therapy device 4245 is a positive air pressure device 4140.

Humidifier 5000

In one form of the present technology there is provided a humidifier 5000 comprising a water reservoir 5110 and a heating plate 5120.

Glossary

For purposes of the present technology disclosure, in certain forms of the present technology, one or more of the following definitions may apply. In other forms of the present technology, alternative definitions may apply.

General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimetres of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Volute: The casing of the centrifugal pump that receives the air being pumped by the impeller, slowing down the flow rate of air and increasing the pressure. The cross-section of the volute increases in area towards the discharge port.

Aspects of the Respiratory Cycle

Apnea: An apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

- (i) Flattened: Having a rise followed by a relatively flat portion, followed by a fall.
- (ii) Chair-shaped: Having a single local peak, the peak being at the leading edge, followed by a relatively flat portion.
- (iii) Reverse-chair shaped: Having a relatively flat portion followed by single local peak, the peak being at the trailing edge.
- (iv) M-shaped: Having two local peaks, one at the leading edge, and one at the trailing edge, and a relatively flat portion or a dip between the two peaks.

Hypopnea: A hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:

- (i) a 30% reduction in patient breathing for at least 10 seconds plus an associated 4% desaturation; or
- (ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: A flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, g-f/$cm^2$, hectopascal. 1 $cmH_2O$ is equal to 1 g-f/$cm^2$ and is approximately 0.98 hectopascal. In this specification, unless otherwise stated, pressure is given in units of $cmH_20$. For nasal CPAP treatment of OSA, a reference to treatment pressure is a reference to a pressure in the range of about 4-20 $cmH_2O$, or about 4-30 $cmH_2O$. The pressure in the patient interface (or, more succinctly, mask pressure) is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20\times10^{-6}$ pascal (Pa), considered the threshold of human hearing.

Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: a parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the device aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

Ventilator inspiration and ventilator expiration: the periods during which the ventilator considers that it should deliver pressures appropriate respectively to patient inspiration and expiration. Depending on the quality of patient-ventilator synchronisation, and the presence of upper airway obstruction, these may or may not correspond to actual patient inspiration or expiration.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

Mathematical Terms

Fuzzy logic is used in a number of places in this technology. The following is used to indicate a fuzzy membership function, which outputs a "fuzzy truth value" in the range [0, 1], 0 representing fuzzy false and 1 representing fuzzy true:

FuzzyMember (ActualQuantity, ReferenceQuantity1, FuzzyTruthValueAtReferenceQuantity1, ReferenceQuantity2, FuzzyTruthValueAtReferenceQuantity2, . . . , ReferenceQuantityN, FuzzyTruthValueAtReferenceQuantityN)

A fuzzy membership function is defined as $$FuzzyMember(x, x_1, f_1, x_2, f_2, \ldots, x_N, f_N) = \begin{cases} f_1, & x < x_1 \\ f_N, & x \geq x_N \\ InterpOnInterval(x, x_k, f_k, x_{k+1}, f_{k+1}), & x_k \leq x < x_{k+1}, 1 \leq k \leq N \end{cases}$$

where $$InterpOnInterval(x, x_k, f_k, x_{k+1}, f_{k+1}) = \begin{cases} f_k + \dfrac{(f_{k+1} - f_k)(x - x_k)}{x_{k+1} - x_k}, & x_k \neq x_{k+1} \\ f_k & \text{otherwise} \end{cases},$$

the $f_j$ are fuzzy truth values, and x and the $x_j$ are real numbers.

The function "Interp" is defined to be the same as "FuzzyMember", except that the values $f_k$ are interpreted as real numbers rather than fuzzy truth values.

The fuzzy "Or" of fuzzy truth values is the maximum of those values; the fuzzy "And" of fuzzy truth values is the minimum of these values. These will be indicated by the functions FuzzyOr and FuzzyAnd of two or more fuzzy truth values. It is to be understood that other typical definitions of these fuzzy operations would work similarly in the present technology.

"Exponential decay towards zero" with a time constant τ means that during any period of decay starting at time t=T, the value of the decaying quantity V is given by $$V(t) = V(T) * \exp\left(-\frac{t-T}{\tau}\right)$$

Advantages

The oscillations in central drive to the respiratory musculature associated with Cheyne-Stokes Respiration may be associated with oscillations in drive to the upper airway musculature, exacerbating any tendency to upper airway obstruction. Any method which attempts to counteract the self-sustaining oscillations in respiratory drive by ventilating the patient, typically with more ventilator drive during periods of low patient effort than during periods of high patient effort, needs the upper airway to be substantially open when it is attempting to deliver ventilatory assistance, otherwise the ventilatory assistance will be to some extent, and often totally, ineffective during the periods of low or zero patient effort, and thus unable to stabilise the patient's ventilation.

This need to keep the upper airway open is typically addressed by attempting to set an expiratory positive airway pressure (EPAP) such that the upper airway is kept open at all times. This may be achieved by some kind of iterative adjustment of EPAP while observing indicators of the patency of the airway at various EPAP levels, in a procedure called a titration. Titration is a skilled and typically expensive operation, preferably being conducted in a sleep laboratory, and may not yield an EPAP sufficient to overcome upper airway obstruction (UAO). Reasons for this include the fact that UAO is often postural, and the patient may never during the titration night assume the posture which produces the worst UAO, typically the supine posture. Sedative and other drugs may variably influence the upper airway. There is also evidence that the degree of cardiac failure affects the degree of upper airway obstruction via oedema of the upper airway. Hence an exacerbation of cardiac failure may worsen upper airway obstruction to an extent which cannot be anticipated during a titration night.

An advantage of the present technology is therefore the ability to diagnose and/or treat the combination of CSR and OSA at the patient's home without the need for PSG and/or titration in a sleep laboratory.

A further advantage is the ability to treat the combination of CSR and OSA more effectively and in a manner that improves patient comfort.

In particular, an advantage is to counteract the tendency of automatic servo ventilators to inappropriately increase the target ventilation in response to artefacts such as uncompensated leak.

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

REFERENCE LABEL LIST patient 1000
patient interface 3000
structure 3100
plenum chamber 3200
structure 3300
vent 3400
connection port 3600
pap device 4000
external housing 4010
upper portion 4012
portion 4014
panel 4015
chassi 4016
handle 4018
pneumatic block 4020
pneumatic component 4100
air filter 4110
inlet air filter 4112
outlet air filter 4114
muffler 4120
inlet muffler 4122
outlet muffler 4124
controllable pressure device 4140
controllable blower 4142
brush less DC motor 4144
back valve 4160
air circuit 4170
supplemental oxygen 4180
electrical component 4200
PCBA 4202
electrical power supply 4210
input device 4220
processor 4230
clock 4232
therapy device controller 4240
therapy device 4245
protection circuit 4250
memory 4260
transducer 4270
pressure transducer 4272
flow 4274
motor speed signal 4276
data communication interface 4280
remote external communication network 4282
local external communication network 4284
such remote external device 4286
local external device 4288
output device 4290
display driver 4292
display 4294
algorithm module 4300
processing module 4310
pressure compensation algorithm 4312
vent flow 4314
leak flow 4316
respiratory flow 4318
algorithm 4319
therapy engine module 4320
phase determination algorithm 4321
waveform determination algorithm 4322
ventilation determination 4323
algorithm 4324
algorithm 4325
algorithm 4326
algorithm 4327
target ventilation 4328
therapy parameter 4329
control module 4330
fault condition 4340
humidifier 5000
water reservoir 5110
heating plate 5120
humidifier controller 5250
method 7100
step 7110
step 7120
step 7130
step 7140
step 7150
method 7200
step 7210
step 7220
method 7300
first step 7310
step 7320
step 7330
step 7335
step 7340
step 7350
step 7360
step 7370
method 7400
step 7410
step 7415
state detection step 7420
step 7425
step 7430
step 7435
step 7440
step 7445
step 7450
step 7455
step 7460
step 7470
step 7495
apnea detection method 7500
step 7510
step 7520
step 7530
step 7540
step 7550
step 7560
method 7600
step 7610
step 7620
step 7630
method 7700
step 7710
step 7720
step 7730
step 7735

Step 7740
step 7750
step 7760
step 7770
step 7780
step 7790
method 7800
step 7810
step 7820
step 7830
step 7840
step 7850
step 7860
step 7870
method 7900
step 7910
step 7920
step 7930
step 7940
step 7950
method 71000
step 71010
step 71020
step 71030
step 71040
step 71050
step 71060
step 71070
step 71080
method 71100
step 71110
step 71120
step 71130
step 71140
step 71150
step 71160
step 71170
step 71180
method 71200
implementation step 71210
step 71220
step 71230
step 71240
step 71250
step 71260
method 71300
step 71320
step 71330
step 71340
step 71350
step 71360
step 71370
method 71400
step 71410
step 71420
step 71430
next step 71440
step 71450
step 71460
method 71500
dependent filter 71510
step 71520
next step 71530
step 71540
current output sample step 71550
step 71560
step 71570
step 71580
ventilation filter 71590
method 71600
step 71610
step 71620
following step 71630
step 71640
step 71650
method 71700
step 71710
step 71720
step 71730
step 71740
step 71750
step 71760
step 71790
optional step 71795

The invention claimed is:

1. An apparatus for treating a respiratory disorder comprising a controller of a therapy device, the apparatus being configured to:

compute a measure of M-shaped inspiratory flow limitation, compute a proportion of maximum increase in expiratory positive airway pressure (EPAP) as a function of the measure of the M-shaped inspiratory flow limitation, adjust the proportion of maximum increase in EPAP dependent on a ratio of breathwise ventilation to typical recent ventilation, increase an EPAP value according to the adjusted proportion of maximum increase in EPAP; and control, with the controller and the therapy device, delivery of pressure based on the EPAP value.

2. The apparatus of claim 1, wherein the apparatus is further configured to decay the EPAP value toward a minimum EPAP value if the computed measure of M-shaped inspiratory flow limitation is zero.

3. The apparatus of claim 1, wherein the apparatus is further configured to, if inspiratory duration is greater than a threshold, decay the EPAP value to a minimum EPAP value.

4. The apparatus of claim 1, wherein the proportion of maximum increase in EPAP generally decreases as the ratio increases.

5. The apparatus of claim 1, wherein the M-shaped inspiratory flow limitation comprises an inspiratory flow waveform having two local peaks, one local peak at a leading edge of the inspiratory flow waveform, and one local peak at a trailing edge of the inspiratory flow waveform, and a relatively flat portion or a dip between the two local peaks.

6. The apparatus of claim 1 wherein the controller is configured with the therapy device to control delivery of the pressure, wherein the therapy device comprises a motor-driven blower.

7. A method for treating a respiratory disorder, the method comprising:

computing a measure of M-shaped inspiratory flow limitation, compute a proportion of maximum increase in expiratory positive airway pressure (EPAP) as a function of the measure of the M-shaped inspiratory flow limitation, adjust the proportion of maximum increase in EPAP dependent on a ratio of breathwise ventilation to typical recent ventilation, increasing an EPAP value according to the adjusted proportion of maximum increase in EPAP; and controlling, with a controller and a therapy device, delivery of pressure based on the EPAP value.

8. The method of claim 7, further comprising decaying the EPAP value toward a minimum EPAP value when the computed measure of the M-shaped inspiratory flow limitation is zero.

9. The method of claim 7, further comprising decaying the EPAP value to a minimum EPAP value when inspiratory duration is greater than a threshold.

10. The method of claim 7, wherein the proportion of maximum increase in EPAP generally decreases as the ratio increases.

11. The method of claim 7, wherein the M-shaped inspiratory flow limitation comprises an inspiratory flow waveform having two local peaks, one at a leading edge of the inspiratory flow waveform, and one at a trailing edge of the inspiratory flow waveform, and a relatively flat portion or a dip between the two local peaks.

12. The method of claim 7 further comprising controlling a motor-driven blower of the therapy device to deliver the pressure.

13. A non-transitory computer readable storage medium comprising stored processor control instructions configured to control a processor of a respiratory apparatus for treating a respiratory disorder, wherein the stored processor control instructions, when executed by the processor, cause the processor to:

compute a measure of M-shaped inspiratory flow limitation, compute a proportion of maximum increase in expiratory positive airway pressure (EPAP) as a function of the measure of the M-shaped inspiratory flow limitation, adjust the proportion of maximum increase in EPAP dependent on a ratio of breathwise ventilation to typical recent ventilation, increase an EPAP value according to the adjusted proportion of maximum increase in EPAP, and control delivery of pressure based on the EPAP value.

14. The computer readable storage medium of claim 13, wherein the stored processor control instructions are further configured to decay the EPAP value toward a minimum EPAP value if the computed measure of M-shaped inspiratory flow limitation is zero.

15. The computer readable storage medium of claim 13, wherein the stored processor control instructions are further configured to decay the EPAP value to a minimum EPAP value if inspiratory duration is greater than a threshold.

16. The computer readable storage medium of claim 13, wherein the proportion of maximum increase in EPAP generally decreases as the ratio increases.

17. The computer readable storage medium of claim 13, wherein the M-shaped inspiratory flow limitation comprises an inspiratory flow waveform having two local peaks, one at a leading edge of the inspiratory flow waveform, and one at a trailing edge of the inspiratory flow waveform, and a relatively flat portion or a dip between the two local peaks.

18. The computer readable storage medium of claim 13 wherein the stored processor control instructions are further configured to produce output to control a therapy device comprising a motor-driven blower to deliver the pressure.

19. An apparatus for treating a respiratory disorder, the apparatus comprising a controller of a therapy device, the apparatus being configured to:

compute a measure of M-shaped inspiratory flow limitation, compute a plurality of separate pressure components for an increase in expiratory positive airway pressure (EPAP), wherein a pressure component of the computed plurality of separate pressure components is a proportion of a maximum increase in expiratory positive airway pressure (EPAP) that is due to the measure of M-shaped inspiratory flow limitation, adjust the pressure component that is the proportion of maximum increase in EPAP, dependent on a ratio of breathwise ventilation to typical recent ventilation, and increase an EPAP value with the pressure component that is the adjusted proportion of maximum increase in EPAP control, with the controller and the therapy device, delivery of pressure based on the EPAP value.

* * * * *